(12) United States Patent
Greshock et al.

(10) Patent No.: US 10,221,167 B2
(45) Date of Patent: Mar. 5, 2019

(54) HYDROXYALKYLAMINE- AND HYDROXYCYCLOALKYLAMINE-SUBSTITUTED DIAMINE-ARYLSULFONAMIDE COMPOUNDS WITH SELECTIVE ACTIVITY IN VOLTAGE-GATED SODIUM CHANNELS

(71) Applicant: Merck Sharp & Dohme Corp., Rahway, NJ (US)

(72) Inventors: Thomas J. Greshock, Collegeville, PA (US); James Mulhearn, Elkins Park, PA (US); Junying Zheng, New Providence, NJ (US); Ronald M. Kim, Summit, NJ (US); Ting Zhang, Princeton Junction, NJ (US); Anthony J. Roecker, Harleysville, PA (US); Walter Won, Alpine, NJ (US); Philippe Nantermet, Lansdale, PA (US); Rajan Anand, Fanwood, NJ (US); Gang Zhou, Bridgewater, NJ (US); Deping Wang, Furlong, PA (US); Liangqin Guo, Edison, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/378,465

(22) Filed: Dec. 14, 2016

(65) Prior Publication Data
US 2017/0174674 A1    Jun. 22, 2017

Related U.S. Application Data

(60) Provisional application No. 62/420,956, filed on Nov. 11, 2016, provisional application No. 62/290,235, filed on Feb. 2, 2016, provisional application No. 62/269,327, filed on Dec. 18, 2015.

(51) Int. Cl.

| | | |
|---|---|---|
| *C07D 417/12* | (2006.01) |
| *C07D 285/08* | (2006.01) |
| *C07D 277/52* | (2006.01) |
| *A61K 31/4178* | (2006.01) |
| *A61K 31/4196* | (2006.01) |
| *A61K 31/4168* | (2006.01) |
| *A61K 31/426* | (2006.01) |
| *A61K 31/427* | (2006.01) |
| *A61K 31/433* | (2006.01) |
| *A61K 31/551* | (2006.01) |
| *A61K 45/06* | (2006.01) |

(52) U.S. Cl.
CPC .......... *C07D 417/12* (2013.01); *A61K 31/426* (2013.01); *A61K 31/427* (2013.01); *A61K 31/433* (2013.01); *A61K 31/551* (2013.01); *A61K 45/06* (2013.01); *C07D 277/52* (2013.01); *C07D 285/08* (2013.01)

(58) Field of Classification Search
CPC combination set(s) only.
See application file for complete search history.

(56) References Cited

U.S. PATENT DOCUMENTS

| | | |
|---|---|---|
| 7,223,782 B2 | 5/2007 | Atkinson et al. |
| 7,244,744 B2 | 7/2007 | Gross et al. |
| 8,106,087 B2 | 1/2012 | Chafeev et al. |
| 8,124,610 B2 | 2/2012 | Fulp et al. |
| 8,153,814 B2 | 4/2012 | Beaudoin et al. |
| 8,415,370 B2 | 4/2013 | Chafeev et al. |
| 8,466,188 B2 | 6/2013 | Chafeev et al. |
| 8,541,588 B2 | 9/2013 | Beaudoin et al. |
| 8,592,692 B2 | 11/2013 | Sharf et al. |
| 8,742,109 B2 | 6/2014 | Cadieux et al. |
| 8,772,293 B2 | 7/2014 | Brown et al. |
| 8,853,250 B2 | 10/2014 | Beaudoin et al. |
| 8,883,840 B2 | 11/2014 | Chafeev et al. |
| 8,907,101 B2 | 12/2014 | Beaudoin et al. |
| 8,933,236 B2 | 1/2015 | Chowdhury et al. |
| 8,952,169 B2 | 2/2015 | Andrez et al. |
| 9,012,443 B2 | 4/2015 | Boezio et al. |
| 9,051,311 B2 | 6/2015 | Dineen et al. |
| 9,079,902 B2 | 7/2015 | Dineen et al. |
| 9,096,558 B2 | 8/2015 | Greener et al. |
| 9,145,407 B2 | 9/2015 | Markworth et al. |
| 9,212,182 B2 | 12/2015 | Weiss et al. |
| 9,260,446 B2 | 2/2016 | Cadieux et al. |
| 9,273,040 B2 | 3/2016 | Layton et al. |
| 9,278,088 B2 | 3/2016 | MacDonald et al. |
| 9,376,429 B2 | 6/2016 | Kim et al. |
| 9,388,179 B2 | 7/2016 | Pero et al. |
| 9,458,118 B2 | 10/2016 | Babich et al. |
| 9,458,152 B2 | 10/2016 | Weiss et al. |

(Continued)

FOREIGN PATENT DOCUMENTS

| | | |
|---|---|---|
| JP | 2014-101287 | 5/2014 |
| WO | WO2005013914 | 2/2005 |

(Continued)

OTHER PUBLICATIONS

24268—International Search Report—dated Jan. 30, 2017.

*Primary Examiner* — Amanda L Aguirre
(74) *Attorney, Agent, or Firm* — Sylvia A. Ayler; John C. Todaro

(57) ABSTRACT

Disclosed are compounds of Formula A, or a salt thereof:

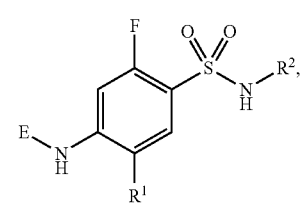

Formula A wherein $R^1$, $R^2$, and E are defined herein, which compounds have properties for inhibiting $Na_v$ 1.7 ion channels found in peripheral and sympathetic neurons. Also described are pharmaceutical formulations comprising the compounds of Formula A or their salts, and methods of treating pain disorders, cough, and itch using the same.

46 Claims, No Drawings

(56) References Cited

U.S. PATENT DOCUMENTS

| | | |
|---|---|---|
| 9,481,677 B2 | 11/2016 | Liu et al. |
| 9,493,429 B2 | 11/2016 | Chen et al. |
| 9,504,671 B2 | 11/2016 | Winters et al. |
| 9,546,164 B2 | 1/2017 | Andrez et al. |
| 9,550,775 B2 | 1/2017 | Bichler et al. |
| 9,624,208 B2 | 4/2017 | Pero et al. |
| 9,630,929 B2 | 4/2017 | Sun et al. |
| 9,663,508 B2 | 5/2017 | Bregman et al. |
| 9,694,002 B2 | 7/2017 | Andrez et al. |
| 9,771,376 B2 | 9/2017 | Chowdhury et al. |
| 9,776,995 B2 | 10/2017 | Weiss et al. |
| 2010/0197655 A1 | 8/2010 | Beaudoin et al. |
| 2011/0172282 A9 | 7/2011 | Chafeev et al. |
| 2014/0357685 A1 | 12/2014 | Beaudoin et al. |
| 2015/0291514 A1 | 10/2015 | Brown et al. |
| 2015/0322002 A1 | 11/2015 | Dehnhardt et al. |
| 2016/0046617 A1 | 2/2016 | Babich et al. |
| 2016/0159815 A1 | 6/2016 | Deninno et al. |
| 2017/0137415 A1 | 5/2017 | Ramdas et al. |
| 2017/0190662 A1 | 7/2017 | Andrez et al. |

FOREIGN PATENT DOCUMENTS

| | | | |
|---|---|---|---|
| WO | WO2009012242 | 1/2009 | |
| WO | WO-2009012242 A2 * | 1/2009 | ........... C07D 413/12 |
| WO | WO2015006280 A1 | 1/2015 | |
| WO | WO2015013914 | 2/2015 | |
| WO | WO2015077905 | 6/2015 | |
| WO | WO-2015077905 A1 * | 6/2015 | ........... C07D 471/04 |
| WO | WO2015151001 A1 | 10/2015 | |
| WO | WO2016007534 A1 | 1/2016 | |
| WO | WO2017106409 A1 | 6/2017 | |
| WO | WO2017165204 A1 | 9/2017 | |
| WO | WO2018093694 A1 | 5/2018 | |

* cited by examiner

HYDROXYALKYLAMINE- AND HYDROXYCYCLOALKYLAMINE-SUBSTITUTED DIAMINE-ARYLSULFONAMIDE COMPOUNDS WITH SELECTIVE ACTIVITY IN VOLTAGE-GATED SODIUM CHANNELS

BACKGROUND

Voltage-gated sodium channels play a central role in initiating and propagating action potentials in electrically excitable cells such as neurons and muscle, see for example Yu and Catterall, Genome Biology 4:207 (2003) and references therein. Voltage-gated sodium channels are multimeric complexes characterized by an Alpha-subunit which encompasses an ion-conducting aqueous pore, and is the site of the essential features of the channel, and at least one Beta-subunit that modifies the kinetics and voltage-dependence of the channel gating. These structures are ubiquitous in the central and peripheral nervous system where they play a central role in the initiation and propagation of action potentials, and also in skeletal and cardiac muscle where the action potential triggers cellular contraction. (see Goldin, Ann NY Acad Sci. 30; 868:38-50 (1999)).

Sensory neurons are also responsible for conveying information from the periphery e.g. skin, muscle and joints to the central nervous system (spinal cord). Sodium channels are integral to this process as sodium channel activity is required for initiation and propagation of action potentials triggered by noxious stimuli (thermal, mechanical and chemical) activating peripheral nociceptors.

Nine different Alpha-subunits have been identified and characterized in mammalian voltage-gated sodium channels. These structures are designated $Na_v$ 1.X sodium channels (X=1 to 9) in accordance with currently accepted nomenclature practice, designating their ion selectivity (Na), the physiological regulator ('v', potential, i.e. voltage), and the gene subfamily encoding them (1.), with the number designator X (1 to 9) being assigned for the alpha subunit present in the structure (see Aoldin et al., Neuron, 28:365-368 (2000)). $Na_v$1.7 voltage-gated sodium ion channels (herein designated "Nav 1.7 channels" in some instances for convenience) are expressed primarily in sensory and sympathetic neurons, are believed to play a role in various maladies, for example, nociception, cough, and itch, and in particular have a central role in inflammatory pain perception, (see Wood et al. J. Neurobiol. 61: pp 55-71 (2004), Nassar et al., *Proc. Nat. Acad. Sci.* 101(34): pp 12706-12711 (2004), Klinger et. al., Molecular Pain, 8:69 (2012), see Devigili et. al., Pain, 155(9); pp 1702-7 (2014), Lee et. al., Cell, 157:1-12 (2014), Muroi et. al., Lung, 192:15-20 (2014), Muroi et. al., Am J Physiol Regul Integr Comp Physiol 304:R1017-R1023 (2013)).

Loss of function mutations in $Na_V$1.7 lead to Congenital Insensitivity to Pain (CIP), where patients exhibit a lack of pain sensation for a variety of noxious stimuli (Goldberg et al., Clinical Genetics, 71(4): 311-319 (2007)). Gain of function mutations in $Na_V$1.7, $Na_V$1.8, and $Na_V$1.9 manifest in a variety of pain syndromes where patients experience pain without an external stimulus (Fischer and Waxman, Annals of the New York Academy of Sciences, 1184:196-207 (2010), Faber et al., PNAS 109(47): 19444-19449) (2012), Zhang et al., American Journal of Human Genetics, 93(5):957-966 (2013)).

Accordingly, it is believed that identification and administration of agents which interact to block $Na_v$ 1.7 voltage-gated sodium ion channels represents a rational approach which may provide treatment or therapy for disorders involving $Na_v$1.7 receptors, for example, but not limited to, those conditions mentioned above (acute pain, preoperative pain, perioperative pain, post-operative pain, neuropathic pain, cough, or itch disorders, as well as those stemming specifically from dysfunction of $Na_v$1.7 voltage-gated sodium ion channels, see Clare et al., Drug Discovery Today, 5: pp 506-520 (2000)).

It has been shown in human patients as well as in animal models of neuropathic pain that damage to primary afferent sensory neurons can lead to neuroma formation and spontaneous activity, as well as evoked activity in response to normally innocuous stimuli. [Carter, G. T. and Galer, B. S., Advances in the Management of Neuropathic Pain, Physical Medicine and Rehabilitation Clinics of North America, 2001, 12(2): pp 447 to 459]. Injuries of the peripheral nervous system often result in neuropathic pain persisting long after an initial injury resolves. Examples of neuropathic pain include, for example, post herpetic neuralgia, trigeminal neuralgia, diabetic neuropathy, chronic lower back pain, phantom limb pain, pain resulting from cancer and chemotherapy, chronic pelvic pain, complex regional pain syndrome and related neuralgias. The ectopic activity of normally silent sensory neurons is thought to contribute to the generation and maintenance of neuropathic pain, which is generally assumed to be associated with an increase in sodium channel activity in the injured nerve. [Baker, M. D. and Wood, J. N., Involvement of Na Channels in Pain Pathways, TRENDS is Pharmacological Sciences, 2001, 22(1): pp 27 to 31.

Nociception is essential for survival and often serves a protective function. However, the pain associated with surgical procedures and current therapies to relieve that pain, can delay recovery after surgery and increase the length of hospital stays. As many as 80% of surgical patients experience post-operative pain, which arises as a result of tissue damage, including damage to peripheral nerves and subsequent inflammation). Furthermore, 10-50% of surgical patients will develop chronic pain after surgery often because the nerve damage results in lasting neuropathic pain once the wound has healed (Meissner et al., Current Medical Research and Opinion, 31(11):2131-2143 (2015)).

Cough is one of the most prevalent symptoms for which patients seek the attention of their primary care physicians; chronic cough for example is estimated to affect approximately 40% of the population. The fundamental mechanisms of the cough reflex are complex and involve an array of events initiated by the activation of airway sensory nerves that physically results in a forced expiration of the airways. This protective reflex is necessary to remove foreign material and secretions from the airways, however, chronic, non-protective cough results in a dramatic negative impact on quality of life (see Nasra et. al., Pharmacology & Therapeutics, 124(3):354-375 (2009)).

Cough symptoms can arise from the common cold, allergic and vasomotor rhinitis, acute and chronic bacterial sinusitis, exacerbation of chronic obstructive pulmonary disease, *Bordetella pertussis* infection, asthma, postnasal-drip syndromes, gastroesophageal reflux disease, eosinophilic and chronic bronchitis, and angiotensin-converting-enzyme inhibitors, cough is categorically described as acute, subacute, or chronic, respectively lasting less than three weeks, three to eight weeks, and more than eight weeks in duration (see Irwin et. al., The New England Journal of Medicine, 343(23):1715-1721 (2000)).

Current standard of care for the treatment of cough consists of centrally and peripherally acting suppressants such as opioids and local anesthetics respectively, both of which are dose-limited by side-effects (see Cox et. al., Best Practice & Research Clinical Anesthesiology, 117(1):111-136 (2003) and Benyamin et. al., Pain Physician, 11:S105-S120 (2008)). Opioids primarily act on μ-opioid receptors of the central nervous system, and in some reports, also on peripheral afferents of the cough reflex arc—they exhibit varied degrees of efficacy and are limited by side-effects such as sedation, physical dependence, and gastrointestinal problems; morphine has shown to be an effective treatment for chronic cough (see Morice et. al., Am J Respir Crit Care Med 175:312-315 (2007) and Takahama et. al., Cough 3:8 (2007)), but is generally restricted to patients with terminal illness such as lung cancer. Codeine, found in some cough syrups, and also administered systemically, was found no more effective than placebo (see Smith et. al., Journal of Allergy and Clinical Immunology, 117:831-835 (2006). Local anesthetics act peripherally by reducing the generation of action potentials in sensory nerves of the airway as a result of non-selectively inhibiting all voltage gated sodium channel subtypes and have demonstrated varied degrees of efficacy in treating cough. These compounds are often found in over-the-counter lozenges and have been shown to relieve cough when administered via nebulisation (see Nasra et. al., Pharmacology & Therapeutics, 124(3):354-375 (2009) and Hansson et. al., Thorax, 49(11):1166-1168 (1994)). However, in a study with chronic obstructive pulmonary disease patients, lidocaine was not effective (see Chong et. al., Emerg Med J, 22(6):429-32 (2005)).

In pre-clinical animals, $Na_v1.7$, $Na_v1.8$, and $Na_v1.9$ were determined to be the primary voltage-gated sodium channels expressed in the afferent nerves of the respiratory tract (see Muroi et. al., Lung, 192:15-20 (2014)) and in animal models of cough, suppression of $Na_v1.7$ function resulted in a marked decrease in number of coughs (see Muroi et. al., Am J Physiol Regul integr Comp Physiol, 304:R1017-R0123 (2013)), thus, combined with previous evidence that local anesthetics can be effective antiitussive agents, the targeted blockade of $Na_v1.7$ channels is believed to represent a rational approach for the treatment of cough with a preferential side-effect profile as compared to local anesthetics. Local anesthetics undesirably inhibit all voltage gated sodium channels, such as NaV1.5 channels which are found in heart muscle (see Rook et. al., Cardiovascular Research 93:12-23 (2012)).

Pruritus, also commonly known as itch, affects approximately 4% of the global population (see Flaxman et. al., Lancet, 380:2163-2196 (2012)) is "an unpleasant sensation that elicits the desire or reflex to scratch" and is regarded as closely related to pain. Theories on the origin of itch implicate the subtle, low-frequency activation of nociceptors (pain-sensing neurons), however, it has been described that some afferents preferentially respond to histamine, which induces itch (see Schmelz et. al., J Neuroscience, 17(20): 8003-8008 (1997)). At the same time, it has been found that histamine-responding neurons also respond to capsaicin which produces pain (see McMahon et. al., Trends. Neurosci., 15:497-501 (1992)). Members of the transient receptor potential (TRP) family, and nerve growth factor (NGF) are both known to play a role in itch and pain, and clinically, both maladies are treated with therapeutic agents such as gabapentin and antidepressants as such, it continues to be accepted that the underlying mechanisms of pain and itch are highly interwoven and complex, and distinguishing pan-selective or itch-selective pathways remains ambiguous (see Ikoma et. al., Nature Reviews Neuroscience, 7:535-547 (2006)).

Itch, both chronic and acute, can arise from many different insults and diseases and may be classified as dermal or pruriceptive, neurogenic, neuropathic, or psychogenic: itch can arise from both systemic disorders, skin disorders, as well as physical or chemical insult to the dermis. Pathologically, conditions such as dry skin, eczema, psoriasis, varicella zoster, urticaria, scabies, renal failure, cirrhosis, lymphoma, iron deficiency, diabetes, menopause, polycythemia, uremia, and hyperthyroidism can cause itch, as can diseases of the nervous system such as tumors, multiple sclerosis, peripheral neuropathy, nerve compression, and delusions related to obsessive-compulsive disorders. In skin, pruritogens are released from keratinocytes, lymphocytes, mast cells, and eosinophils during inflammation. These molecules act directly on free nerve endings to induce itch; medicines such as opioids and chloroquine can also trigger itch (see Ikoma et. al., Nature Reviews Neuroscience, 7:535-547 (2006)). Itching following burn is also an extremely serious clinical problem as it hampers the healing process, results in permanent scaring, and negatively impacts quality of life (see Loey et. al., British Journal of Dermatology, 158:95-100 (2008)).

Gain of function mutations of $Na_v1.7$ have been found in approximately 28% of patients with idiopathic small fiber neuropathy (I-SFN); these mutations were found to render dorsal root ganglia neurons hyperexcitable, reducing the threshold of activation and increasing the frequency of evoked firing (see Waxman et. al., Neurology, 78(21):1635-1643 (2012)). Severe, uncontrollable itch has also been genetically linked to a gain-of-function mutation (I739V) in the sodium channel $Na_v1.7$ in man (see Devigili et. al., Pain, 155(9); pp 1702-7 (2014)). Additionally, the sea-anemone toxin ATX-II has been found to elicit pain and itch in human volunteers after intradermal injection on the forearm; electrophysiology studies revealed that ATX-II enhanced $Na_v1.7$ and $Na_v1.6$ resurgent currents (see Klinger et. al., Molecular Pain, 8:69 (2012)). It has been demonstrated in animal models that selective blockade of $Na_v1.7$ channels can effectively suppress both inflammatory and neuropathic pain, as well as acute and chronic itch, thus blockade of $Na_v1.7$ channels is believed to represent a rational approach to treatment of pain and itch disorders (see Lee et. al., Cell, 157:1-12 (2014)).

Because voltage gated sodium ion channels are ubiquitous in the central and peripheral nervous system, as well as in both cardiac and skeletal muscle, and conservation of structures in the various Alpha-subunits characterizing voltage-gated sodium ion channels implicates the potential for producing serious side effects when utilizing therapeutic agents having a mechanism of action that target inhibiting voltage-gated sodium ion channels, for example, therapeutic agents suitable for use in addressing nociception, cough, or itch disorders, requires therapeutic agents having specificity in their action, for example, discriminating between action upon $Na_v1.5$ sodium ion channels, thought to be important in regulation of cardiac function and action upon $Na_v1.7$ sodium ion channels, thought to be central in inflammatory nociception, cough, or itch and disorders arising from dysfunctional $Na_v1.7$ sodium ion channels.

There remains a need for additional compounds having high potency for inhibiting $Na_v1.7$ sodium ion channels and selective activity for $Na_v1.7$ sodium ion channels providing structural variety to facilitate rational development of therapeutic agents for use as a selective $Na_v1.7$ sodium ion channel inhibitor.

SUMMARY OF THE INVENTION

In one aspect, the invention provides compounds having selective activity as $Na_v 1.7$ sodium ion channel inhibitors which have the structure of Formula A, or a pharmaceutically acceptable salt thereof:

Formula A wherein:
$R^1$ is: —Cl, —Br, or linear, branched or cyclic alkyl of up to 3 carbon atoms;
$R^2$ is:
(a) a moiety of the formula:

wherein, one of $R^{3a}$ and $R^{3b}$ is —H and the other is —H, —F, $CH_3$; or
(b) a moiety of the formula:

and
E is:
(I) a moiety of Formula $E^1$:

Formula $E^1$

Wherein:
$R^6$ is —H or a linear, branched or cyclic alkyl of up to 6 carbon atoms; and
B is:
(a) a moiety of the formula:

which moiety is bonded to nitrogen at one of $R^{7A}$, $R^{7B}$, or $R^{7C}$ via —$CH_2$—, or is bonded to nitrogen directly at one of $R^{7C}$, and wherein:
m is 0, 1 or 2;
$R^{7A}$ and $R^{7B}$ are independently for each occurrence —H, or a linear, branched or cyclic alkyl of up to 3 carbon atoms when not selected to be bonded to the nitrogen via methylene;
$R^{7C}$ when not selected to be bonded to the nitrogen directly or via methylene is independently for each occurrence: (i) —H; (ii) linear, branched, or cyclic alkyl of up to three carbon atoms; and
$R^{7D}$ is: (ai) —H; or (aii) a linear, branched or cyclic alkyl of up to 5 carbon atoms; or
(b) a moiety of the formula:

wherein:
$R^{7h}$ is —H or a linear, branched or cyclic alkyl of up to 3 carbon atoms; and
$R^{7g}$ and $R^{7f}$ are selected as follows:
(i) $R^{7g}$ is a linear alkyl of at least 2, up to 4 carbon atoms, a branched alkyl of at least 3 up to 6 carbon atoms or cyclic alkyl of up to 6 carbon atoms and $R^{7f}$ is a linear alkyl of at least 2 carbon atoms up to 4 carbon atoms, or a branched or cyclic alkyl of up to 6 carbon atoms which is substituted with —OH on one carbon atom thereof that is bonded beta to, or further from, the nitrogen to which it is attached; or
(ii) $R^{7f}$ is —H or a linear, branched or cyclic alkyl of up 6 carbon atoms or and $R^{7g}$ is —$(CH_2)_{1-2}$—(HC(OH))—$(CH_2)_{1-2}$;
(II) a moiety of Formula $E^2$:

Formula $E^2$ wherein each $R^8$ is independently —H or linear, branched, or cyclic alkyl of up to 6 carbon atoms; or
(III) a moiety of Formula $E^3$:

Formula $E^3$ wherein:
$R^{9A}$ is independently for each occurrence: (i) —H; (ii) —OH; or (iii) a linear, branched or cyclic alkyl of up to 6 carbon atoms which is optionally substituted on one carbon atom there of with an —OH;
$R^{10A}$ is independently for each occurrence: (i) —H; or (ii) linear, branched or cyclic alkyl of up to 6 carbon atoms which is optionally substituted on one carbon atom thereof with an —OH;
$R^{11A}$ is —H or an alkyl of 2 or 3 carbons which is optionally substituted on a beta or gamma carbon with an —OH,
with the proviso that only one of $R^{9A}$, $R^{10A}$, or $R^{11A}$ has an —OH substituent.

In some embodiments, in the compound of Formula A wherein E is selected to be a moiety of Formula $E^3$, preferably $E^3$ is selected to have the structure of $E^{3a}$:

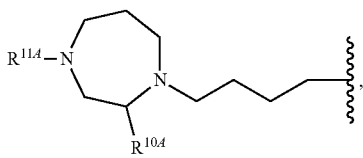

Formula $E^{3a}$ wherein $R^{9A}$, $R^{10A}$, and $R^{11A}$ are as follows:
$R^{10A}$ is —$(CH_2)_{1-2}$—OH and $R^{9A}$ and $R^{11A}$ are all —H; or
$R^{11a}$ is —$CH_2CH_2$—OH and $R^{9A}$ and $R^{10A}$ are all —H; or
one of $R^{9A}$ is —OH, the other of $R^{9A}$ is lower alkyl, and $R^{10A}$ and $R^{11A}$ are all —H.

In some embodiments, in the compound of Formula A wherein E is selected to be a moiety of Formula $E^2$, preferably $E^2$ is selected to have the structure of $E^{2a}$:

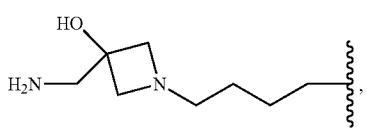

Formula $E^{2a}$

In some embodiments, in the compound of Formula A wherein E is selected to be a moiety of Formula EI, preferably B is:

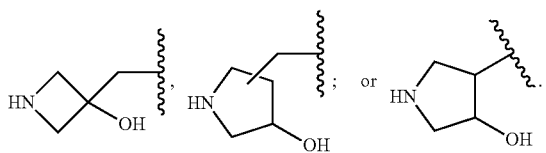

In some embodiments, in the compound of Formula A wherein E is selected to be a moiety of Formula $E^1$, and B is:

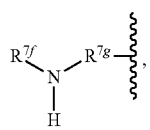

wherein:
(a) $R^{7g}$ is —$(CH_2$—$CH(OH)$—$CH_2$— and $R^{7f}$ is —H or lower alkyl or lower cyclic alkyl; or
(b) $R^{7g}$ is linear alkyl of at least three carbon atoms up to 5 carbon atoms, branched alkyl or cyclic alkyl of up to 6 carbon atoms and $R^{7f}$ is linear, branched, or cyclic alkyl of up to 4 carbon atoms that is substituted on one carbon thereof which is beta or further from the nitrogen with —OH.

In some embodiments, a compound of the invention is preferably a compound of Formula AI:

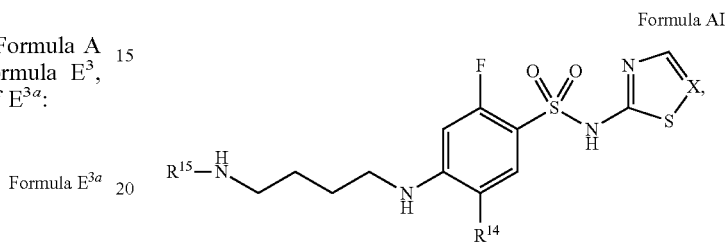

Formula AI wherein:
X is —N= or —$C(R^{14c})$=, wherein $R^{14c}$ is —H, —F, or —$CH_3$;
$R^{14}$ is —Cl or Br; and
$R^{15}$ is a moiety of the Formula AIb bonded to nitrogen via methylene through one of $R^{15b}$, $R^{15c}$, or $R^{15d}$, or bonded directly to nitrogen through $R^{15c}$ if present:

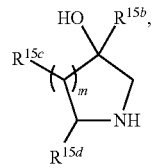

Formula AIb wherein:
m is 0 or 1;
$R^{15c}$, when present and not selected to be bonded to nitrogen is, independently:
(i) —H; or (ii) linear, branched or cyclic alkyl of up to 5 carbon atoms; and
$R^{15b}$ and $R^{15d}$, when not selected to be bonded to nitrogen are, independently:
(i) —H; or (ii) linear, branched or cyclic alkyl of up to 5 carbon atoms.

In some embodiments, in the compound of Formula AI, preferably X is =N—.

In some embodiments, in the compound of Formula AI, preferably $R^{15}$ is:

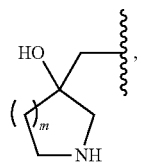

and in some embodiments, preferably "m" is zero.

In some embodiments, a compound of the invention is preferably:

4-[(4-{[(2S)-3-amino-2-hydroxypropyl]amino}butyl)
amino]-5-chloro-2-fluoro-N-1,2,4-thiadiazol-5-ylbenzenesulfonamide;

4-[(4-{[3-amino-2-hydroxypropyl]amino}butyl)amino]-5-chloro-2-fluoro-N-1,2,4-thiadiazol-5-ylbenzenesulfonamide;

4-({4-[3-(aminomethyl)-3-hydroxyazetidin-1-yl]butyl}amino)-5-chloro-2-fluoro-N-(5-fluoro-1,3-thiazol-2-yl)benzenesulfonamide;

4-({4-[3-(aminomethyl)-3-hydroxyazetidin-1-yl]butyl}amino)-5-chloro-2-fluoro-N-1,2,4-thiadiazol-5-yl-benzenesulfonamide;

2-fluoro-N-(5-fluoro-1,3-thiazol-2-yl)-4-[(4-{[(3-hydroxyazetidin-3-yl)methyl]amino}butyl)amino]-5-methylbenzenesulfonamide;

5-bromo-2-fluoro-4-[(4-{[(3-hydroxyazetidin-3-yl)methyl]amino}butyl)amino]-N-1,2,4-thiadiazol-5-ylbenzenesulfonamide;

4-[(4-{[(2R)-3-amino-2-hydroxypropyl]-amino}butyl)amino]-5-chloro-2-fluoro-N-1,2,4-thiadiazol-5-yl-benzenesulfonamide;

4-[(4-{[(2S)-3-amino-2-hydroxypropyl]-amino}butyl)amino]-5-bromo-2-fluoro-N-1,2,4-thiadiazol-5-yl-benzenesulfonamide;

4-[(4-{[(2R)-3-amino-2-hydroxypropyl]-amino}-butyl)amino]-5-bromo-2-fluoro-N-1,2,4-thiadiazol-5-yl-benzenesulfonamide;

4-[(4-{[3-amino-2-hydroxypropyl]-amino}-butyl)amino]-5-bromo-2-fluoro-N-1,2,4-thiadiazol-5-yl-benzenesulfonamide;

5-chloro-2-fluoro-4-[(4-{[(3-hydroxyazetidin-3-yl)methyl]amino}butyl)amino]-N-(4-methyl-1,3-thiazol-2-yl)-benzenesulfonamide;

5-chloro-2-fluoro-4-[(4-{[(3-hydroxyazetidin-3-yl)methyl]amino}butyl)amino]-N-1,2,4-thiadiazol-5-ylbenzenesulfonamide;

5-chloro-2-fluoro-4-[(4-{[(3R,4R)-4-hydroxypyrrolidin-3-yl]amino}butyl)amino]-N-1,2,4-thiadiazol-5-ylbenzenesulfonamide;

5-chloro-2-fluoro-4-{[4-({3-[(2-hydroxyethyl)amino]propyl}amino)butyl]amino}-N-1,2,4-thiadiazol-5-ylbenzenesulfonamide;

5-chloro-2-fluoro-4-{[4-({2-[(2-hydroxyethyl)amino]ethyl}amino)butyl]amino}-N-1,2,4-thiadiazol-5-ylbenzenesulfonamide;

4-({4-[(3-amino-2-hydroxypropyl)amino]butyl}amino)-5-chloro-2-fluoro-N-1,2,4-thiadiazol-5-ylbenzenesulfonamide;

5-chloro-2-fluoro-N-(5-fluoro-1,3-thiazol-2-yl)-4-[(4-{[(3-hydroxyazetidin-3-yl)-methyl]amino}butyl)amino]benzenesulfonamide;

5-chloro-2-fluoro-4-[(4-{[(3S,4S)-4-hydroxypyrrolidin-3-yl]amino}butyl)amino]-N-1,2,4-thiadiazol-5-ylbenzenesulfonamide;

5-chloro-2-fluoro-N-(5-fluoro-1,3-thiazol-2-yl)-4-{[4-({2-[(2-hydroxy-1,1-dimethylethyl)-amino]-1,1-dimethylethyl}amino)butyl]amino}benzenesulfonamide;

5-chloro-2-fluoro-N-(5-fluoro-1,3-thiazol-2-yl)-4-{[4-({2-[(2-hydroxyethyl)amino]-ethyl}amino)butyl]amino}benzenesulfonamide;

4-({4-[(3-amino-2-hydroxypropyl)amino]butyl}amino)-5-chloro-2-fluoro-N-(5-fluoro-1,3-thiazol-2-yl)benzenesulfonamide;

5-chloro-2-fluoro-4-({4-[7-(hydroxymethyl)-1,4-diazepan-1-yl]butyl}amino)-N-1,3-thiazol-2-ylbenzenesulfonamide;

5-chloro-2-fluoro-4-({4-[2-(2-hydroxyethyl)-1,4-diazepan-1-yl]butyl}amino)-N-1,3-thiazol-2-ylbenzenesulfonamide;

5-chloro-2-fluoro-4-({4-[2-(hydroxymethyl)-1,4-diazepan-1-yl]butyl}amino)-N-1,3-thiazol-2-ylbenzenesulfonamide;

5-chloro-2-fluoro-4-{[4-(6-hydroxy-6-methyl-1,4-diazepan-1-yl)butyl]amino}-N-1,3-thiazol-2-ylbenzenesulfonamide;

5-chloro-2-fluoro-4-({4-[4-(2-hydroxyethyl)-1,4-diazepan-1-yl]butyl}amino)-N-1,3-thiazol-2-ylbenzenesulfonamide;

5-chloro-2-fluoro-N-(5-fluoro-1,3-thiazol-2-yl)-4-[(4-{[(3S,4S)-4-hydroxypyrrolidin-3-yl]amino}butyl)amino]benzenesulfonamide;

4-[(4-{[(2R)-3-amino-2-hydroxypropyl]amino}butyl)amino]-5-chloro-2-fluoro-N-(5-fluoro-1,3-thiazol-2-yl)benzenesulfonamide;

4-[(4-{[(2S)-3-amino-2-hydroxypropyl]amino}butyl)amino]-5-chloro-2-fluoro-N-(5-fluoro-1,3-thiazol-2-yl)benzenesulfonamide;

4-(4-{[3-amino-2-hydroxypropyl]amino}butyl)amino]-5-chloro-2-fluoro-N-(5-fluoro-1,3-thiazol-2-yl)benzenesulfonamide;

5-chloro-2-fluoro-4-[(4-{[(3R,4S)-4-hydroxypyrrolidin-3-yl]amino}butyl)amino]-N-1,2,4-thiadiazol-5-ylbenzenesulfonamide;

5-chloro-2-fluoro-N-(5-fluoro-1,3-thiazol-2-yl)-4-[(4-{[(3R,4R)-4-hydroxypyrrolidin-3-yl]amino}butyl)amino]benzenesulfonamide;

5-chloro-2-fluoro-N-(5-fluoro-1,3-thiazol-2-yl)-4-{[4-({[(2S,4S)-4-hydroxypyrrolidin-2-yl]methyl}amino)butyl]amino}benzenesulfonamide;

5-chloro-2-fluoro-N-(5-fluoro-1,3-thiazol-2-yl)-4-{[4-({[(2S,4R)-4-hydroxypyrrolidin-2-yl]methyl}amino)butyl]amino}benzenesulfonamide;

5-chloro-2-fluoro-N-(5-fluoro-1,3-thiazol-2-yl)-4-{[4-({[(2R,4R)-4-hydroxypyrrolidin-2-yl]methyl}amino)butyl]amino}benzenesulfonamide;

5-chloro-2-fluoro-N-(5-fluoro-1,3-thiazol-2-yl)-4-{[4-({[(2R,4S)-4-hydroxypyrrolidin-2-yl]methyl}amino)butyl]amino}benzenesulfonamide;

5-bromo-2-fluoro-N-(5-fluoro-1,3-thiazol-2-yl)-4-[(4-{[(3-hydroxyazetidin-3-yl)methyl]amino}butyl)amino]benzenesulfonamide;

5-chloro-2-fluoro-4-[(4-[(3R,4R)-4-hydroxypyrrolidin-3-yl]amino}butyl)amino]-N-1,2,4-thiadiazol-5-ylbenzenesulfonamide;

4-({4-[(3-amino-2-hydroxypropyl)amino]butyl}amino)-5-chloro-2-fluoro-N-1,3-thiazol-2-ylbenzenesulfonamide;

5-chloro-2-fluoro-4-[(4-[(3-hydroxyazetidin-3-yl)methyl]amino}butyl)amino]-N-1,3-thiazol-2-ylbenzenesulfonamide;

4-[(4-1[(2R)-3-amino-2-hydroxypropyl]amino}butyl)amino]-5-chloro-2-fluoro-N-1,3-thiazol-2-ylbenzenesulfonamide;

4-[(4-{[(2S)-3-amino-2-hydroxypropyl]amino}butyl)amino]-5-chloro-2-fluoro-N-1,3-thiazol-2-ylbenzenesulfonamide;

4-[(4-{[3-amino-2-hydroxypropyl]amino}butyl)amino]-5-chloro-2-fluoro-N-1,3-thiazol-2-ylbenzenesulfonamide;

5-chloro-2-fluoro-4-[(4-[(3R,4R)-4-hydroxypyrrolidin-3-yl]amino}butyl)amino]-N-1,3-thiazol-2-ylbenzenesulfonamide;

4-[(4-{[(1S)-3-amino-1-(hydroxymethyl)propyl]amino}butyl)amino]-5-chloro-2-fluoro-N-1,3-thiazol-2-ylbenzenesulfonamide;

4-[(4-{[(1S)-3-amino-1-(hydroxymethyl)propyl]
amino}butyl)amino]-5-chloro-2-fluoro-N-(5-fluoro-1,3-
thiazol-2-yl)benzenesulfonamide;
4-[(4-{[(1S)-3-amino-1-(hydroxymethyl)propyl]
amino}butyl)amino]-5-chloro-2-fluoro-N-1,2,4-thiadi-
azol-5-ylbenzenesulfonamide;
4-[(4-{[(1S)-2-amino-1-(hydroxymethyl)ethyl]
amino}butyl)amino]-5-chloro-2-fluoro-N-1,3-thiazol-2-
ylbenzenesulfonamide;
4-[(4-{[(1S)-2-amino-1-(hydroxymethyl)ethyl]
amino}butyl)amino]-5-chloro-2-fluoro-N-(5-fluoro-1,3-
thiazol-2-yl)benzenesulfonamide;
4-[(4-{[(1S)-2-amino-1-(hydroxymethyl)ethyl]
amino}butyl)amino]-5-chloro-2-fluoro-N-1,2,4-thiadi-
azol-5-ylbenzenesulfonamide;
5-chloro-2-fluoro-4-[(4-{[(3S,4S)-4-hydroxypyrrolidin-3-
yl]amino}butyl)amino]-N-1,3-thiazol-2-ylbenzenesulfo-
namide;
4-[(4-{[(1R)-2-amino-1-(hydroxymethyl)ethyl]
amino}butyl)amino]-5-chloro-2-fluoro-N-1,3-thiazol-2-
ylbenzenesulfonamide;
4-[(4-{[(1R)-2-amino-1-(hydroxymethyl)ethyl]
amino}butyl)amino]-5-chloro-2-fluoro-N-(5-fluoro-1,3-
thiazol-2-yl)benzenesulfonamide;
5-bromo-2-fluoro-4-((4-(6-hydroxy-1,4-diazepan-1-yl)bu-
tyl)amino)-N-(1,2,4-thiadiazol-5-yl)benzenesulfonamide;
5-bromo-2-fluoro-4-((4-(((3S,4S)-4-hydroxypyrrolidin-3-
yl)amino)butyl)amino)-N-(1,2,4-thiadiazol-5-yl)benze-
nesulfonamide;
5-bromo-2-fluoro-4-((4-(((3R,4R)-4-hydroxypyrrolidin-3-
yl)amino)butyl)amino)-N-(1,2,4-thiadiazol-5-yl)benze-
nesulfonamide;
4-((4-(3-(aminomethyl)-3-hydroxyazetidin-1-yl)butyl)
amino)-5-bromo-2-fluoro-N-(1,2,4-thiadiazol-5-yl)ben-
zenesulfonamide;
4-[(4-{[(1R)-2-amino-1-(hydroxymethyl)ethyl]
amino}butyl)amino]-5-chloro-2-fluoro-N-1,2,4-thiadi-
azol-5-ylbenzenesulfonamide; or
5-chloro-2-fluoro-4-[(4-{[(4-hydroxy-4-methylpyrrolidin-
2-yl)methyl]amino}butyl)amino]-N-1,3-thiazol-2-ylben-
zenesulfonamide,
or a pharmaceutically acceptable salt of any thereof.

In one aspect the invention provides a pharmaceutical composition comprising at least one compound of Formula A, or a salt thereof, and at least one pharmaceutically acceptable excipient adapted for administration to a patient via any pharmaceutically acceptable route, including dosage forms for oral, intravenous, infusion, subcutaneous, trans-cutaneous, intramuscular, intradermal, transmucosal, or intramucosal routes of administration.

In one aspect this invention provides also a pharmaceutical composition comprising a pharmaceutical carrier, an effective amount of at least one compound of Formula A, or a salt thereof, an effective amount of at least one other pharmaceutically active ingredient which is: (i) an opioid agonist or antagonist; (ii) a calcium channel antagonist; (iii) an NMDA receptor agonist or antagonist; (iv) a COX-2 selective inhibitor; (v) an NSAID (non-steroidal anti-inflammatory drug); or (vi) paracetamol (APAP, acetaminophen), and a pharmaceutically acceptable carrier.

In one aspect the invention provides also a method of treatment, management, alleviation or amelioration of conditions or disease states which can be treated, managed, alleviated or ameliorated by specific inhibition of Nav 1.7 channel activity, the method comprising administering to a patient in need thereof a composition comprising at least one compound of Formula A, or a salt thereof, in an amount providing a serum level of at least one said compound sufficient to effect said treatment, management, alleviation or amelioration of said conditions or disease states. In some embodiments, preferably the condition or disease state to be treated, managed, alleviated or ameliorated is acute pain or a chronic pain disorder. In some embodiments, preferably the condition is acute pain.

DETAILED DESCRIPTION OF THE INVENTION

As mentioned above, the invention provides compounds believed to have selective activity as $Na_v$ 1.7 sodium ion channel inhibitors which have the structure of Formula A, or a salt thereof:

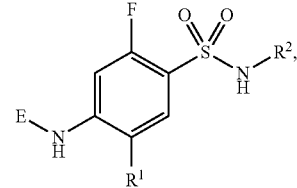

Formula A wherein $R^1$, $R^2$, and E are defined herein.

Preferred compounds of the invention exhibit a potency ($IC_{50}$) of less than about 500 nanomolar when assayed in accordance with IonWorks® assay technique described herein, and exhibit at least 50-fold selectivity for $Na_v$ 1.7 sodium channels over $Na_v$ 1.5 sodium channels, more preferably at least 500-fold selectivity for $Na_v$ 1.7 sodium channels over $Na_v$ 1.5 sodium channels when functional potency for each channel are compared using the IonWorks® assay technique described herein.

Compounds of the invention and formulations comprising compounds of the invention are believed to be useful in providing treatment, management, alleviation or amelioration of conditions or disease states which can be treated, managed, alleviated or ameliorated by specific inhibiting of Nav 1.7 channel activity. Examples of disease states which are believed to be desirably affected using such therapy include, but are not limited to, inhibiting acute pain, peri-operative, post-operative and neuropathic pain, for example, postherpetic neuralgia, trigeminal neuralgia, diabetic neuropathy, chronic lower back pain, phantom limb pain, pain resulting from cancer and chemotherapy, chronic pelvic pain, complex regional pain syndrome and related neuralgias, pruritis or cough.

As described herein, unless otherwise indicated, the use of a compound in treatment means that an amount of the compound, generally presented as a component of a formulation that comprises other excipients, is administered in aliquots of an amount, and at time intervals, which provides and maintains at least a therapeutic serum level of at least one pharmaceutically active form of the compound over the time interval between dose administration.

Absolute stereochemistry is illustrated by the use of hashed and solid wedge bonds. As shown in Illus-I and Illus-II. Accordingly, the methyl group of Illus-I is emerging from the page of the paper and the ethyl group in Illus-II is descending into the page, where the cyclohexene ring resides within the plane of the paper. It is assumed that the hydrogen on the same carbon as the methyl group of Illus-I descends into the page and the hydrogen on the same carbon as the ethyl group of Illus-II emerges from the page. The convention is the same where both a hashed and solid rectangle are appended to the same carbon as in Illus-III, the Methyl group is emerging from the plane of the paper and the ethyl group is descending into the plane of the paper with the cyclohexene ring in the plane of the paper.

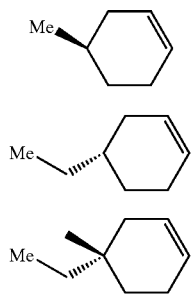

Illus-1

Illus-2

Illus-3

As is conventional, unless otherwise noted in accompanying text, ordinary "stick" bonds or "wavy" bonds indicate that all possible stereochemistry is represented, including, pure compounds, mixtures of isomers, and racemic mixtures.

As used herein, unless otherwise specified, the following terms have the following meanings:

The phrase "at least one" used in reference to the number of components comprising a composition, for example, "at least one pharmaceutical excipient" means that one member of the specified group is present in the composition, and more than one may additionally be present. Components of a composition are typically aliquots of isolated pure material added to the composition, where the purity level of the isolated material added into the composition is the normally accepted purity level for a reagent of the type.

"at least one" used in reference to substituents appended to a compound substrate, for example, a halogen or a moiety appended to a portion of a structure replacing a hydrogen, means that one substituent of the group of substituents specified is present, and more than one of said substituents may be bonded to any of the defined or chemically accessible bonding points of the substrate.

Whether used in reference to a substituent on a compound or a component of a pharmaceutical composition the phrase "one or more", means the same as "at least one";

"concurrently" and "contemporaneously" both include in their meaning (1) simultaneously in time (e.g., at the same time); and (2) at different times but within the course of a common treatment schedule;

"consecutively" means one following the other;

"sequentially" refers to a series administration of therapeutic agents that awaits a period of efficacy to transpire between administering each additional agent; this is to say that after administration of one component, the next component is administered after an effective time period after the first component; the effective time period is the amount of time given for realization of a benefit from the administration of the first component;

"effective amount" or "therapeutically effective amount" is meant to describe the provision of an amount of at least one compound of the invention or of a composition comprising at least one compound of the invention which is effective in treating or inhibiting a disease or condition described herein, and thus produce the desired therapeutic, ameliorative, inhibitory or preventative effect. For example, in treating central nervous system diseases or disorders with one or more of the compounds described herein "effective amount" (or "therapeutically effective amount") means, for example, providing the amount of at least one compound of Formula A that results in a therapeutic response in a patient afflicted with a central nervous system disease or disorder ("condition"), including a response suitable to manage, alleviate, ameliorate, or treat the condition or alleviate, ameliorate, reduce, or eradicate one or more symptoms attributed to the condition and/or long-term stabilization of the condition, for example, as may be determined by the analysis of pharmacodynamic markers or clinical evaluation of patients afflicted with the condition;

"patient" and "subject" means an animal, such as a mammal (e.g., a human being) and is preferably a human being;

"prodrug" means compounds that are rapidly transformed, for example, by hydrolysis in blood, in vivo to the parent compound, e.g., conversion of a prodrug of Formula A to a compound of Formula A, or to a salt thereof; a thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference; the scope of this invention includes prodrugs of the novel compounds of this invention;

The term "substituted" means that one or more of the enumerated substituents can occupy one or more of the bonding positions on the substrate typically occupied by "H", provided that such substitution does not exceed the normal valency rules for the atom in the bonding configuration presented in the substrate, and that the substitution ultimately provides a stable compound, which is to say that such substitution does not provide compounds with mutually reactive substituents located geminal or vicinal to each other; and wherein the substitution provides a compound sufficiently robust to survive isolation to a useful degree of purity from a reaction mixture.

Where optional substitution of a moiety is described (e.g. "optionally substituted") the term means that if substituents are present, one or more of the enumerated substituents for the specified substrate can be present on the substrate in a bonding position normally occupied by the default substituent normally occupying that position. For example, a default substituent on the carbon atoms of an alkyl moiety is a hydrogen atom, an optional substituent can replace the default substituent.

As used herein, unless otherwise specified, the following terms used to describe moieties, whether comprising the entire definition of a variable portion of a structural representation of a compound of the invention or a substituent appended to a variable portion of a structural representation of a group of compounds of the invention have the following meanings, and unless otherwise specified, the definitions of each term (i.e., moiety or substituent) apply when that term is used individually or as a component of another term (e.g., the definition of aryl is the same for aryl and for the aryl portion of arylalkyl, alkylaryl, arylalkynyl moieties, and the like); moieties are equivalently described herein by structure, typographical representation or chemical terminology without intending any differentiation in meaning, for example, an "acyl" substituent may be equivalently described herein by the term "acyl", by typographical representations "R'—(C=O)—" or "R'—C(O)—", or by a structural representation:

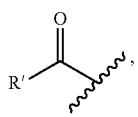

equally, with no differentiation implied using any or all of these representations;

"alkyl" (including the alkyl portions of other moieties, such as trifluoromethyl-alkyl- and alkoxy-) means an aliphatic hydrocarbon moiety comprising up to about 20 carbon atoms (for example, a designation of "$C_{1-20}$-alkyl" indicates an aliphatic hydrocarbon moiety of from 1 to 20 carbon atoms). In some embodiments, alkyls preferably comprise up to about 10 carbon atoms, unless the term is modified by an indication that a shorter chain is contemplated, for example, an alkyl moiety of from 1 up to 8 carbon atoms is designated herein "$C_{1-8}$-alkyl". The term "alkyl" is further defined by "Linear", "Branched" or "Cyclic. Where the term "alkyl" is indicated with two hyphens (i.e., "-alkyl-" it indicates that the alkyl moiety is bonded in a manner that the alkyl moiety connects the substituents on either side of it, for example, "-alkyl-OH" indicates an alkyl moiety connecting a hydroxyl moiety to a substrate.

The term "linear-alkyl" includes alkyl moieties which comprise a hydrocarbon chain with no aliphatic hydrocarbon "branches" appended to it, although other substituents may replace a C—H bond on the hydrocarbon chain. Examples of linear alkyl include, but are not limited to, methyl-, ethyl-, n-propyl-, n-butyl-, n-pentyl- or n-hexyl-.

The term "branched-alkyl" is a moiety comprising a main hydrocarbon chain of up to the maximum specified number of carbon atoms with a lower-alkyl chain appended to one or more of the carbon atoms comprising, but not terminating, the main hydrocarbon chain. A branched alkyl moiety therefore comprises at least 3 carbon atoms in the main chain. Examples of branched alkyl moieties include, but are not limited to, t-butyl-, neopentyl-, or 2-methyl-4-ethyl-hexyl- The term "cyclic-alkyl" (equivalently "cycloalkyl") means a moiety having a main hydrocarbon chain forming a mono- or bicyclo-cyclic aliphatic moiety comprising at least 3 carbon atoms (the minimum number necessary to provide a monocyclic moiety) up to the maximum number of specified carbon atoms, generally 8 for a monocyclic moiety and 10 for a bicyclic moiety. Examples of cycloalkyl moieties include, but are not limited to, cyclopropyl, cyclobutyl, cyclopentyl or cyclohexyl. The term cyclic-alkyl (equivalently "cycloalkyl") also includes non-aromatic, fused multicyclic ring system comprising up to 20 carbon atoms which may optionally be substituted as defined herein for "alkyl" generally. Suitable multicyclic cycloalkyls are, for example, but are not limited to: 1-decalin; norbornyl; adamantly; and the like;

The term "lower cyclic alkyl" means a cycloalkyl comprising less than 6 carbon atoms, e.g., cyclopropyl, cyclobutyl, cyclopentyl, cyclohexyl;

As used herein, when the term "alkyl" is modified by "substituted" or "optionally substituted", it means that one or more C—H bonds in the alkyl moiety group is substituted, or optionally may be substituted, by a substituent bonded to the alkyl substrate which is called out in defining the moiety.

"lower alkyl" means a linear, or branched alkyl moiety comprising up to 6 carbon atoms; non-limiting examples of suitable lower alkyl groups include methyl, ethyl, n-propyl, isopropyl, n-butyl, t-butyl, n-pentyl, isopentyl, neopentyl, n-hexyl, and the like;

where a structural formula represents bonding between a moiety and a substrate using a the bonding line that terminates in the middle of the structure, for example the following representations:

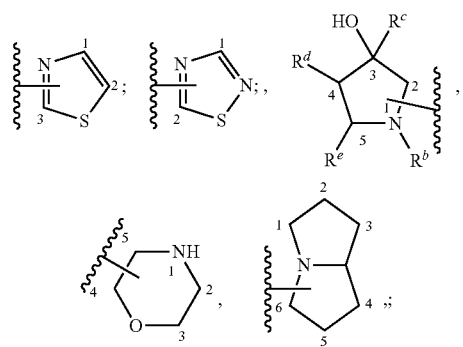

whether or not numbered the structure indicates that unless otherwise defined the moiety may be bonded to the substrate through any of available ring atom, for example, the numbered atoms of the example moieties;

"heterocyclyl" (or heterocycloalkyl) means a non-aromatic saturated monocyclic or multicyclic ring system comprising 3 to 10 ring atoms, preferably 5 to 10 ring atoms, in which one or more of the atoms in the ring system is an element other than carbon, for example nitrogen (e.g. piperidyl- or pyrrolidinyl), oxygen (e.g. furanyl and tetrahydropyranyl) or sulfur (e.g. tetrahydrothiophenyl and tetrahydrothiopyranyl); and wherein the heteroatoms can be alone or in combination provided that the moiety does not contain adjacent oxygen and/or sulfur atoms present in the ring system; preferred heterocyclyl moieties contain 5 to 6 ring atoms; the prefix aza, oxa or thia before the heterocyclyl root name means that at least one nitrogen, oxygen or sulfur atom, respectively, is present as a ring atom; the heterocyclyl can be optionally substituted by one or more independently selected substituents;

the nitrogen or sulfur atom of the heterocyclyl can be optionally oxidized to the corresponding N-oxide, S-oxide or S,S-dioxide ($SO_2$); non-limiting examples of suitable monocyclic heterocyclyl rings include piperidyl, pyrrolidinyl, piperazinyl, morpholinyl—

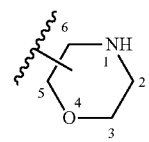

(where unless otherwise noted the moiety is bonded to the substrate through any of ring carbon atoms C2, C3, C5, or C6), thiomorpholinyl, thiazolidinyl, 1,3-dioxolanyl, 1,4-dioxanyl, tetrahydrofuranyl, tetrahydrothiophenyl, tetrahydrothiopyranyl, and the like; and polycyclicheterocyclyl compounds, for example, moieties of the structure:

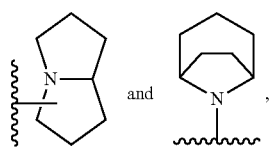

and the like.

"halogen" means fluorine, chlorine, bromine, or iodine; preferred halogens, unless specified otherwise where the term is used, are fluorine, chlorine and bromine, a substituent which is a halogen atom means —F, —Cl, —Br, or —I, and "halo" means fluoro, chloro, bromo, or iodo substituents bonded to the moiety defined, for example, "haloalkyl" means an alkyl, as defined above, wherein one or more of the bonding positions on the alkyl moiety typically occupied by hydrogen atoms are instead occupied by a halo group, perhaloalkyl (or "fully halogenated" alkyl) means that all bonding positions not participating in bonding the alkyl substituent to a substrate are occupied by a halogen, for example, where the alkyl is selected to be methyl, the term perfluoroalkyl means —CF$_3$;

"hydroxyl" and "hydroxy" means an HO— group, "hydroxyalkyl" means a substituent of the formula: "HO-alkyl-", wherein the alkyl group is bonded to the substrate and may be substituted or unsubstituted as defined above; preferred hydroxyalkyl moieties comprise a lower alkyl; Non-limiting examples of suitable hydroxyalkyl groups include hydroxymethyl and 2-hydroxyethyl; and bonding sequence is indicated by hyphens where moieties are represented in text, for example alkyl, indicates a single bond between a substrate and an alkyl moiety, -alkyl-X, indicates that an alkyl group bonds an "X" substituent to a substrate, and in structural representation, bonding sequence is indicated by a wavy line terminating a bond representation, for example:

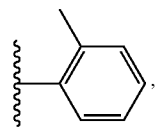 [SMILES: *c1ccccc1C]

indicates that the methylphenyl moiety is bonded to a substrate through a carbon atom ortho to the methyl substituent, while a bond representation terminated with a wavy line and drawn into a structure without any particular indication of an atom to which it is bonded indicates that the moiety may be bonded to a substrate via any of the atoms in the moiety which are available for bonding as described in the examples above.

Unsatisfied valences in the text, schemes, examples, structural formulae, and any Tables herein is assumed to have a hydrogen atom or atoms of sufficient number to satisfy the valences.

One or more compounds of the invention may also exist as, or optionally be converted to, a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, and hemisolvate, including hydrates (where the solvent is water or aqueous-based) and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (for example, an organic solvent, an aqueous solvent, water or mixtures of two or more thereof) at a higher than ambient temperature, and cooling the solution, with or without an antisolvent present, at a rate sufficient to form crystals which are then isolated by standard methods. Analytical techniques such as, for example I.R. spectroscopy, show the presence of the solvent (including water) in the crystals as a solvate (or hydrate in the case where water is incorporated into the crystalline form).

This invention also includes the compounds of this invention in isolated and purified form obtained by routine techniques. Polymorphic forms of the compounds of Formula A, and of the salts, solvates and prodrugs of the compounds of Formula A, are intended to be included in the present invention. Certain compounds of the invention may exist in different isomeric forms (e.g., enantiomers, diastereoisomers, atropisomers). The inventive compounds include all isomeric forms thereof, both in pure form and admixtures of two or more, including racemic mixtures.

In the same manner, unless indicated otherwise, presenting a structural representation of any tautomeric form of a compound which exhibits tautomerism is meant to include all such tautomeric forms of the compound. Accordingly, where compounds of the invention, their salts, and solvates and prodrugs thereof, may exist in different tautomeric forms or in equilibrium among such forms, all such forms of the compound are embraced by, and included within the scope of the invention. Examples of such tautomers include, but are not limited to, ketone/enol tautomeric forms, imine-enamine tautomeric forms, and for example heteroaromatic forms such as the following moieties:

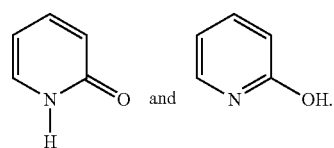 [SMILES: O=c1cccc[nH]1 ; Oc1ccccn1]

In particular, compounds of the invention are presented herein having a portion of their structure represented by the structural drawing A is contemplated as being equivalent to tautomeric form B:

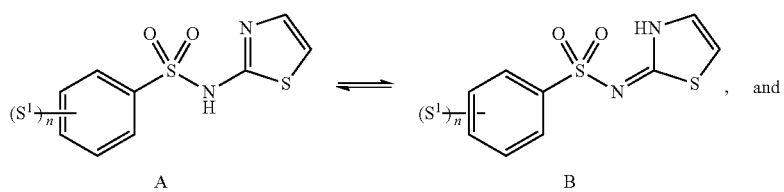

-continued

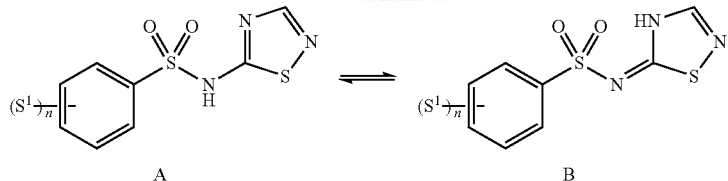

where (S1)n is one to five substituents on the aryl ring, thus, any structural drawing representation where tautomerism is possible is intended to include all tautomeric forms within the scope of the structures represented thereby.

Oxygen and nitrogen atoms in a structure may be represented equivalently as protonated on a lone pair of electrons or in unprotonated form, and both forms are contemplated where either structure is presented, for example, the protonated form A and unprotonated form B of the amine illustrated below:

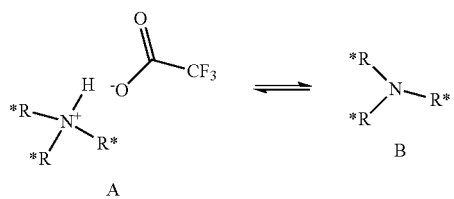

All stereoisomers of the compounds of the invention (including salts and solvates of the inventive compounds and their prodrugs), such as those which may exist due to asymmetric carbons present in a compound of the invention, and including enantiomeric forms (which may exist even in the absence of asymmetric carbons), rotameric forms, atropisomers, and diastereomeric forms, are contemplated within the scope of this invention. Individual stereoisomers of the compounds of the invention may be isolated in a pure form, for example, substantially free of other isomers, or may be isolated as an admixture of two or more stereoisomers or as a racemate. The chiral centers of the present invention can have the S or R configuration as defined by the IUPAC 1974 Recommendations. The use of the terms "salt", "solvate" "prodrug" and the like, is intended to equally apply to salts, solvates and prodrugs of isolated enantiomers, stereoisomer pairs or groups, rotamers, tautomers, or racemates of the inventive compounds.

Where diastereomeric mixtures can be separated into their individual diastereomers on the basis of their physical chemical differences by known methods, for example, by chiral chromatography and/or fractional crystallization, simple structural representation of the compound contemplates all diastereomers of the compound. As is known, enantiomers may also be separated by converting the enantiomeric mixture into a diasteromeric mixture by reaction with an appropriate optically active compound (e.g., chiral auxiliary such as a chiral alcohol or Mosher's acid chloride), separating the diastereomers and converting (e.g., hydrolyzing) the individually isolated diastereomers to the corresponding purified enantiomers.

As the term is employed herein, salts of the inventive compounds, whether acidic salts formed with inorganic and/or organic acids, basic salts formed with inorganic and/or organic bases, salts formed which include zwitterionic character, for example, where a compound contains both a basic moiety, for example, but not limited to, a nitrogen atom, for example, an amine, pyridine or imidazole, and an acidic moiety, for example, but not limited to a carboxylic acid, are included in the scope of the inventive compounds described herein. The formation of pharmaceutically useful salts from basic (or acidic) pharmaceutical compounds are discussed, for example, by S. Berge et al., Journal of Pharmaceutical Sciences (1977) 66(1) 1-19; P. Gould, International J. of Pharmaceutics (1986) 33 201-217; Anderson et al, The Practice of Medicinal Chemistry (1996), Academic Press, New York; in The Orange Book (Food & Drug Administration, Washington, D.C. on their website); and P. Heinrich Stahl, Camille G. Wermuth (Eds.), Handbook of Pharmaceutical Salts: Properties, Selection, and Use, (2002) Int'l. Union of Pure and Applied Chemistry, pp. 330-331. These disclosures are incorporated herein by reference.

The present invention contemplates all available salts, including salts which are generally recognized as safe for use in preparing pharmaceutical formulations and those which may be formed presently within the ordinary skill in the art and are later classified as being "generally recognized as safe" for use in the preparation of pharmaceutical formulations, termed herein as "pharmaceutically acceptable salts". Examples of pharmaceutically acceptable acid addition salts include, but are not limited to, acetates, including trifluoroacetate salts, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, methyl sulfates, 2-naphthalenesulfonates, nicotinates, nitrates, oxalates, pamoates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates,) undecanoates, and the like.

Examples of pharmaceutically acceptable basic salts include, but are not limited to, ammonium salts, alkali metal salts such as sodium, lithium, and potassium salts, alkaline earth metal salts such as calcium and magnesium salts, aluminum salts, zinc salts, salts with organic bases (for example, organic amines) such as benzathines, diethylamine, dicyclohexylamines, hydrabamines (formed with N,N-bis(dehydroabietyl)ethylenediamine), N-methyl-D-glucamines, N-methyl-D-glucamides, t-butyl amines, piperazine, phenylcyclohexyl-amine, choline, tromethamine, and salts with amino acids such as arginine, lysine and the like. Basic nitrogen-containing groups may be converted to an ammonium ion or quarternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

In general, salts of compounds are intended to be pharmaceutically acceptable salts within the scope of the invention and all acid and base salts are considered equivalent to the free forms of the corresponding compounds for purposes of the invention. Many of the compounds exemplified herein are isolated in the form of a salt, for example, a hydrochloride, acetate trifluoroacetata, formate, or triflate salt. As described in the Examples, herein, such salts may readily be converted to the free-base form of the compound by elution from an appropriate media using an appropriate base solution followed by chromatographic separation on a column of appropriate polarity.

The term "purified", "in purified form" or "in isolated and purified form" for a compound refers to the physical state of said compound after being isolated from a synthetic process or natural source or combination thereof. Thus, the term "purified", "in purified form" or "in isolated and purified form" for a compound refers to the physical state of said compound after being obtained from a purification process or processes described herein or well known to the skilled artisan, and in sufficient purity to be characterized by standard analytical techniques described herein or well known to the skilled artisan.

A functional group in a compound termed "protected" means that the group is in modified form to preclude undesired side reactions at the protected site when the compound is subjected to a reaction. Suitable protecting groups are known, for example, as by reference to standard textbooks, for example, T. W. Greene et al, Protective Groups in organic Synthesis (1991), Wiley, New York.

When a variable (e.g., aryl, heterocycl, $R^{XY}$, etc.) appears more than once in any moiety or in any compound of the invention, the selection of moieties defining that variable for each occurrence is independent of its definition at every other occurrence unless specified otherwise in the local variable definition.

The present invention also embraces isotopically-labeled compounds of the present invention which are structurally identical to those recited herein, but for the fact that a statistically significant percentage of one or more atoms in that form of the compound are replaced by an atom having an atomic mass or mass number different from the atomic mass or mass number of the most abundant isotope usually found in nature, thus altering the naturally occurring abundance of that isotope present in a compound of the invention. Examples of isotopes that can be preferentially incorporated into compounds of the invention include isotopes of hydrogen, carbon, nitrogen, oxygen, phosphorus, iodine, fluorine and chlorine, for example, but not limited to: $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, and $^{36}Cl$, $^{123}I$ and $^{125}I$. It will be appreciated that other isotopes may be incorporated by know means also.

Certain isotopically-labeled compounds of the invention (e.g., those labeled with $^{3}H$, $^{11}C$ and $^{14}C$) are recognized as being particularly useful in compound and/or substrate tissue distribution assays using a variety of known techniques. Tritiated (i.e., $^{3}H$) and carbon-14 (i.e., $^{14}C$) isotopes are particularly preferred for their ease of preparation and detection. Further, substitution of a naturally abundant isotope with a heavier isotope, for example, substitution of protium with deuterium (i.e., $^{2}H$) may afford certain therapeutic advantages resulting from greater metabolic stability (e.g., increased in vivo half-life or reduced dosage requirements) and hence may be preferred in some circumstances.

Isotopically labeled compounds of the invention can generally be prepared by following procedures analogous to those disclosed in the reaction Schemes and/or in the Examples herein below, by substituting an appropriate isotopically labeled reagent for a non-isotopically labeled reagent, or by well-known reactions of an appropriately prepared precursor to the compound of the invention which is specifically prepared for such a "labeling" reaction. Such compounds are included also in the present invention.

As used herein, the term "pharmaceutical composition" comprises at least one pharmaceutically active compound and at least one excipient, and is intended to encompass both the combination of the specified ingredients in the specified amounts, and any product which results, directly or indirectly, from combination of the specified ingredients in the specified amounts. As will be appreciated by the ordinarily skilled artisan, excipients are any constituent which adapts the composition to a particular route of administration or aids the processing of a composition into a dosage form without itself exerting an active pharmaceutical effect. A bulk composition is material that has not yet been formed into individual units for administration As mentioned above, in one aspect the invention provides compositions suitable for use in selectively inhibiting Nav 1.7 sodium channels found in sensory and sympathetic neurons, comprising at least one compound of the invention (as defined herein, for example one or more compounds of Formula A, or a salt thereof) and at least one pharmaceutically acceptable carrier (described below). It will be appreciated that pharmaceutical formulations of the invention may comprise more than one compound of the invention, for example, the combination of two or three compounds of the invention, each present by adding to the formulation the desired amount of the compound in a pharmaceutically acceptably pure form. It will be appreciated that compositions of the invention may comprise, in addition to one or more of the compounds of the invention, one or more additional compounds which also have pharmacological activity, for example, as described herein below. Such formulations are believed to have utility in the treatment, management, amelioration or in providing therapy for diseases or conditions related to pain, for example, acute pain, chronic pain, inflammatory pain, or neuropathic pain disorders, or related to pruritic disorders, or cough disorders.

While compositions of the invention may be employed in bulk form, it will be appreciated that for most applications compositions will be incorporated into a dosage form suitable for administration to a patient, each dosage form comprising an amount of the selected composition which contains an effective amount of said one or more compounds of Formula A. Examples of suitable dosage forms include, but are not limited to, dosage forms adapted for: (i) intravenous (IV) infusion, for example, over a prolonged period using an I.V. infusion pump; (ii) a dosage form adapted for intramuscular administration (IM), for example, an injectable solution or suspension, and which may be adapted to form a depot having extended release properties; (iii) a dosage form adapted for drip intravenous administration (IV), for example, a solution or suspension, for example, as an IV solution or a concentrate to be injected into a saline IV bag; or (iv) a dosage form adapted for subcutaneous administration. Other dosage forms which may be contemplated include, but are not limited to: (i) oral administration, e.g., a liquid, gel, powder, solid or semi-solid pharmaceutical composition which is loaded into a capsule or pressed into a tablet and may comprise additionally one or more coatings which modify its release properties, for example, coatings which impart delayed release or formulations which have extended release properties; (ii) a dosage form adapted for administration through tissues of the oral cavity, for example, a rapidly dissolving tablet, a lozenge, a solution, a gel, a sachets or a needle array suitable for providing intramucosal administration; (iii) a dosage form adapted for administration via the mucosa of the nasal or upper respiratory cavity, for example a solution, suspension or emulsion formulation for dispersion in the nose or airway; (iv) a dosage form adapted for transdermal administration, for example, a patch, cream or gel; (v) a dosage form adapted for intradermal administration, for example, a microneedle array; and (vi) a dosage form adapted for delivery via rectal or vaginal mucosa, for example, a suppository.

For preparing pharmaceutical compositions containing compounds of the invention, generally the compounds of the invention will be combined with one or more pharmaceutically acceptable excipients. These excipients impart to the composition properties which make it easier to handle or process, for example, lubricants or pressing aids in powdered medicaments intended to be tableted, or for example, solution stabilizing or emulsifying agents which may adapt the formulation to a desired route of administration, for example, which provide a formulation for injection, for example, intramuscular or intravenous routes of administration or administration via IV or diffusion pump infusion or other form parenteral administration, or for oral administration, for example, via absorption from the gastrointestinal tract, or for transdermal or transmucosal administration, for example, via adhesive skin "patch" or buccal administration. These excipients are collectively termed herein "a carrier". Typically formulations may comprise up to about 95 percent active ingredient, although formulations with greater amounts may be prepared.

Pharmaceutical compositions can be solid, semi-solid or liquid. Solid form preparations can be adapted to a variety of modes of administration, examples of which include, but are not limited to, powders, dispersible granules, mini-tablets, beads, which can be used, for example, for tableting, encapsulation, or direct administration. Liquid form preparations include, but are not limited to, solutions, suspensions and emulsions which for example, but not exclusively, can be employed in the preparation of formulations intended for intravenous administration (IV), for example, but not limited to, administration via drip IV or infusion pump, intramuscular injection (IM), for example, of a bolus which is released over an extended duration, direct IV injection, or adapted to subcutaneous routes of administration. Other routes of administration which may be contemplated include intranasal administration, or for administration to some other mucosal membrane. Formulations prepared for administration to various mucosal membranes may also include additional components adapting them for such administration, for example, viscosity modifiers.

Although in some embodiments, compositions suitable for use in an IV administration, for example, IV drip or infusion pump or injection, or for subcutaneous routes of administration are preferable, a composition of the invention may be formulated for administration via other routes. Examples include Aerosol preparations, for example, suitable for administration via inhalation or via nasal mucosa, may include solutions and solids in powder form, which may be in combination with a pharmaceutically acceptable propellant, for example, an inert compressed gas, e.g. nitrogen. Also included are solid form preparations which are intended to be converted, shortly before use, to a suspension or a solution, for example, for oral or parenteral administration. Examples of such solid forms include, but are not limited to, freeze dried formulations and liquid formulations adsorbed into a solid absorbent medium.

For example, the compounds of the invention may also be deliverable transdermally or transmucosally, for example, from a liquid, suppository, cream, foam, gel, or rapidly dissolving solid form. It will be appreciated that transdermal compositions can take also the form of creams, lotions, aerosols and/or emulsions and can be provided in a unit dosage form which includes a transdermal patch of any know in the art, for example, a patch which incorporates either a matrix comprising the pharmaceutically active compound or a reservoir which comprises a solid or liquid form of the pharmaceutically active compound.

Examples of pharmaceutically acceptable carriers and methods of manufacture for various compositions mentioned above may be found in A. Gennaro (ed.), Remington: The Science and Practice of Pharmacy, $20^{th}$ Edition, (2000), Lippincott Williams & Wilkins, Baltimore, Md.

The actual dosage employed may be varied depending upon the requirements of the patient and the severity of the condition being treated. Determination of the proper dosage regimen for a particular situation is within the skill in the art, for example, as described in the standard literature, for example, as described in the "Physicians' Desk Reference" (PDR), e.g., 1996 edition (Medical Economics Company, Montvale, N.J. 07645-1742, USA), the Physician's Desk Reference, $56^{th}$ Edition, 2002 (published by Medical Economics company, Inc. Montvale, N.J. 07645-1742), or the Physician's Desk Reference, $57^{th}$ Edition, 2003 (published by Thompson PDR, Montvale, N.J. 07645-1742); the disclosures of which is incorporated herein by reference thereto. For convenience, the total daily dosage may be divided and administered in portions during the day as required or delivered continuously.

In another embodiment the present invention is believed to provide for treatment, management, prevention, alleviation or amelioration of conditions or disease states which can be treated, managed, prevented, alleviated or ameliorated by specific inhibition of Nav 1.7 channel activity. Some examples are pain conditions, pruritic conditions and cough conditions. Examples of pain conditions include, but are not limited to, acute pain, perioperative pain, preoperative pain, postoperative pain, neuropathic pain, for example, post herpetic neuralgia, trigeminal neuralgia, diabetic neuropathy, chronic lower back pain, phantom limb pain, chronic pelvic pain, vulvodynia, complex regional pain syndrome and related neuralgias, pain associated with cancer and chemotherapy, pain associated with HIV, and HIV treatment-induced neuropathy, nerve injury, root avulsions, painful traumatic mononeuropathy, painful polyneuropathy, erythromelalgia, paroxysmal extreme pain disorder, small fiber neuropathy, burning mouth syndrome, central pain syndromes (potentially caused by virtually any lesion at any level of the nervous system), postsurgical pain syndromes (e.g., post mastectomy syndrome, post thoracotomy syndrome, stump pain)), bone and joint pain (osteoarthritis), repetitive motion pain, dental pain, myofascial pain (muscular injury, fibromyalgia), perioperative pain (general surgery, gynecological), chronic pain, dysmennorhea, pain associated with angina, inflammatory pain of varied origins (e.g. osteoarthritis, rheumatoid arthritis, rheumatic disease, teno-synovitis and gout), shoulder tendonitis or bursitis, gouty arthritis, and aolymyalgia rheumatica, primary hyperalgesia, secondary hyperalgesia, primary allodynia, secondary allodynia, or other pain caused by central sensitization, complex regional pain syndrome, chronic arthritic pain and related neuralgias acute pain, migraine, migraine headache, headache pain, cluster headache, non-vascular headache, traumatic nerve injury, nerve compression or entrapment, and neuroma pain, pruritic conditions, and cough conditions.

In some embodiments in which it is desired to treat a pain disorder, preferably the disorder is an acute pain, inflammatory pain or neuropathic pain disorder, more preferably an acute pain disorder.

In accordance with the present invention, treatment, alleviation, amelioration, or management of a disease state amenable to treatment by inhibiting $Na_v1.7$ channel activity, for example, one or more of the conditions or disease states mentioned above, comprises administering to a patient in need thereof an effective amount of one or more compounds of the invention, as defined herein, for example, a compound of Formula A or a pharmaceutically acceptable salt thereof. In some embodiments, as mentioned above, it is preferred for the compound of the invention to be present in a pharmaceutical composition.

In general, in whatever form administered, the dosage form administered will contain an amount of at least one compound of the invention, or a salt thereof, which will provide a therapeutically effective serum level of the compound meeting or exceeding the minimum therapeutically effective serum level on a continuous basis throughout the period during which treatment is administered. As mentioned above, a composition of the invention can incorporate additional pharmaceutically active components or be administered simultaneously, contemporaneously, or sequentially with other pharmaceutically active compositions as may be additionally needed in the course of providing treatment.

In one aspect this invention provides also a pharmaceutical composition comprising a pharmaceutical carrier, an effective amount of at least one compound of the invention, for example, a compound of Formula A, and an effective amount of at least one other pharmaceutically active ingredient which is: (i) an opioid agonist or antagonist; (ii) a calcium channel antagonist; (iii) an NMDA receptor agonist or antagonist; (iv) a COX-2 selective inhibitor; (v) an NSAID (non-steroidal anti-inflammatory drug); or (vi) paracetamol (APAP, acetaminophen), and a pharmaceutically acceptable carrier.

Those skilled in the art will appreciate that treatment protocols utilizing at least one compound of the invention can be varied according to the needs of the patient. Thus, compounds of the invention used in the methods of the invention can be administered in variations of the protocols described above. For example, compounds of the invention can be administered discontinuously rather than continuously during the treatment cycle.

As mentioned above, in one aspect the invention provides compounds having activity as Nav 1.7 sodium ion channel inhibitors which have the structure of Formula A, or a salt thereof:

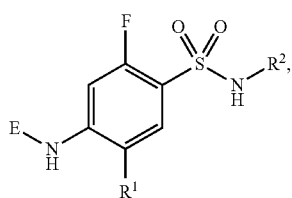

Formula A wherein $R^1$, $R^2$, and E are defined herein.

In some embodiments in compounds of Formula A, "$R^1$" is a halogen, and when selected to be a halogen is preferably —Br or —Cl.

In some embodiments in compounds of Formula A, $R^1$ is preferably —$CH_3$.

In some embodiments of Formula A, $R^2$ is preferably a moiety of the formula:

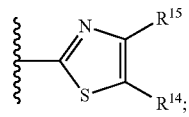

wherein one of "$R^{14}$" and "$R^{15}$" are —H and the other is: (i) —H; (ii) —$CH_3$; or (iii) halogen, preferably —F.

In some embodiments, in a compound of Formula A, E is preferably a moiety of the formula Q-$CH_2$—NH—$(CH_2)_4$—, wherein Q is:

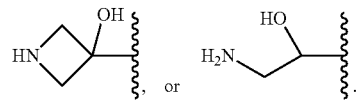

In some embodiments, in a compound of Formula A, E is preferably a moiety of the formula:

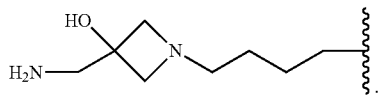

In some embodiments, in a compound of Formula A, preferably E has the structure of Formula $E^{1a}$:

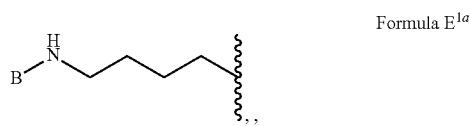

Formula $E^{1a}$ wherein B has the structure:

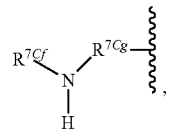

wherein:
(a) $R^{7Cg}$ is —$CH_2$—CH(OH)—$CH_2$— and $R^{7Cf}$ is —H or lower alkyl or lower cyclic alkyl; or
(b) $R^{7Cg}$ is linear alkyl of at least 2 carbon atoms up to 4 carbon atoms, branched alkyl of from 3 up to 6 carbon atoms or cyclic alkyl of up to 6 carbon atoms and $R^{7Cf}$ is linear, branched, or cyclic alkyl of up to 6 carbon atoms that is substituted on one carbon thereof which is beta or further from the nitrogen with —OH.

In some embodiments, in a compound of Formula A, preferably E and $R^2$ are selected to give a compound, or a pharmaceutically acceptable salt thereof, of the formula:

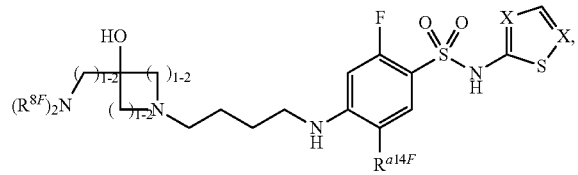

wherein:

X is —N= or —C($R^{C14e}$)=, wherein $R^{C14e}$ is —H, —F, or —CH$_3$;

$R^{a14F}$ is —Cl, —Br or —CH$_3$; and $R^{8F}$ is independently —H or linear, branched, or cyclic alkyl of up to 6 carbon atoms.

In the examples that follow certain of the exemplified compounds, or salts thereof, are prepared as pure enantiomers, or prepared from enantiopure precursors, or are isolated using chiral separation methods after synthesis, for example, chiral chromatography. After isolation of chiral compounds the absolute stereochemistry of the isolated compound was not determined in every example. Accordingly, where pure isomers have been prepared but the absolute configuration has not been verified, the enantiomer isolated in pure form is specified by the following convention.

Unless indicated otherwise, where present, isomers of example compounds were not separated. Unless indicated otherwise, where isomers were separated into fractions containing an excess of a particular isomer, for example, a fraction containing an excess of an optical isomer, which separation may be accomplished, for example, by super critical fluid chromatography, absolute stereochemistry of separated isomers was not determined. For some compounds enantiomers were made in enantiomerically pure form or separated to obtain pure fractions of each enantiomer, and the absolute configuration of each enantiomer was determined, as illustrated herein. Each of those compounds is reported herein structurally with indication of each particular enantiomer using the conventional solid and dashed wedge-bonds at the chiral center and is named in accordance with the specific isomer naming conventions.

Where a reaction scheme appearing in an example employs a compound having one or more stereocenters, the stereocenters are indicated with an asterisk, as shown below in illustration compound Def-1.

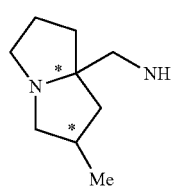

Def-1

Accordingly, Def-1 consists of the following pairs of isomers: (i) Trans-isomers ((2R,7aS)-2-methylhexahydro-1H-pyrrolizin-7a-yl)methanamine (Compound ABC-1) and ((2S,7aR)-2-methylhexahydro-1H-pyrrolizin-7a-yl)methanamine (Compound ABC-2); and (ii) Cis-isomers ((2R,7aR)-2-methylhexahydro-1H-pyrrolizin-7a-yl)methanamine (Compound ABC-3) and ((2S,7aS)-2-methylhexahydro-1H-pyrrolizin-7a-yl)methanamine (Compound ABC-4).

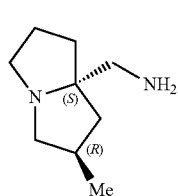

ABC-1

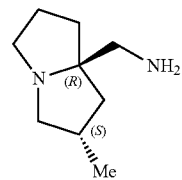

ABC-2

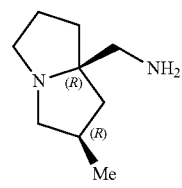

ABC-3

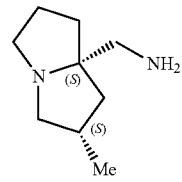

ABC-4

When the compound is prepared and separated into pure enantiomers, albeit without determining the absolute configuration of each enantiomer of the compound, the product will be identified in the title using both enantiomer names, e.g., where ABC-1 and ABC-2 are prepared and separated into pure enantiomers, the title will read "preparation of ((2R,7aS or 2S, 7aR)-2-methylhexahydro-1H-pyrrolizin-7a-yl)methanamine and ((2S,7aR or 2R,7aS)-2-methylhexahydro-1H-pyrrolizin-7a-yl)methanamine". In some instances where enantiomeric compounds are prepared the designation (Cis) or (Trans) may be appended to the name to clarify the relationship of the stereo centers present in the two stereoisomers. As will be appreciated, identification of each product in the experimental preparation as: "R or S enantiomer EX-666" and "S or R enantiomer EX-667", where EX-666 and EX-667 are the same structure with an enantiomeric relationship and the chiral carbon indicated by an asterisk indicates that each pure enantiomer was prepared and has the properties indicated by the data associated with its report and that both said enantiomers were prepared and isolated in increased enantiopurity without determination of the absolute configuration of either compound thus prepared. In such instances each pure enantiomer is claimed Where enantiomeric compounds are prepared in a racemic mixture, asterisks will be inserted into the structural representation to indicate the stereocenters, but the title will reference the preparation of both enantiomers, e.g., where ABC-3 and ABC-4 are prepared as a racemate, the title will read "preparation of ((2R,7aR and 2S7aS)-2-methylhexahydro-1H-pyrrolizin-7a-yl)methanamine".

Those skilled in the art will appreciate that treatment protocols utilizing at least one compound of the invention, as described herein, may be varied according to the needs of the patient. Thus, compounds of the invention used in the methods of this invention may be administered in variations of the protocols described above. For example, the compounds of this invention may be administered discontinuously rather than continuously during the treatment cycle.

The following examples are presented to further illustrate compounds of the invention, but, with reference to the general formula presented above, they are not presented as limiting the invention to these specifically exemplified compounds.

EXAMPLES

Examples of the preparation of compounds of the invention are shown next. In each of the Examples, the identity of the compounds prepared were confirmed by a variety of techniques. In all cases the compounds were analyzed by LC/MS or HPLC.

Where utilized, Prep HPLC was carried out on a Gilson 281 equipped with a Phenomenexd Synergi C18, 100 mm×21.2 mm×5 micron column. Conditions included a flow rate of 25 mL/min., eluted with a 0-40% acetonitrile/water eluent comprising 0.1% v/v TFA.

LC/MS determinations used either an Agilent YMC J'Sphere H-80 (3×50 mm) 5 μm column using mobile phase containing A: 0.1% TFA in water and B: acetonitrile with a gradient from 95:5 (A:B) to 0:100 (A:B) over 3.6 min and 0:100 (A:B) for 0.4 min at a flow rate of 1.4 mL/min, UV detection at 254 and 220 nm and Agilent 1100 quadrupole mass spectrometer or an Agilent TC-C18 (2.1×50 mm) 5 μm column using mobile phase containing A: 0.0375% TFA in water and B: 0.01875% TFA in acetonitrile with a gradient from 90:10 (A:B) for 0.4 min to 90:10 to 0:100 (A:B) over 3 min and 10:90 (A:B) for 0.6 min at a flow rate of 0.8 mL/min, UV detection at 254 and 220 nm and Agilent 6110 quadrupole mass spectrometer.

For some compounds, the identity of the compound was verified by proton NMR and high-resolution MS. Proton NMR were acquired using a Varian Unity-Inova 400 MHz NMR spectrometer equipped with a either a Varian 400 ATB PFG 5 mm, Nalorac DBG 400-5 or a Nalorac IDG 400-5 probe in accordance with standard analytical techniques, unless specified otherwise, and results of spectral analysis are reported.

High resolving power accurate mass measurements were acquired by use of a Bruker Daltonics 7T Fourier transform ion cyclotron resonance (FTICR) mass spectrometer. Samples were dissolved in acetonitrile:water:acetic acid (50:50:0.1% v/v), and ionized by use of electrospray ionization (ESI) yielding [M+H]+ and/or [M+Na]+. External calibration was accomplished with oligomers of polypropylene glycol (PPG, average molecular weight 1000 Da).

Throughout the Examples section, the following abbreviations are used to indicate various reagents, substituents and solvents: AcCN=acetonitrile; AcOH=acetic acid; Boc=tert-butoxycarbonyl; Boc$_2$O or Boc-anhydride=di-tert-butyl carbonate; Bn=Benzyl; DABCO=1,4-diazabicyclo[2.2.2]octane; DAST=diethylaminosulfur trifluoride; DCE=dichloroethane; DCM=dichloromethane; DEAD=diethylazodicarboxylate; DIPEA=diisopropylamine; DMAP=4-dimethylaminopyridine; DMB (2, 4-dimethoxybenzyl-); DMF=dimethylformamide; DMP=Dess-Martin Periodinane; DMS=dimethylsulfide; DMSO=dimethylsulfoxide; DPPA=diphenylphosphoryl azide; dppf=1,1'-bis(diphenylphosphino)ferrocene; EtOAc=ethyl acetate; EtOH=ethanol; Fmoc=fluorenyloxycarbonyl; HATU=1-[Bis(dimethylamino)methylene]-1H-1,2,3-triazolo[4,5-b]pyridinium-3-oxide-hexafluorophosphate; Hex=hexanes; HMPA=hexamethylphosphoramide; HPLC=high-performance liquid chromatography; IPA=isopropyl alcohol; LC/MS or LCMS=liquid chromatography/mass spectrometry; LDA=lithium diisopropylamide; LG=leaving group; LiHMDS=lithium bis(trimethylsilyl)amide; MeOH=methanol; LRMS=low resolution mass spectrometry; MOM=methoxymethyl; MOMCl=methyl chloromethyl ether; MsCl=methanesulfonyl chloride; NMP=N-methylpyrrolidone; Pd/C=palladium on carbon; Pd$_2$(dba)$_3$=tris(dibenzylideneacetone)dipalladium(0); PE=petroleum ether; PG=protecting group; PMP=para-methoxybenzyl; PMBCl=para-methoxybenzyl chloride; Prep-TLC=preparative thin layer chromatography; Py=pyridine; SCX=strong cation exchange; Selectfluor=1-(chloromethyl)-4-fluoro-1,4-diazoniabicyclo[2.2.2]octane ditetrafluoroborate; SFC=Supercritical Fluid Chromatography; TBAF=tetra-n-butylammonium fluoride; TBS=tert-butyldimethylsilyl; TBS-Cl=tert-butyldimethylsilyl chloride; THF=Tetrahydrofuran; TFA=trifluoroacetic acid; TFAA=trifluoroacetic acid anhydride; TsOH=para-toluenesulfonic acid; UV=ultraviolet; Xantphos=4,5-Bis(diphenylphosphino)-9,9-dimethyxanthene.

In general, compounds of the invention can be prepared by the methods outlined in Schemes A-D. In Scheme A, displacement of a leaving group (LG such as, but not limited to, F) from protected acylsulfonamide intermediates A-1 (PG such as, but not limited to, Boc, DMB, PMB, MOM) by amine R$^1$NH$_2$ provides compounds A-2. Subsequent removal of PG affords compounds A-3. Alternatively, the amine R$^1$NH$_2$ can be reacted with unprotected precursors A-1 (PG=H) to provide A-3 directly.

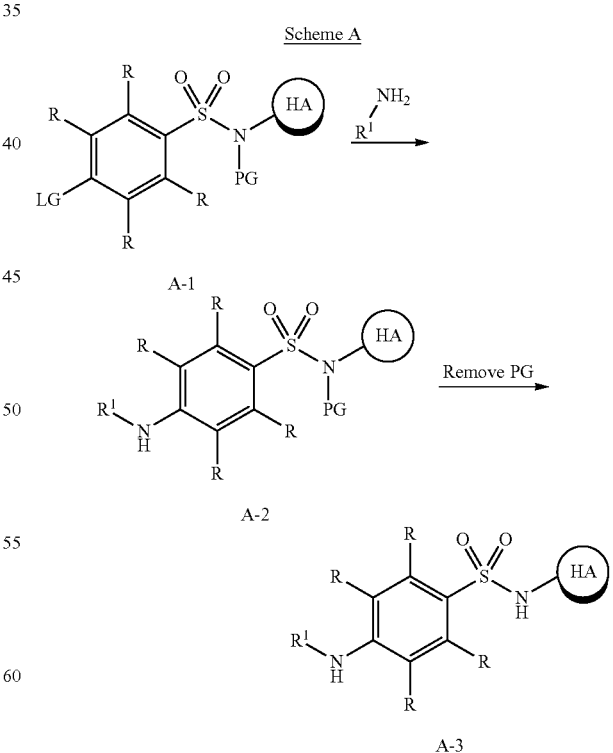

Scheme A

Intermediates A-2 that possess an aldehyde moiety on R$^1$, such as B-1 (PG such as, but not limited to, Boc, DMB, PMB, MOM), can undergo reductive amination reactions with monoprotected diamines B-2 (PG such as, but not limited to, Boc, Fmoc), followed by removal of PG to produce final compounds B-3. Alternatively, B-2 can be reacted with unprotected precursors B-1 (PG=H), followed by amine deprotection to provide compounds B-3.

Scheme B

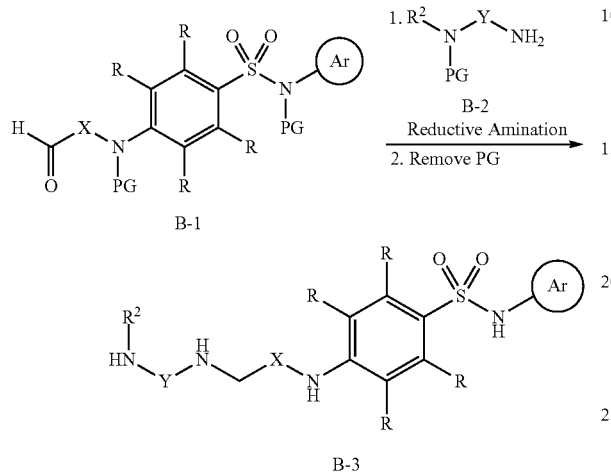

In addition, compounds A-2 with an amine group on R¹, such as C-1 (PG such as, but not limited to, Boc, DMB, PMB, MOM), can undergo coupling reactions with N-protected amino acids C-2 (PG such as, but not limited to, Boc, Fmoc) to afford amides such as C-3, which can then be reduced to the corresponding amines by methods known to those skilled in the art. Removal of both PG provides product C-4. Additionally, C-2 (PG such as, but not limited to, Boc, Fmoc) can be reacted with an unprotected precursor C-1 (PG=H), which upon reduction to the resultant C-3, followed by deprotection of the amine, affords the corresponding product C-4.

Scheme C

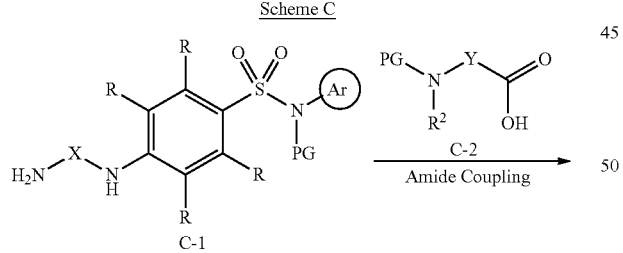

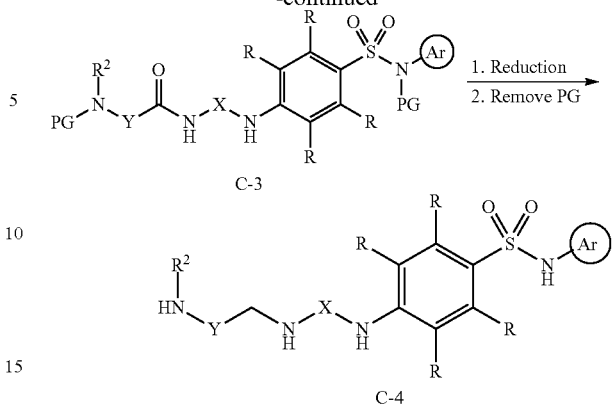

In another approach, compounds C-1 (PG such as, but not limited to, Boc, DMB, PMB, MOM), can be coupled via reductive amination reactions to N-protected aldehydes D-1 (PG such as, but not limited to, Boc, Fmoc) followed by removal of all PG to produce final compounds D-2. In some cases, D-1 (PG such as, but not limited to, Boc, Fmoc) can undergo reductive amination reactions with an unprotected amine precursor C-1 (PG=H), followed by amine deprotection to provide products D-2.

Scheme D

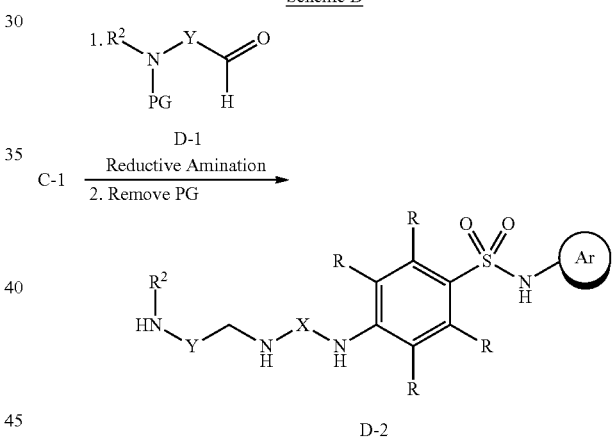

The following examples are provided to more fully illustrate the invention, and are not to be construed as limiting the scope of the invention in any manner.

Example 1-1: 4-[(4-{[(2S)-3-amino-2-hydroxypropyl]amino}butyl)amino]-5-chloro-2-fluoro-N-1,2,4-thiadiazol-5-ylbenzenesulfonamide (Ex 1-01)

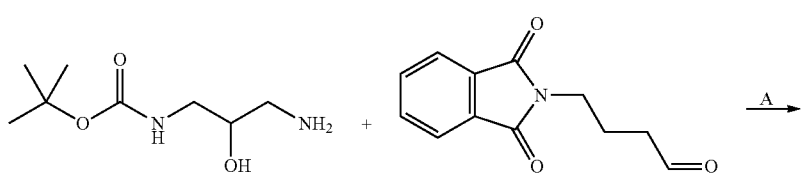

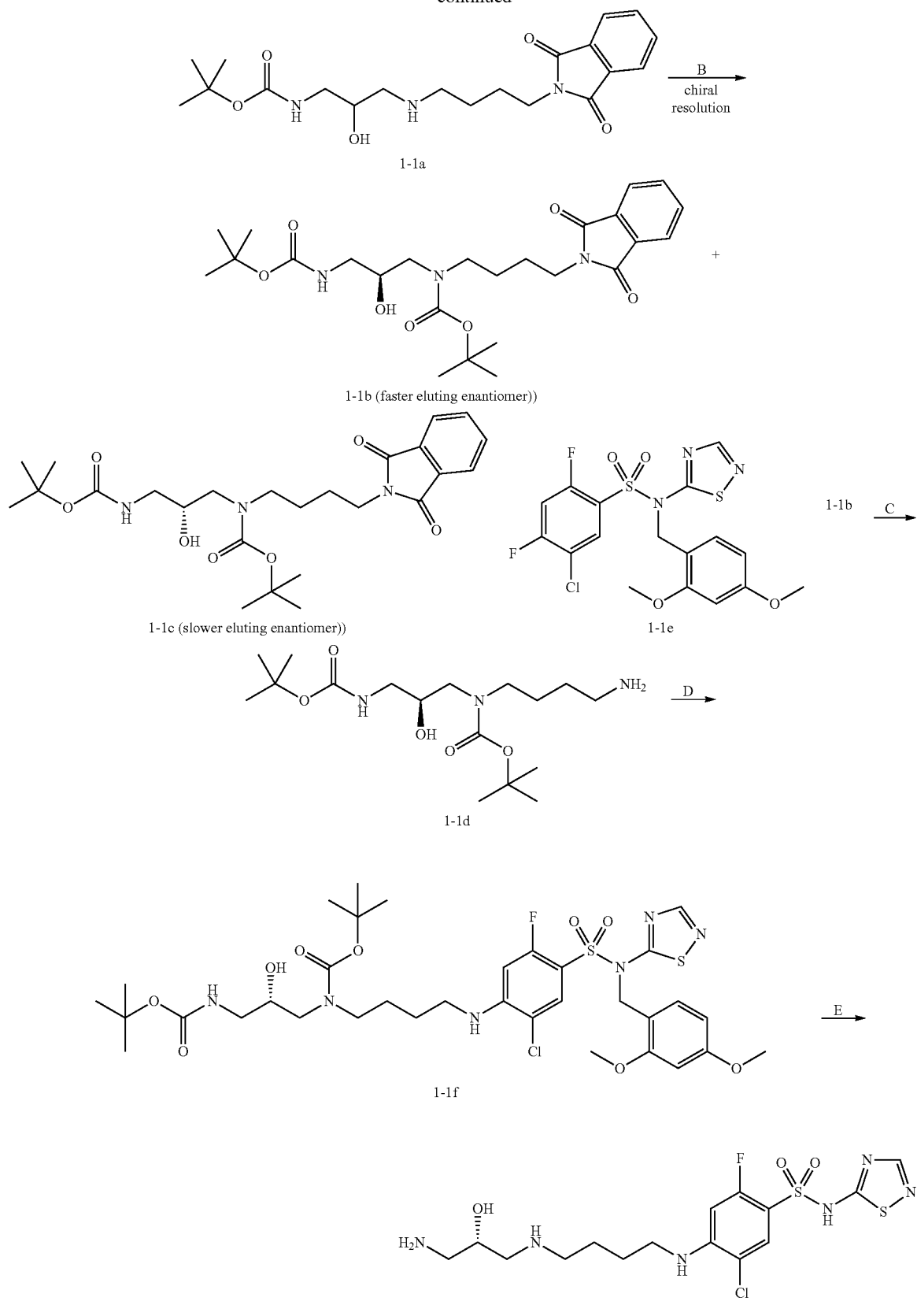
-continued

Step A: tert-butyl (3-((4-(1,3-dioxoisoindolin-2-yl)butyl)amino)-2-hydroxypropyl)carbamate (1-1a)

To a solution of tert-butyl (3-amino-2-hydroxypropyl) carbamate (4.99 g, 26.2 mmol) in DCE (40 ml) was added 4-(1,3-dioxoisoindolin-2-yl)butanal (3.8 g, 17.5 mmol). The mixture was stirred in a capped flask at room temperature for 30 min. Then was added sodium triacetoxyborohydride (9.27 g, 43.7 mmol) and the reaction mixture was stirred overnight at room temperature. The resulting reaction mixture was diluted with DCM and then washed with sat. NaHCO$_3$. The organic layer was separated, dried over MgSO$_4$, filtered, and concentrated in vacuo. The residue was carried onto the next BOC-protection step without any further purification. LRMS m/z (M+H) 392.3 found, 392.2 calc'd.

Step B: tert-butyl (S and R)-(3-((tert-butoxycarbonyl)amino)-2-hydroxypropyl)(4-(1,3-dioxoisoindolin-2-yl)butyl)carbamate and tert-butyl (R)-(3-((tert-butoxycarbonyl)amino)-2-hydroxypropyl)(4-(1,3-dioxoisoindolin-2-yl)butyl)carbamate (1-1b and 1-1c)

To a solution of crude 1-1a (6.85 g, 17.5 mmol) in DCM (50 mL) was added Boc$_2$O-anhydride (6.09 mL, 26.2 mmol) and DIPEA (7.64 mL, 43.7 mmol). The reaction mixture was stirred at room temperature under N$_2$ atmosphere overnight. The resulting reaction mixture was diluted with DCM and H$_2$O. The organic layer was separated, dried over MgSO$_4$, filtered, and concentrated in vacuo. The residue was purified by flash chromatography using 0-50% EtOAc/Hex to yield the desired racemate. LRMS m/z (M+H) 492.6 found, 492.3 calc'd. The enantiomers were separated by chiral chromatography on an IC column eluting with 20% IPA/CO$_2$ to afford intermediate 1-1b (S-enantiomer) as the faster eluting enantiomer and intermediate 1-1c (R-enantiomer) as the slower eluting enantiomer. The absolute configuration of the 1-1b enantiomer thus isolated was determined by proton NMR after derivatizing the secondary alcohol to an ester using chiral methoxyphenylacetic acid in accordance with known procedures (Chem. Rev. 2004, (104), pp 17-117).

Step C: tert-butyl (S)-(4-aminobutyl)(3-((tert-butoxycarbonyl)amino)-2-hydroxypropyl)carbamate (1-1d)

To a solution of 1-1b (110 mg, 0.224 mmol) in EtOH (5 mL) was added hydrazine monohydrate (0.152 mL, 3.13 mmol). The reaction mixture was stirred under N$_2$ atmosphere at 50° C. for 2 h. The resulting reaction mixture was filtered washing with DCM. The filtrate was concentrated in vacuo. The residue was diluted with DCM and H$_2$O. The organic layer was separated, dried over MgSO$_4$, filtered, and concentrated in vacuo. The residue was carried onto the next step without any further purification. LRMS (MS ES+) m/z (M+H) 362.3 found, 362.3 calc'd.

Step D: tert-butyl (S)-(3-((tert-butoxycarbonyl)amino)-2-hydroxypropyl)(4-((2-chloro-4-(N-(2,4-dimethoxybenzyl)-N-(1,2,4-thiadiazol-5-yl)sulfamoyl)-5-fluorophenyl)amino)butyl)carbamate (1-1f)

To a solution of 5-chloro-N-(2,4-dimethoxybenzyl)-2,4-difluoro-N-(1,2,4-thiadiazol-5-yl)benzenesulfonamide (330 mg, 0.714 mmol) in DMF (5 mL) was added 1-1d (258 mg, 0.714 mmol) and DIPEA (374 µL, 2.143 mmol). The reaction mixture was capped and stirred at room temperature overnight. The resulting reaction mixture was diluted with EtOAc and H$_2$O. The organic layer was separated and washed with H$_2$O three more times. The resulting organic layer was separated, dried over MgSO$_4$, filtered, and concentrated in vacuo. The residue was purified by flash chromatography on silica gel (0-10% MeOH/DCM) to yield the desired product. LRMS m/z (M+H) 803.4 found, 803.3 calc'd.

Step E: 4-((4-(((2S)-3-amino-2-hydroxypropyl)amino)butyl)amino)-5-chloro-2-fluoro-N-(1,2,4-thiadiazol-5-yl)benzenesulfonamide (Example 1-01)

To a solution of 1-1f (370 mg, 0.461 mmol) in DCM (2 mL) was added TFA (2 mL, 26.0 mmol). The reaction mixture was stirred at room temperature opened to air for 1 h. The resulting reaction mixture was concentrated in vacuo. The residue was dissolved in 1:1 DMSO:H$_2$O mixture and purified by reverse phase HPLC (ISCO 125 g HP-C18 column) using AcCN+0.05% TFA and H$_2$O+0.05% TFA. The combined fractions with the desired product were concentrated in vacuo and then the residue was dissolved in 10:1 1N HCl:AcCN, frozen, and dried on a lyophilizer to yield the desired product as the HCl salt. LRMS m/z (M+H) 453.2 found, 453.1 calc'd. 1H NMR (500 MHz, CD$_3$OD): δ 8.21 (s, 1H); 7.69 (d, J=7.1 Hz, 1H); 6.60 (d, J=12.8 Hz, 1H); 4.19 (t, J=8.8 Hz, 1H); 3.31 (d, 2H); 3.22-2.96 (m, 6H); 1.82-1.71 (m, 4H).

The compound of Ex 1-06 (Table 1) was prepared using the above procedure B:

EX 1-06

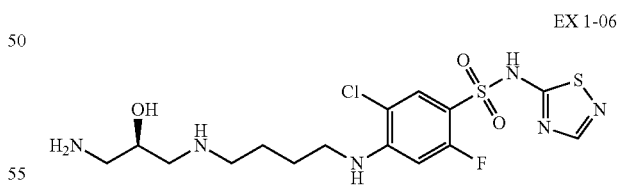

is prepared by following steps C to E of the above procedure only using intermediate 1-1c in place of intermediate 1-1b.

The following compounds were prepared using the methodology herein, but utilizing the appropriately substituted reagent, as described in the Reaction Schemes and Examples. The requisite starting materials were commercially available, described in the literature or readily synthesized by one skilled in the art of organic synthesis without undue experimentation.

TABLE I

| Exp No | Structure | Name | Exact Mass [M + H]+ calc; found |
|---|---|---|---|
| 1-02 | 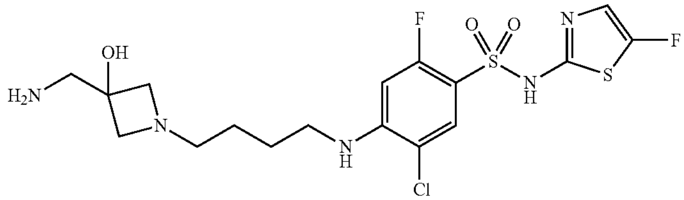 [SMILES: NCC1(O)CN(CCCCNc2cc(F)c(S(=O)(=O)Nc3ncc(F)s3)cc2Cl)C1] | 4-({4-[3-(aminomethyl)-3-hydroxyazetidin-1-yl]butyl}amino)-5-chloro-2-fluoro-N-(5-fluoro-1,3-thiazol-2-yl)benzenesulfonamide | 482.1; 481.9 |
| 1-03 | 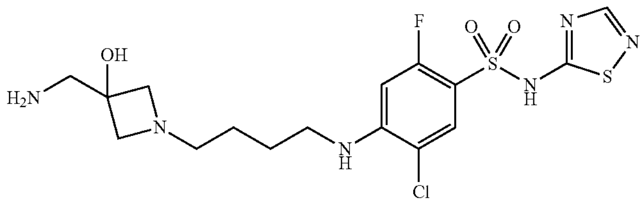 [SMILES: NCC1(O)CN(CCCCNc2cc(F)c(S(=O)(=O)Nc3ncns3)cc2Cl)C1] | 4-({4-[3-(aminomethyl)-3-hydroxyazetidin-1-yl]butyl}amino)-5-chloro-2-fluoro-N-1,2,4-thiadiazol-5-ylbenzenesulfonamide | 465.1; 464.9 |
| 1-04 | 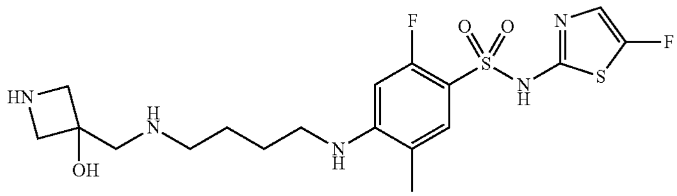 [SMILES: Cc1cc(S(=O)(=O)Nc2ncc(F)s2)c(F)cc1NCCCCNCC1(O)CNC1] | 2-fluoro-N-(5-fluoro-1,3-thiazol-2-yl)-4-[(4-{[(3-hydroxyazetidin-3-yl)methyl]amino}butyl)amino]-5-methylbenzenesulfonamide | 462.1; 462.2 |
| 1-05 | 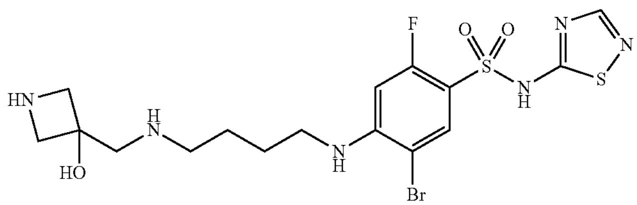 [SMILES: O=S(=O)(Nc1ncns1)c1cc(Br)c(NCCCCNCC2(O)CNC2)cc1F] | 5-bromo-2-fluoro-4-[(4-{[(3-hydroxyazetidin-3-yl)methyl]amino}butyl)amino]-N-1,2,4-thiadiazol-5-ylbenzenesulfonamide | 509.0; 509.1 |
| 1-06 | 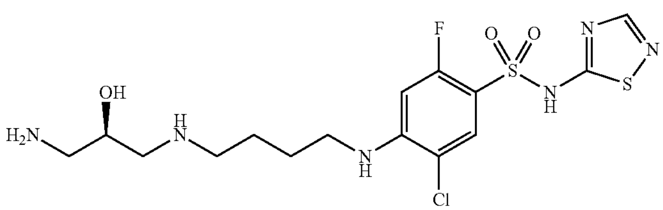 [SMILES: NC[C@@H](O)CNCCCCNc1cc(F)c(S(=O)(=O)Nc2ncns2)cc1Cl] | 4-[(4-{[(2R)-3-amino-2-hydroxypropyl]-amino}butyl)amino]-5-chloro-2-fluoro-N-1,2,4-thiadiazol-5-yl-benzenesulfonamide | 453.1; 453.2 |
| 1-07 | 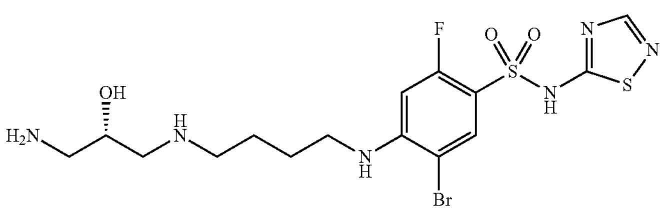 [SMILES: NC[C@H](O)CNCCCCNc1cc(F)c(S(=O)(=O)Nc2ncns2)cc1Br] | 4-[(4-{[(2S)-3-amino-2-hydroxypropyl]-amino}butyl)amino]-5-bromo-2-fluoro-N-1,2,4-thiadiazol-5-yl-benzenesulfonamide | 497.0; 497.1 |
| 1-08 | 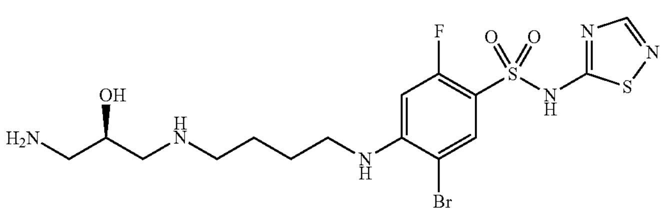 [SMILES: NC[C@@H](O)CNCCCCNc1cc(F)c(S(=O)(=O)Nc2ncns2)cc1Br] | 4-[(4-{[(2R)-3-amino-2-hydroxypropyl]-amino}-butyl)amino]-5-bromo-2-fluoro-N-1,2,4-thiadiazol-5-yl-benzenesulfonamide | 497.0; 497.1 |

TABLE I-continued

| Exp No | Structure | Name | Exact Mass [M + H]+ calc; found |
|---|---|---|---|
| 1-09 | 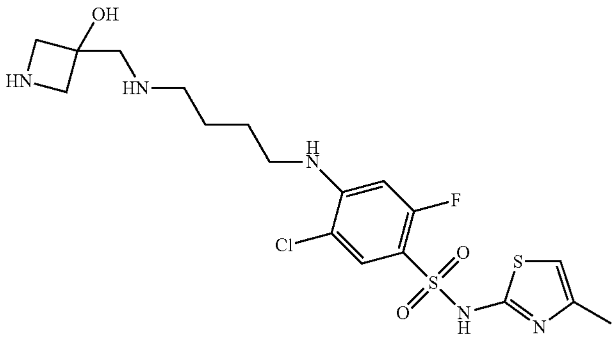 [SMILES: Cc1csc(NS(=O)(=O)c2cc(Cl)c(NCCCCNCC3(O)CNC3)cc2F)n1] | 5-chloro-2-fluoro-4-[(4-{[(3-hydroxyazetidin-3-yl)methyl]amino}butyl)amino]-N-(4-methyl-1,3-thiazol-2-yl)-benzenesulfonamide | 478.1; 478.2 |
| Ex 1-11 | 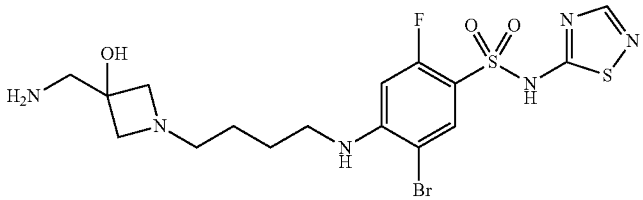 [SMILES: NCC1(O)CN(CCCCNc2cc(F)c(S(=O)(=O)Nc3ncns3)cc2Br)C1] | 4-((4-(3-(aminomethyl)-3-hydroxyazetidin-1-yl)butyl)amino)-5-bromo-2-fluoro-N-(1,2,4-thiadiazol-5-yl)benzenesulfonamide | 509.0; 508.7 |

Example 2-1: 5-chloro-2-fluoro-4-[(4-{[(3-hydroxyazetidin-3-yl)methyl]amino}butyl)amino]-N-1,2,4-thiadiazol-5-ylbenzenesulfonamide (Ex 2-01)

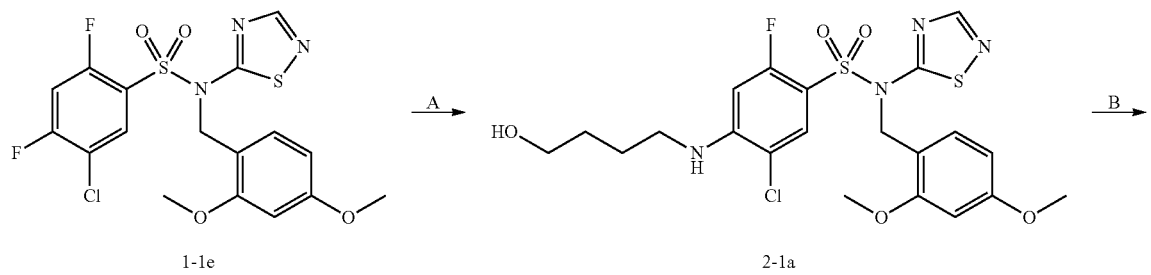

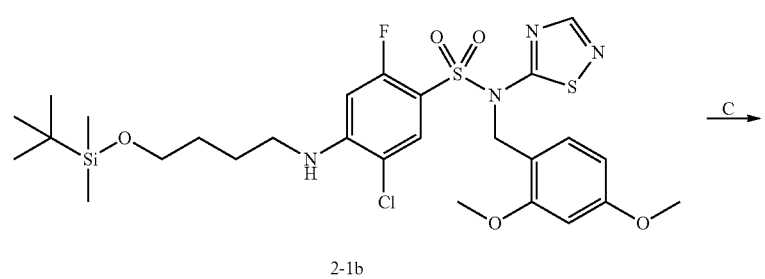

-continued
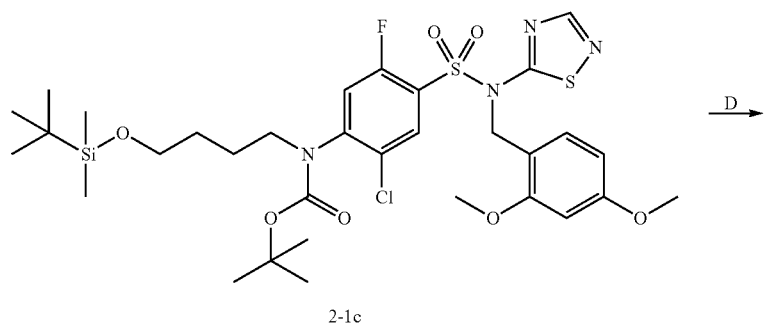
2-1c
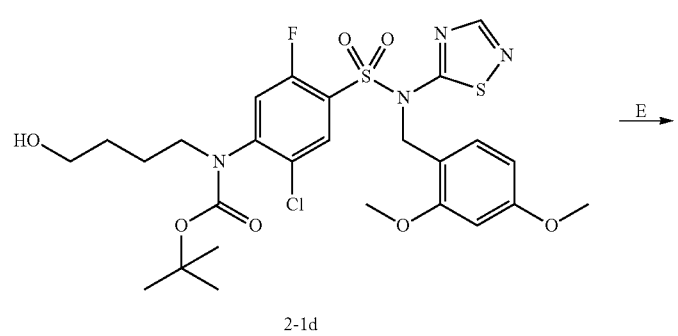
2-1d
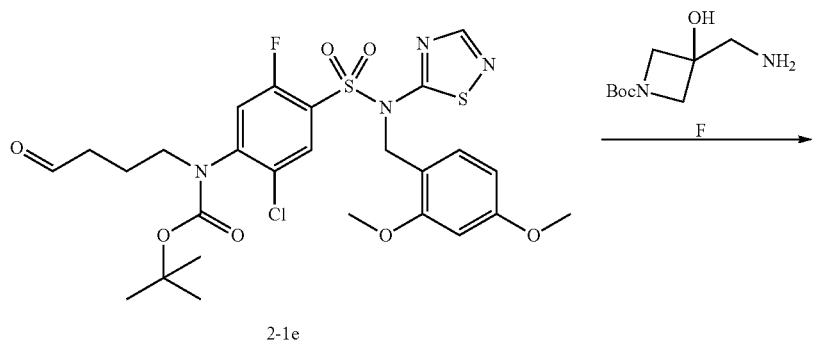
2-1e
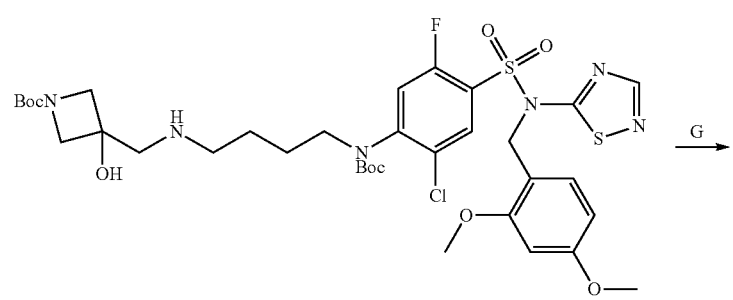
2-1f
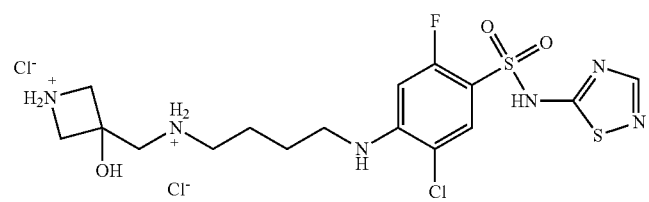
Example 2-1

Step A: 5-chloro-N-(2,4-dimethoxybenzyl)-2-fluoro-4-((4-hydroxybutyl)amino)-N-(1,2,4-thiadiazol-5-yl)benzenesulfonamide (2-1a)

To a solution of 5-chloro-N-(2,4-dimethoxybenzyl)-2,4-difluoro-N-(1,2,4-thiadiazol-5-yl)benzenesulfonamide (8.0 g, 17 mmol) in DMF (50 mL) was added 4-amino-1-butanol (1.76 mL, 19.0 mmol) and DIPEA (4.54 mL, 26.0 mmol). The reaction mixture was stirred overnight under $N_2$ atmosphere at room temperature. The resulting reaction mixture was diluted with EtOAc and $H_2O$. The organic layer was separated and then washed with $H_2O$ three times. The resulting organic layer was dried over $MgSO_4$, filtered, and concentrated in vacuo. The residue was purified by flash chromatography on silica gel (0-65% EtOAc/Hex) to yield the desired product. LRMS m/z (M+H) 531.2 found, 531.1 calc'd.

Step B: 4-((4-((tert-butyldimethylsilyl)oxy)butyl)amino)-5-chloro-N-(2,4-dimethoxybenzyl)-2-fluoro-N-(1,2,4-thiadiazol-5-yl)benzenesulfonamide (2-1b)

To a solution of 2-1a (6.56 g, 12.3 mmol) in DMF (50 mL) was added imidazole (1.85 g, 27.2 mmol) and then TBS-Cl (2.05 g, 13.6 mmol). The reaction mixture was stirred at room temperature overnight under $N_2$ atmosphere. The resulting reaction was diluted with EtOAc and $H_2O$. The organic layer was separated and then washed with $H_2O$ three times. The resulting organic layer was separated, dried over $MgSO_4$, filtered, and concentrated in vacuo. The residue was purified by flash chromatography on silica gel (0-25% EtOAc/Hex) to yield the desired product. LCMS m/z (M+H) 645.3 found, 645.2 calc'd.

Step C: tert-butyl (4-((tert-butyldimethylsilyl)oxy)butyl)(2-chloro-4-(N-(2,4-dimethoxybenzyl)-N-(1,2,4-thiadiazol-5-yl)sulfamoyl)-5-fluorophenyl)carbamate (2-1c)

To a solution of 2-1b (7.6 g, 11.8 mmol) in NMP (50 mL) was added Boc-anhydride (8.20 mL, 35.3 mmol) and then DMAP (1.44 g, 11.8 mmol). The reaction mixture was stirred at room temperature overnight under $N_2$ atmosphere. The resulting reaction mixture was diluted with EtOAc and $H_2O$. The organic layer was separated and then washed with $H_2O$ three times. The resulting organic layer was separated, dried over $MgSO_4$, filtered, and concentrated in vacuo. The residue was purified by flash chromatography on silica gel (0-20% EtOAc/Hex) to yield the desired product. LRMS m/z (M+H) 745.4 found, 745.2 calc'd.

Step D: tert-butyl (2-chloro-4-(N-(2,4-dimethoxybenzyl)-N-(1,2,4-thiadiazol-5-yl)sulfamoyl)-5-fluorophenyl)(4-hydroxybutyl)carbamate (2-1d)

To a solution of 2-1c (6.12 g, 8.21 mmol) in THF (60 mL) was added TBAF (10.7 mL, 10.7 mmol) slowly at 0° C. The reaction mixture was stirred to room temperature under $N_2$ atmosphere overnight. The resulting reaction mixture was diluted with EtOAc and $H_2O$. The organic layer was separated, dried over $MgSO_4$, filtered, and concentrated in vacuo. The residue was purified by flash chromatography on silica (0-50% EtOAc/Hex) to yield the desired product. LRMS m/z (M+H) 631.3 found, 631.1 calc'd.

Step E: tert-butyl (2-chloro-4-(N-(2,4-dimethoxybenzyl)-N-(1,2,4-thiadiazol-5-yl)sulfamoyl)-5-fluorophenyl)(4-oxobutyl)carbamate (2-1e)

To a solution of 2-1d (4.15 g, 6.58 mmol) in DCM (50 mL) was added pyridine (1.60 mL, 19.7 mmol) and then Dess-Martin Periodinane (4.18 g, 9.86 mmol) at 0° C. The reaction mixture was stirred at room temperature overnight under $N_2$ atmosphere. The resulting reaction mixture was quenched with saturated sodium thiosulfate and diluted with DCM and $H_2O$. The organic layer was extracted three times with DCM from the aqueous layer. The combined organic layers were dried over $MgSO_4$, filtered, and concentrated in vacuo. The residue was purified by flash chromatography on silica gel (0-60% EtOAc/Hex) to yield the desired product. LCMS m/z (M+H) 629.3 found, 629.1 calc'd.

Step F: tert-butyl 3-(((4-((tert-butoxycarbonyl)(2-chloro-4-(N-(2,4-dimethoxybenzyl)-N-(1,2,4-thiadiazol-5-yl)sulfamoyl)-5-fluorophenyl)amino)butyl)amino)methyl)-3-hydroxyazetidine-1-carboxylate (2-1f)

To a solution of 2-1e (100 mg, 0.159 mmol) and tert-butyl 3-(aminomethyl)-3-hydroxyazetidine-1-carboxylate (51.4 mg, 0.254 mmol) was added DCM (1 mL). The clear solution was stirred for 30 min before sodium triacetoxyborohydride (101 mg, 0.477 mmol) was added. The reaction became turbid and was stirred at room temperature for 1 h. The mixture was diluted with DCM and quenched with saturated $NaHCO_3$ (aq). The layers were separated and the aqueous layer was extracted with DCM for three times. The organic layers were combined, dried over MgSO4, filtered and concentrated. LRMS m/z (M+H) 815.3 found, calc'd 815.3.

Step G: 5-chloro-2-fluoro-4-[(4-{[(3-hydroxyazetidin-3-yl)methyl]amino}butyl)amino]-N-1,2,4-thiadiazol-5-ylbenzenesulfonamide (Example 2-1)

The crude product 2-1f was dissolved in DCM (2 mL) and TFA (2 mL), and stirred at room temperature for 1 h. The reaction mixture was concentrated, taken up in 1:1 DMSO:water, filtered and the filtrate was purified by reverse phase chromatography (100 g C18 column, 0-100% AcCN with 0.05% TFA in water with 0.05% TFA) to yield the product after lyophilization. To the lyophilisate was added 1N HCl (1 mL), and AcCN (1 mL). The solution was frozen and lyophilized again to yield product. LRMS m/z (M+H) 465.0 found, 465.1 calc'd. 1H NMR (400 MHz, $CD_3OD$): δ 8.22 (s, 1H); 7.65 (d, J=7.1 Hz, 1H); 6.58 (d, J=12.8 Hz, 1H); 4.28 (d, J=11.8 Hz, 2H); 4.13 (d, J=11.7 Hz, 2H); 3.51 (s, 2H); 3.32 (t, J=6.4 Hz, 2H), 3.12 (t, J=7.7 Hz, 2H); 1.80-1.86 (m, 2H); 1.69-1.74 (m, 2H).

Preparation of Example 2-01 Freebase

The compound of Example 2-01 was isolated from the reaction mixture as a hydrochloride salt. The Freebase form of this compound was prepared in accordance with the following procedure:

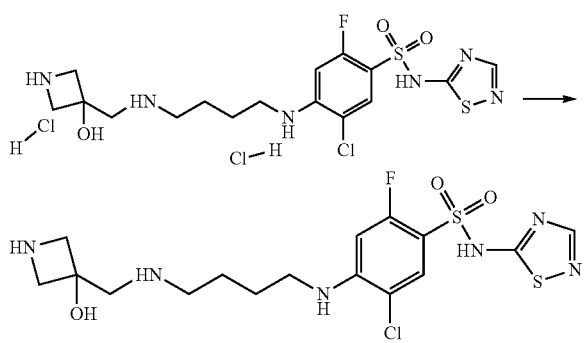

Into each of 3 aliquots of 10 mL of methanol (MeOH) was dissolved a 500 mg aliquot of the compound of Example 2-01. Each aliquot of methanol solution was separately loaded onto a Discovery DSC-SCX (polymerically bonded benzene sulfonic acid group on silica support) 10 g plug. The plug was eluted with MeOH first, and the fraction collected was disgarded. The plug was then eluted with 2N NH₃ in MeOH, and the fraction was concentrated to yield a white solid.

The white solid was then dissolved into small amount of water/DMSO, and loaded onto 275 g C18 column, eluting with 0-100% acetonitrile (AcCN) in water. The product fractions collected from the three iterations were combined, frozen, and lyophilized to provide the compound of Ex 2-01 in free-base form.

LCMS m/z (M+H) 465.2 found, 465.1 calc'd. 1H NMR (DMSO-d₆, 500 MHz): δH 7.84 (s, 1H), 7.50 (d, J=7.3 Hz, 1H), 6.53 (d, J=12.7 Hz, 1H), 6.09 (m, 1H), 6.00 (brs, 1H), 4.09 (brs, 1H), 3.82 (d, J=10.4 Hz, 2H), 3.69 (d, J=10.4 Hz, 2H), 3.17 (m, 2H), 2.70 (s, 2H), 2.60 (t, J=6.9 Hz, 2H), 1.55 (m, 2H), 1.44-1.47 (m, 2H).

The following compounds were prepared using the methodology herein, but substituting the appropriately substituted reagent, as described in the Reaction Schemes and Examples. The requisite starting materials were commercially available, described in the literature or readily synthesized by one skilled in the art of organic synthesis without undue experimentation.

TABLE 2

| Exp No | Structure | Name | Exact Mass [M + H]+ calc; found |
|---|---|---|---|
| 2-02 | 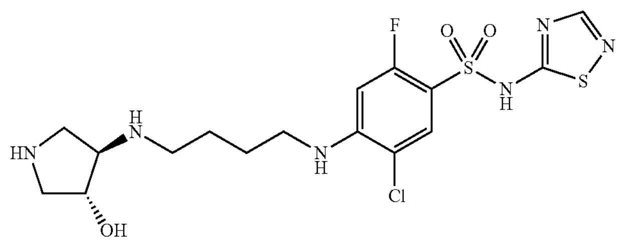 [SMILES: O=S(=O)(Nc1ncns1)c1cc(Cl)c(NCCCCN[C@@H]2CNC[C@H]2O)cc1F] | 5-chloro-2-fluoro-4-[(4-{[(3R,4R)-4-hydroxypyrrolidin-3-yl]amino}butyl)amino]-N-1,2,4-thiadiazol-5-ylbenzenesulfonamide | 465.1; 465.2 |
| 2-03 | 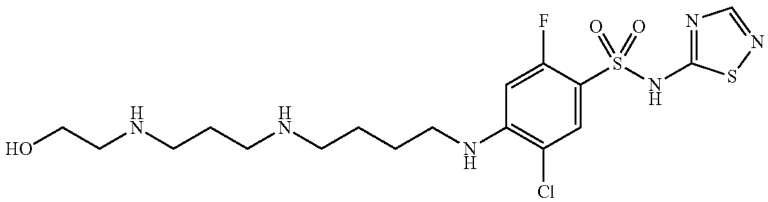 [SMILES: O=S(=O)(Nc1ncns1)c1cc(Cl)c(NCCCCNCCCNCCO)cc1F] | 5-chloro-2-fluoro-4-{[4-({3-[(2-hydroxyethyl)amino]propyl}amino)butyl]amino}-N-1,2,4-thiadiazol-5-ylbenzenesulfonamide | 481.1; 481.2 |
| 2-04 | 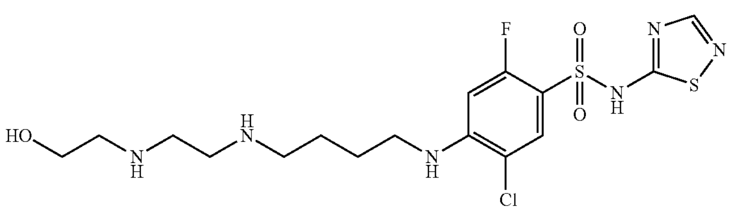 [SMILES: O=S(=O)(Nc1ncns1)c1cc(Cl)c(NCCCCNCCNCCO)cc1F] | 5-chloro-2-fluoro-4-{[4-({2-[(2-hydroxyethyl)amino]ethyl}amino)butyl]amino}-N-1,2,4-thiadiazol-5-ylbenzenesulfonamide | 467.1; 467.2 |
| 2-05 | 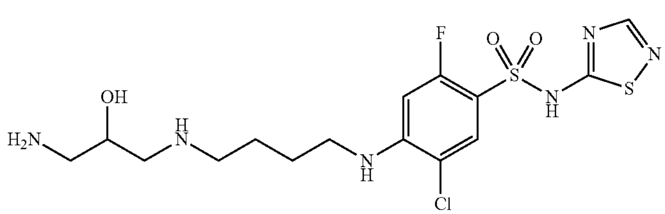 [SMILES: NCC(O)CNCCCCNc1cc(F)c(S(=O)(=O)Nc2ncns2)cc1Cl] | 4-({4-[(3-amino-2-hydroxypropyl)amino]butyl}amino)-5-chloro-2-fluoro-N-1,2,4-thiadiazol-5-ylbenzenesulfonamide | 453.1; 453.2 |

TABLE 2-continued

| Exp No | Structure | Name | Exact Mass [M + H]+ calc; found |
|---|---|---|---|
| 2-06 | 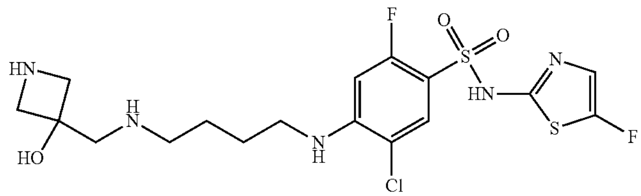 [SMILES: O=S(=O)(Nc1ncc(F)s1)c1cc(Cl)c(NCCCCNCC2(O)CNC2)cc1F] | 5-chloro-2-fluoro-N-(5-fluoro-1,3-thiazol-2-yl)-4-[(4-{[(3-hydroxyazetidin-3-yl)methyl]amino}butyl)amino]benzenesulfonamide | 482.1; 481.9 |
| 2-07 | 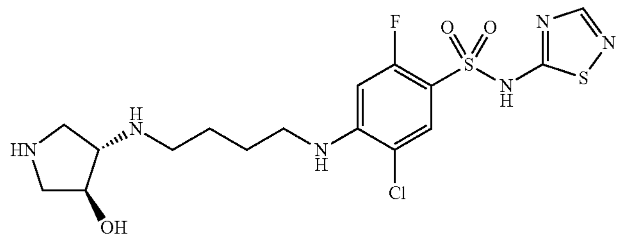 [SMILES: O=S(=O)(Nc1ncns1)c1cc(Cl)c(NCCCCN[C@H]2CNC[C@@H]2O)cc1F] | 5-chloro-2-fluoro-4-[(4-{[(3S,4S)-4-hydroxypyrrolidin-3-yl]amino}butyl)amino]-N-1,2,4-thiadiazol-5-ylbenzenesulfonamide | 465.1; 465.2 |
| 2-08 | 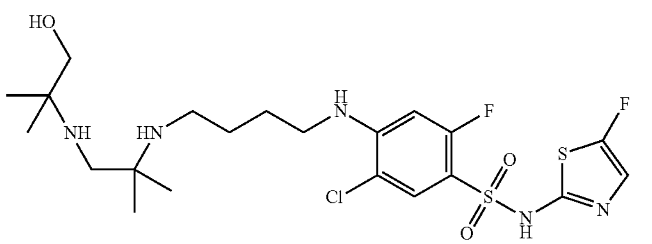 [SMILES: CC(C)(CO)NCC(C)(C)NCCCCNc1cc(F)c(S(=O)(=O)Nc2ncc(F)s2)cc1Cl] | 5-chloro-2-fluoro-N-(5-fluoro-1,3-thiazol-2-yl)-4-{[4-({2-[(2-hydroxy-1,1-dimethylethyl)amino]-1,1-dimethylethyl}amino)butyl]amino}benzenesulfonamide | 540.2; 540.2 |
| 2-09 | 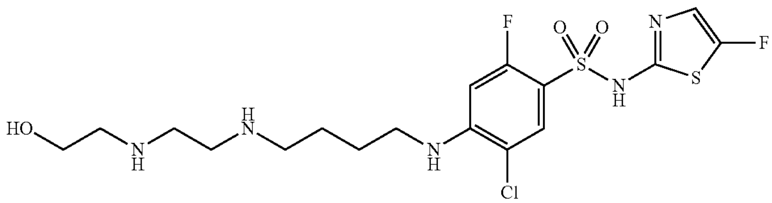 [SMILES: O=S(=O)(Nc1ncc(F)s1)c1cc(Cl)c(NCCCCNCCNCCO)cc1F] | 5-chloro-2-fluoro-N-(5-fluoro-1,3-thiazol-2-yl)-4-{[4-({2-[(2-hydroxyethyl)amino]ethyl}amino)butyl]amino}benzenesulfonamide | 484.1; 484.2 |
| 2-10 | 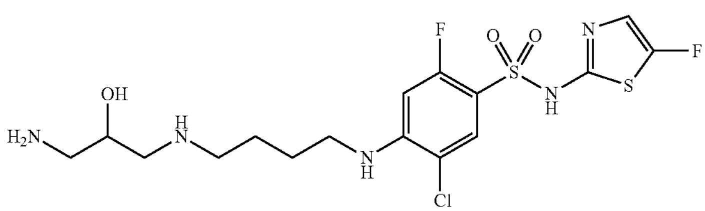 [SMILES: NCC(O)CNCCCCNc1cc(F)c(S(=O)(=O)Nc2ncc(F)s2)cc1Cl] | 4-({4-[(3-amino-2-hydroxypropyl)amino]butyl}amino)-5-chloro-2-fluoro-N-(5-fluoro-1,3-thiazol-2-yl)benzenesulfonamide | 470.1; 470.1 |
| 2-11 | 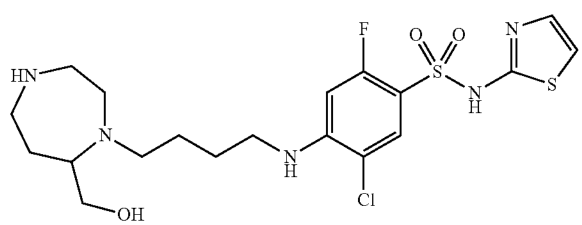 [SMILES: O=S(=O)(Nc1nccs1)c1cc(Cl)c(NCCCCN2CCNCCC2CO)cc1F] | 5-chloro-2-fluoro-4-({4-[7-(hydroxymethyl)-1,4-diazepan-1-yl]butyl}amino)-N-1,3-thiazol-2-ylbenzenesulfonamide | 492.1; 492.2 |

TABLE 2-continued

| Exp No | Structure | Name | Exact Mass [M + H]+ calc; found |
|---|---|---|---|
| 2-12 | 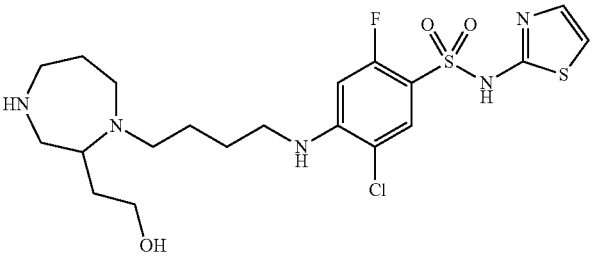 [SMILES: O=S(=O)(Nc1nccs1)c1cc(Cl)c(NCCCCN2CCCNCC2CCO)cc1F] | 5-chloro-2-fluoro-4-({4-[2-(2-hydroxyethyl)-1,4-diazepan-1-yl]butyl}amino)-N-1,3-thiazol-2-ylbenzenesulfonamide | 506.1; 506.2 |
| 2-13 | 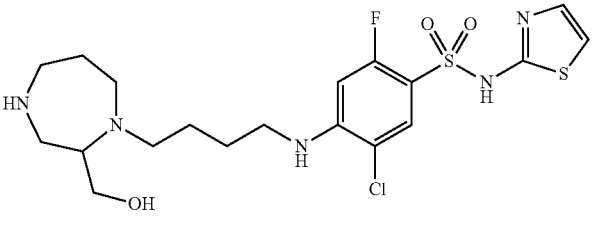 [SMILES: O=S(=O)(Nc1nccs1)c1cc(Cl)c(NCCCCN2CCCNCC2CO)cc1F] | 5-chloro-2-fluoro-4-({4-[2-(hydroxymethyl)-1,4-diazepan-1-yl]butyl}amino)-N-1,3-thiazol-2-ylbenzenesulfonamide | 492.1; 492.2 |
| 2-14 | 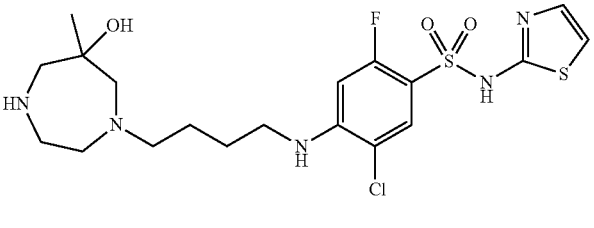 [SMILES: CC1(O)CNCCN(CCCCNc2cc(F)c(S(=O)(=O)Nc3nccs3)cc2Cl)C1] | 5-chloro-2-fluoro-4-{[4-(6-hydroxy-6-methyl-1,4-diazepan-1-yl)butyl]amino}-N-1,3-thiazol-2-ylbenzenesulfonamide | 492.1; 492.2 |
| 2-15 | 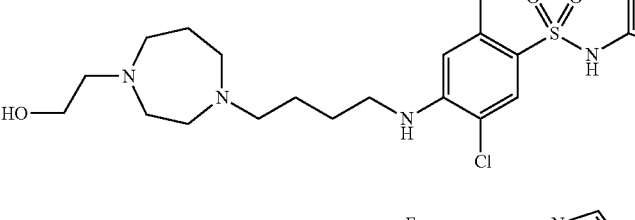 | 5-chloro-2-fluoro-4-({4-[4-(2-hydroxyethyl)-1,4-diazepan-1-yl]butyl}amino)-N-1,3-thiazol-2-ylbenzenesulfonamide | 506.1; 506.2 |
| 2-16 | 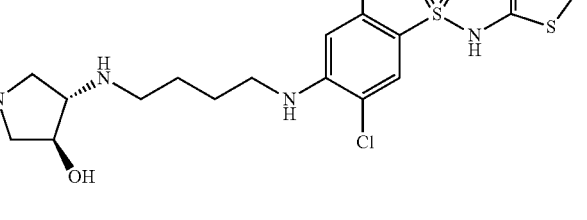 | 5-chloro-2-fluoro-N-(5-fluoro-1,3-thiazol-2-yl)-4-[(4-{[(3S,4S)-4-hydroxypyrrolidin-3-yl]amino}butyl)amino]benzenesulfonamide | 482.1; 482.1 |
| 2-17 | 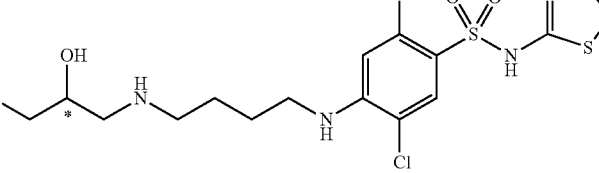 | 4-[(4-{[(2R or 2S)-3-amino-2-hydroxypropyl]amino}butyl)amino]-5-chloro-2-fluoro-N-(5-fluoro-1,3-thiazol-2-yl)benzenesulfonamide | 470.1; 470.2 |

TABLE 2-continued

| Exp No | Structure | Name | Exact Mass [M + H]+ calc; found |
|---|---|---|---|
| 2-18 | 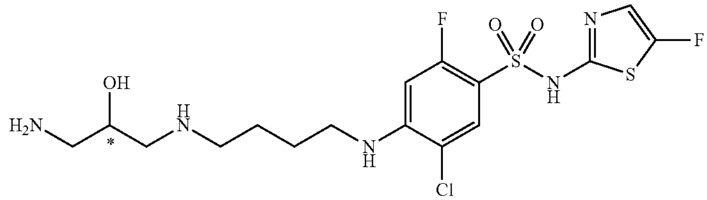 [SMILES: NCC(O)CNCCCCNc1cc(F)c(S(=O)(=O)Nc2ncc(F)s2)cc1Cl] | 4-[(4-{[(2S or 2R)-3-amino-2-hydroxypropyl]amino}butyl)amino]-5-chloro-2-fluoro-N-(5-fluoro-1,3-thiazol-2-yl)benzenesulfonamide | 470.1; 470.1 |
| 2-19 | 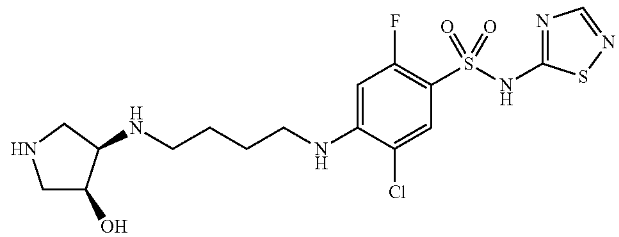 [SMILES: O=S(=O)(Nc1ncns1)c1cc(Cl)c(NCCCCN[C@@H]2CNC[C@@H]2O)cc1F] | 5-chloro-2-fluoro-4-[(4-{[(3R,4S)-4-hydroxypyrrolidin-3-yl]amino}butyl)amino]-N-1,2,4-thiadiazol-5-ylbenzenesulfonamide | 465.1; 465.2 |
| 2-20 | 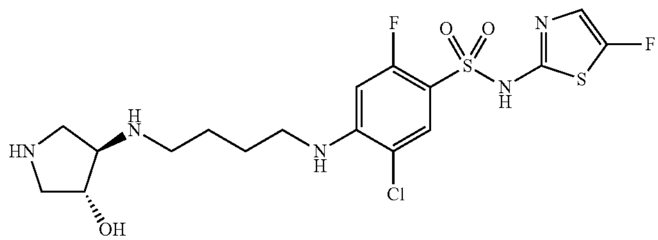 [SMILES: O=S(=O)(Nc1ncc(F)s1)c1cc(Cl)c(NCCCCN[C@@H]2CNC[C@H]2O)cc1F] | 5-chloro-2-fluoro-N-(5-fluoro-1,3-thiazol-2-yl)-4-[(4-{[(3R,4R)-4-hydroxypyrrolidin-3-yl]amino}butyl)amino]benzenesulfonamide | 482.1; 482.2 |
| 2-21 | 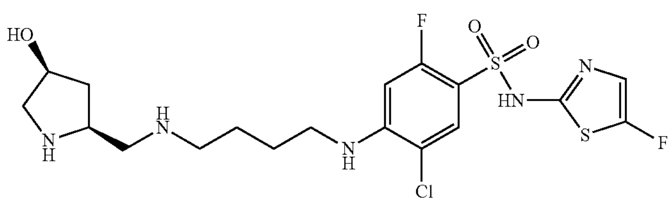 [SMILES: O=S(=O)(Nc1ncc(F)s1)c1cc(Cl)c(NCCCCNC[C@@H]2C[C@H](O)CN2)cc1F] | 5-chloro-2-fluoro-N-(5-fluoro-1,3-thiazol-2-yl)-4-{[4-({[(2S,4S)-4-hydroxypyrrolidin-2-yl]methyl}amino)butyl]amino}benzenesulfonamide | 496.1; 495.9 |
| 2-22 | 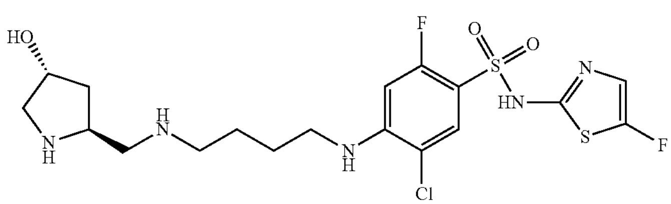 [SMILES: O=S(=O)(Nc1ncc(F)s1)c1cc(Cl)c(NCCCCNC[C@@H]2C[C@@H](O)CN2)cc1F] | 5-chloro-2-fluoro-N-(5-fluoro-1,3-thiazol-2-yl)-4-{[4-({[(2S,4R)-4-hydroxypyrrolidin-2-yl]methyl}amino)butyl]amino}benzenesulfonamide | 496.1; 496.0 |
| 2-23 | 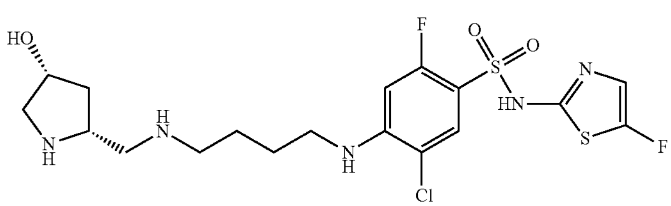 [SMILES: O=S(=O)(Nc1ncc(F)s1)c1cc(Cl)c(NCCCCNC[C@H]2C[C@@H](O)CN2)cc1F] | 5-chloro-2-fluoro-N-(5-fluoro-1,3-thiazol-2-yl)-4-{[4-({[(2R,4R)-4-hydroxypyrrolidin-2-yl]methyl}amino)butyl]amino}benzenesulfonamide | 496.1; 496.0 |

TABLE 2-continued

| Exp No | Structure | Name | Exact Mass [M + H]+ calc; found |
|---|---|---|---|
| 2-24 | 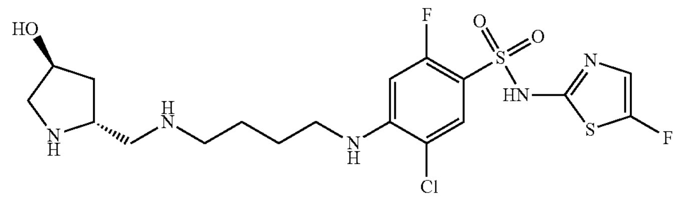 [SMILES: O=S(=O)(Nc1ncc(F)s1)c1cc(Cl)c(NCCCCNC[C@H]2C[C@H](O)CN2)cc1F] | 5-chloro-2-fluoro-N-(5-fluoro-1,3-thiazol-2-yl)-4-{[4-({[(2R,4S)-4-hydroxypyrrolidin-2-yl]methyl}amino)butyl]amino}benzenesulfonamide | 496.1; 496.0 |
| 2-25 | 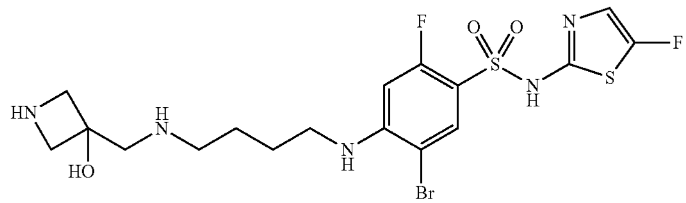 [SMILES: O=S(=O)(Nc1ncc(F)s1)c1cc(Br)c(NCCCCNCC2(O)CNC2)cc1F] | 5-bromo-2-fluoro-N-(5-fluoro-1,3-thiazol-2-yl)-4-[(4-{[(3-hydroxyazetidin-3-yl)methyl]amino}butyl)amino]benzenesulfonamide | 526.0; 526.1 |
| 2-26 | 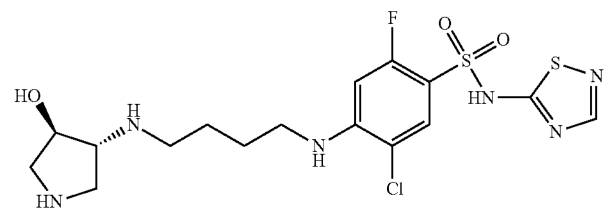 [SMILES: O=S(=O)(Nc1ncns1)c1cc(Cl)c(NCCCCN[C@@H]2CNC[C@H]2O)cc1F] | 5-chloro-2-fluoro-4-[(4-{[(3R,4R)-4-hydroxypyrrolidin-3-yl]amino}butyl)amino]-N-1,2,4-thiadiazol-5-ylbenzenesulfonamide | 465.1; 465.2 |
| 2-27 | 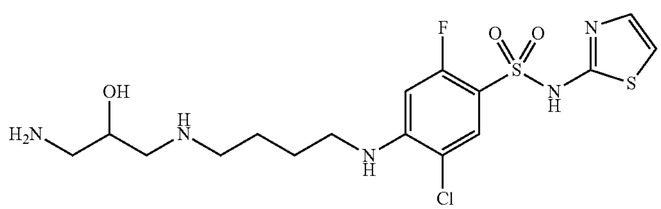 [SMILES: NCC(O)CNCCCCNc1cc(F)c(S(=O)(=O)Nc2nccs2)cc1Cl] | 4-({4-[(3-amino-2-hydroxypropyl)amino]butyl}amino)-5-chloro-2-fluoro-N-1,3-thiazol-2-ylbenzenesulfonamide | 452.1; 452.2 |
| 2-28 | 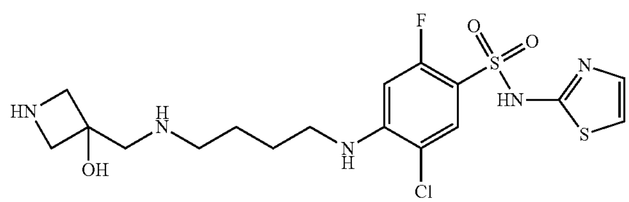 [SMILES: O=S(=O)(Nc1nccs1)c1cc(Cl)c(NCCCCNCC2(O)CNC2)cc1F] | 5-chloro-2-fluoro-4-[(4-{[(3-hydroxyazetidin-3-yl)methyl]amino}butyl)amino]-N-1,3-thiazol-2-ylbenzenesulfonamide | 464.1; 464.1 |
| 2-29 | 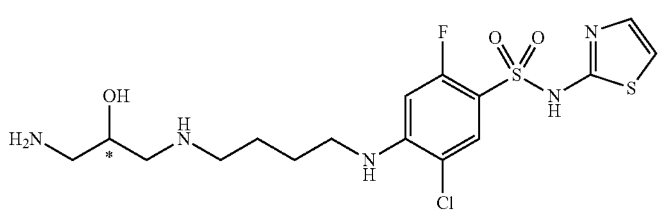 [SMILES: NCC(O)CNCCCCNc1cc(F)c(S(=O)(=O)Nc2nccs2)cc1Cl] | 4-[(4-{[(2R or 2S)-3-amino-2-hydroxypropyl]amino}butyl)amino]-5-chloro-2-fluoro-N-1,3-thiazol-2-ylbenzenesulfonamide | 452.1; 452.2 |
| 2-30 | 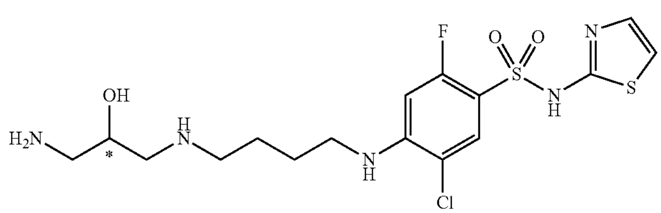 [SMILES: NCC(O)CNCCCCNc1cc(F)c(S(=O)(=O)Nc2nccs2)cc1Cl] | 4-[(4-{[(2S or 2R)-3-amino-2-hydroxypropyl]amino}butyl)amino]-5-chloro-2-fluoro-N-1,3-thiazol-2-ylbenzenesulfonamide | 452.1; 452.2 |

TABLE 2-continued

| Exp No | Structure | Name | Exact Mass [M + H]+ calc; found |
|---|---|---|---|
| 2-31 | 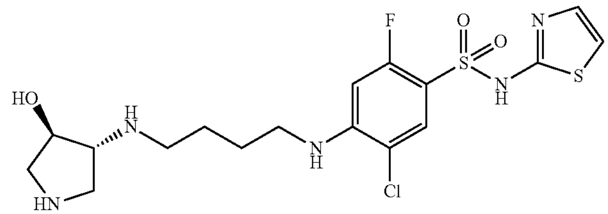 [SMILES: O=S(=O)(Nc1nccs1)c1cc(Cl)c(NCCCCN[C@@H]2CNC[C@H]2O)cc1F] | 5-chloro-2-fluoro-4-[(4-{[(3R,4R)-4-hydroxypyrrolidin-3-yl]amino}butyl)amino]-N-1,3-thiazol-2-ylbenzenesulfonamide | 464.1; 464.2 |
| 2-32 | 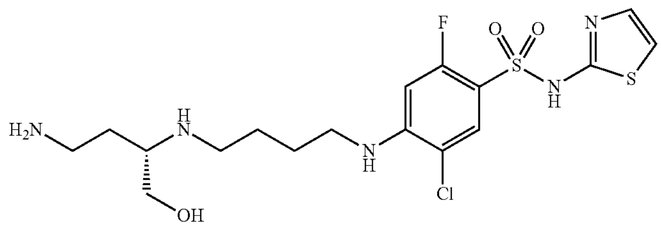 [SMILES: NCC[C@@H](CO)NCCCCNc1cc(F)c(S(=O)(=O)Nc2nccs2)cc1Cl] | 4-[(4-{[(1S)-3-amino-1-(hydroxymethyl)propyl]amino}butyl)amino]-5-chloro-2-fluoro-N-1,3-thiazol-2-ylbenzenesulfonamide | 466.1; 466.2 |
| 2-33 | 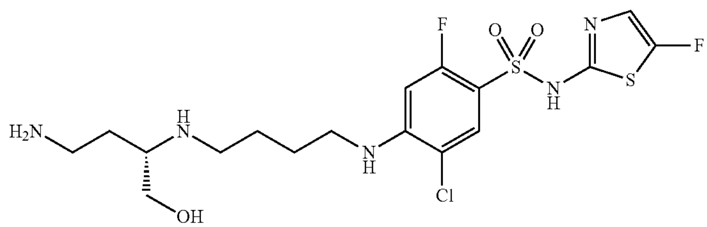 [SMILES: NCC[C@@H](CO)NCCCCNc1cc(F)c(S(=O)(=O)Nc2ncc(F)s2)cc1Cl] | 4-[(4-{[(1S)-3-amino-1-(hydroxymethyl)propyl]amino}butyl)amino]-5-chloro-2-fluoro-N-(5-fluoro-1,3-thiazol-2-yl)benzenesulfonamide | 484.1; 484.3 |
| 2-34 | 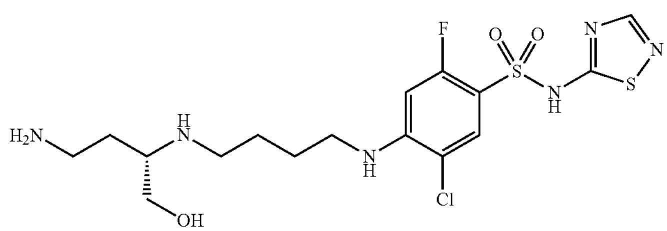 [SMILES: NCC[C@@H](CO)NCCCCNc1cc(F)c(S(=O)(=O)Nc2ncns2)cc1Cl] | 4-[(4-{[(1S)-3-amino-1-(hydroxymethyl)propyl]amino}butyl)amino]-5-chloro-2-fluoro-N-1,2,4-thiadiazol-5-ylbenzenesulfonamide | 467.1; 467.2 |
| 2-35 | 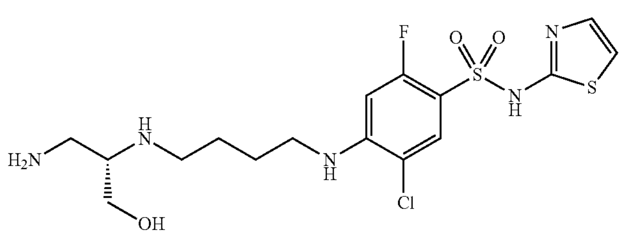 [SMILES: NC[C@@H](CO)NCCCCNc1cc(F)c(S(=O)(=O)Nc2nccs2)cc1Cl] | 4-[(4-{[(1S)-2-amino-1-(hydroxymethyl)ethyl]amino}butyl)amino]-5-chloro-2-fluoro-N-1,3-thiazol-2-ylbenzenesulfonamide | 452.1; 452.1 |
| 2-36 | 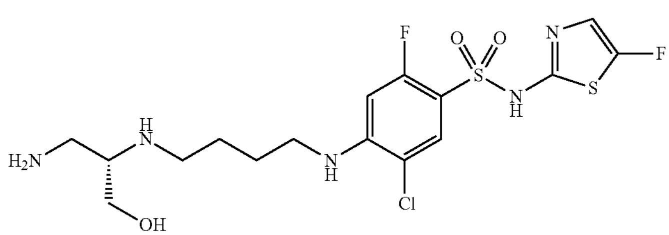 [SMILES: NC[C@@H](CO)NCCCCNc1cc(F)c(S(=O)(=O)Nc2ncc(F)s2)cc1Cl] | 4-[(4-{[(1S)-2-amino-1-(hydroxymethyl)ethyl]amino}butyl)amino]-5-chloro-2-fluoro-N-(5-fluoro-1,3-thiazol-2-yl)benzenesulfonamide | 470.1; 470.2 |

TABLE 2-continued

| Exp No | Name | Exact Mass [M + H]+ calc; found |
|---|---|---|
| 2-37 | 4-[(4-{[(1S)-2-amino-1-(hydroxymethyl)ethyl]amino}butyl)amino]-5-chloro-2-fluoro-N-1,2,4-thiadiazol-5-ylbenzenesulfonamide | 453.1; 453.1 |
| 2-38 | 5-chloro-2-fluoro-4-[(4-{[(3S,4S)-4-hydroxypyrrolidin-3-yl]amino}butyl)amino]-N-1,3-thiazol-2-ylbenzenesulfonamide | 464.1; 464.1 |
| 2-39 | 4-[(4-{[(1R)-2-amino-1-(hydroxymethyl)ethyl]amino}butyl)amino]-5-chloro-2-fluoro-N-1,3-thiazol-2-ylbenzenesulfonamide | 452.1; 452.2 |
| 2-40 | 4-[(4-{[(1R)-2-amino-1-(hydroxymethyl)ethyl]amino}butyl)amino]-5-chloro-2-fluoro-N-(5-fluoro-1,3-thiazol-2-yl)benzenesulfonamide | 470.1; 470.2 |
| 2-41 | 4-[(4-{[(1R)-2-amino-1-(hydroxymethyl)ethyl]amino}butyl)amino]-5-chloro-2-fluoro-N-1,2,4-thiadiazol-5-ylbenzenesulfonamide | 453.1; 453.1 |
| 2-42 | 5-bromo-2-fluoro-4-((4-(6-hydroxy-1,4-diazepan-1-yl)butyl)amino)-N-(1,2,4-thiadiazol-5-yl)benzenesulfonamide | 523.0; 523.1 |

TABLE 2-continued

| Exp No | Structure | Name | Exact Mass [M + H]+ calc; found |
|---|---|---|---|
| 2-43 | 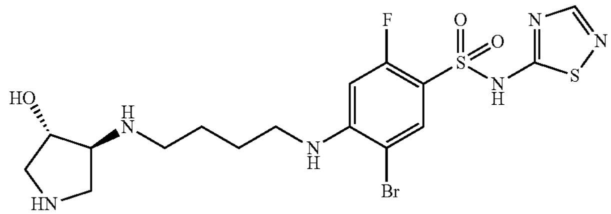 [SMILES: O=S(=O)(Nc1ncns1)c1cc(Br)c(NCCCCN[C@H]2CNC[C@@H]2O)cc1F] | 5-bromo-2-fluoro-4-((4-(((3S,4S)-4-hydroxypyrrolidin-3-yl)amino)butyl)amino)-N-(1,2,4-thiadiazol-5-yl)benzenesulfonamide | 509.0; 509.0 |
| 2-44 | 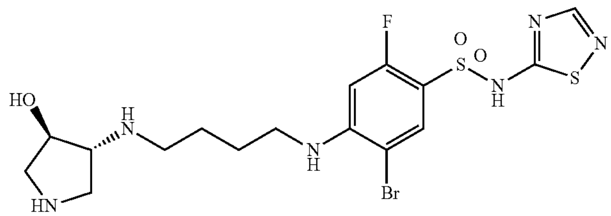 | 5-bromo-2-fluoro-4-((4-(((3R,4R)-4-hydroxypyrrolidin-3-yl)amino)butyl)amino)-N-(1,2,4-thiadiazol-5-yl)benzenesulfonamide | 509.0; 509.0 |

It will be appreciated that Examples 2-17 and 2-18 represent preparation of each of the following enantiomers isolated in substantially pure form:

and that Examples 2-29 and 2-30 represent preparation of each of the following enantiomers isolated in substantially pure form:

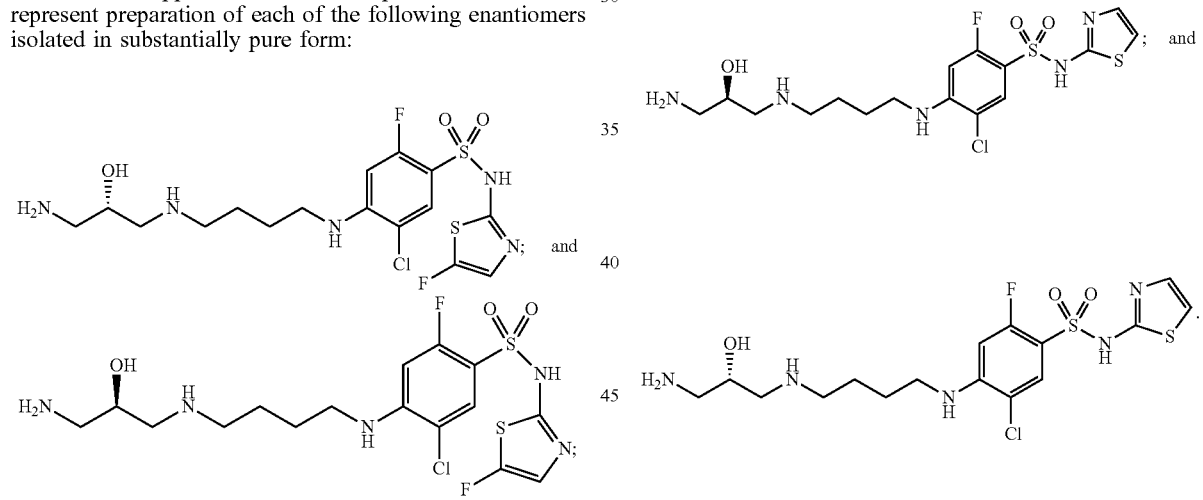

Example 3: (S)-5-chloro-4-((4-(((4,4-difluoropyrrolidin-2-yl)methyl)amino)butyl)amino)-2-fluoro-N-(thiazol-2-yl)benzenesulfonamide (Ex3-01)

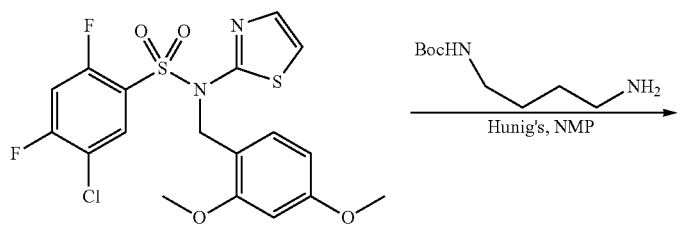

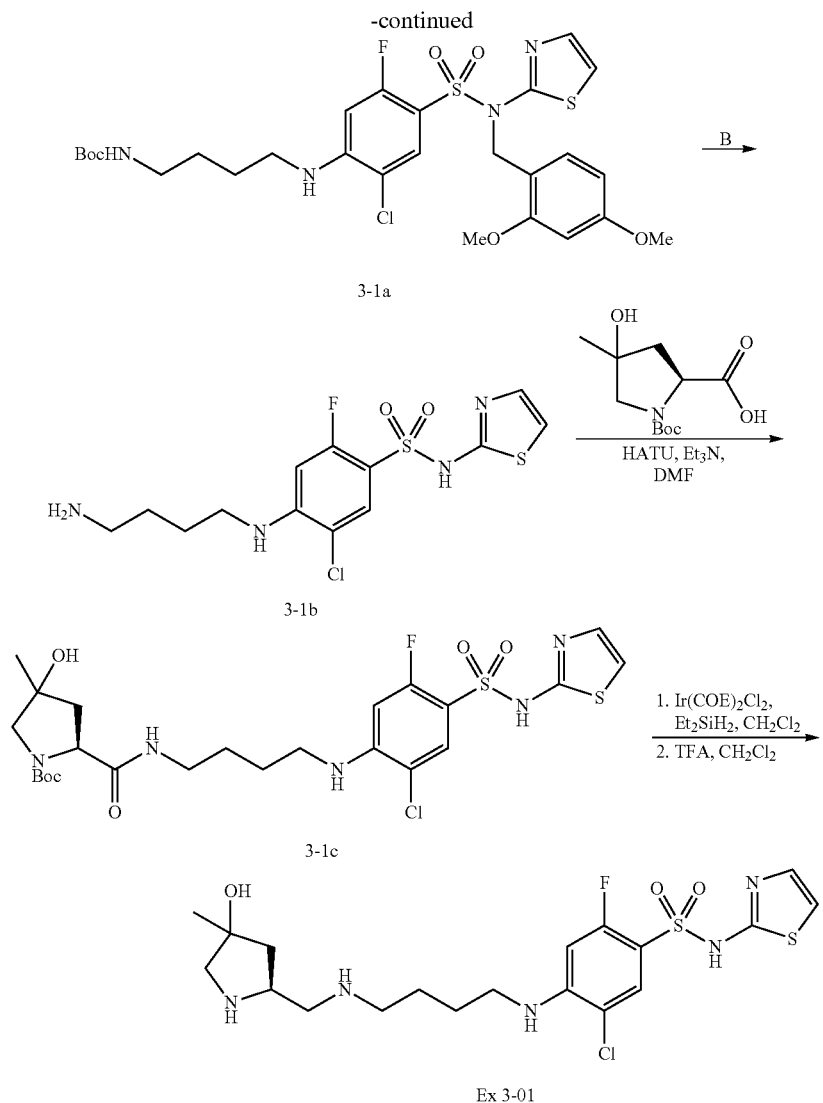

Step A. tert-butyl (4-((2-chloro-4-(N-(2,4-dimethoxybenzyl)-N-(thiazol-2-yl)sulfamoyl)-5-fluorophenyl)amino)butyl)carbamate (3-1a)

To a solution of 5-chloro-N-(2,4-dimethoxybenzyl)-2,4-difluoro-N-(thiazol-2-yl)benzenesulfonamide (2 g, 4.34 mmol) and tert-butyl (4-aminobutyl)carbamate (900 mg, 4.77 mmol) in NMP (21 mL) was added Hunig's base (2.3 mL, 13.02 mmol) at 25° C. The mixture was stirred at 70° C. in a sealed tube for 12 h. The mixture was then purified by prep-HPLC to give the desired product as yellow oil.
LRMS m/z (M+H) 629.6 found, 629.2 Calc'd.

Step B. 4-((4-aminobutyl)amino)-5-chloro-2-fluoro-N-(thiazol-2-yl)benzenesulfonamide (3-1b)

To a solution of 3-1a (2 g, 3.18 mmol) in DCM (32 mL) was added TFA (0.7 mL, 9.54 mmol) at 25° C. The mixture was stirred at 25° C. for 1 h. The mixture was then concentrated, suspended in MeOH and purified by SCX (50 g, eluting with 2 N NH$_3$ in MeOH) to give the desired product as a white solid.

$^1$H NMR (500 MHz, DMSO): δ 7.55 (d, J=7.2 Hz, 1H); 6.95 (d, J=3.9 Hz, 1H); 6.52 (s, 1H); 6.50 (s, 1H); 6.46 (d, J=3.9 Hz, 1H); 6.01 (s, 1H); 3.18 (m, 2H); 2.79 (m, 2H); 1.54 (m, 4H).
LRMS m/z (M+H) 379.5 found, 379.0 calc'd.

Step C. tert-butyl (2S)-2-((4-((2-chloro-5-fluoro-4-(N-(thiazol-2-yl)sulfamoyl)phenyl)amino)-butyl)carbamoyl)-4-hydroxy-4-methylpyrrolidine-1-carboxylate (3-1c)

To a solution of 3-1b (300 mg, 0.792 mmol (2S)-1-(tert-butoxycarbonyl)-4-hydroxy-4-methylpyrrolidine-2-carboxylic acid (194 mg, 0.792 mmol), and Et$_3$N (330 ul, 2.38 mmol) in DMF (3 mL) was added HATU (300 mg, 0.792 mmol). The reaction was stirred at rt for 1 h, quenched with 500 ul of water and extracted with 5 ml of EtOAc. The combined organic phase was concentrated and taken on to the next step.

Step D. 5-chloro-2-fluoro-4-((4-((((2S)-4-hydroxy-4-methylpyrrolidin-2-yl)methyl)amino)butyl)amino)-N-(thiazol-2-yl)benzenesulfonamide (3-1)

Chlorobis(cyclooctene)iridium(I) dimer (6.73 mg, 7.52 μmop was added to a uw vial containing diethylsilane (779 μl, 6.01 mmol) at rt. The mixture was stirred for 5 min, upon which time a solution of 3-1c (227 mg, 0.376 mmol) in DCM (375 uL) was added. The vial was sealed and heated to 80° C. for 2 h. The reaction was concentrated and then taken up in a 1:1 DCM:TFA (2 mL) solution and stirred for an additional 30 min at rt. The reaction was then concentrated and purified by prep-HPLC to give the desired product as a yellow oil.

$^1$H NMR (500 MHz, DMSO): δ 7.63 (m; 2H); 7.27 (d; J=4.6 Hz; 1H); 6.83 (d; J=4.6 Hz; 1H); 6.69 (d, J=12.89 Hz, 1H); 6.44 (m; 1H); 3.95 (m; 1H); 2.75-3.33 (m; 9H); 1.92 (m; 1H); 1.82 (m; 1H); 1.47-1.72 (m; 6H); 1.34 (s; 3H).

LRMS m/z (M+H) 492.3 found, 492.1 calc'd.

Synthesis of Selected Intermediate Compounds

Intermediate 1-1e: 5-chloro-N-(2,4-dimethoxybenzyl)-2,4-difluoro-N-(1,2,4-thiadiazol-5-yl) benzenesulfonamide

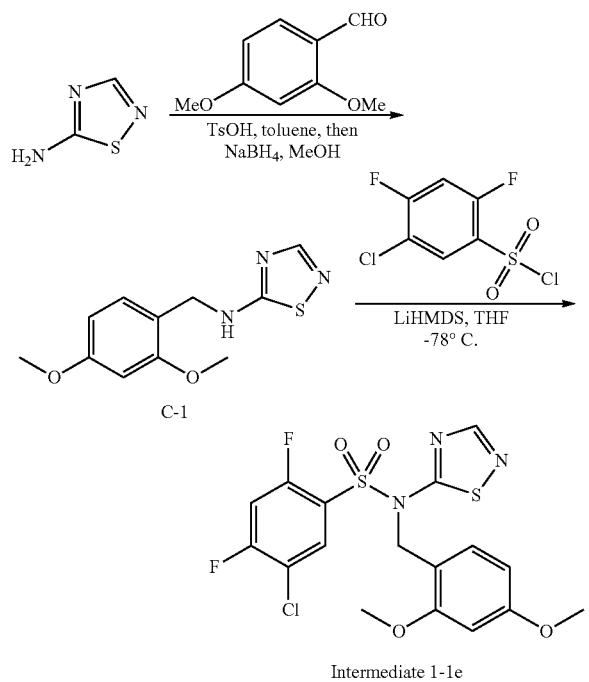

Step 1: N-(2,4-dimethoxybenzyl)-1,2,4-thiadiazol-5-amine (C-1)

Into a 20000-mL 4-necked round-bottom flask purged and maintained with an inert atmosphere of nitrogen was placed 1,2,4-thiadiazol-5-amine (300 g, 2.97 mol), 2,4-dimethoxybenzaldehyde (472 g, 2.84 mol, 1.05 equiv), p-TsOH (4.1 g, 23.8 mmol, 0.01 equiv), and toluene (9 L). The resulting solution was heated to reflux overnight with a water-separator. The reaction mixture was cooled to room temperature and concentrated under vacuum. The residue was washed with methanol. The resulting yellow solid was used crude in the next reaction. Into a 10-L 4-necked round-bottom flask purged and maintained with an inert atmosphere of nitrogen was placed a solution of the crude solid (550 g, 2.21 mol) in THF (5.5 L). This was followed by the addition of NaBH$_4$ (83 g, 2.25 mol) in several batches at 0° C. The resulting solution was stirred for 3 h at room temperature, then extracted with 3×1 L of ethyl acetate. The organic layers were combined, washed with 1×1000 mL of brine, dried over anhydrous magnesium sulfate and concentrated under vacuum. The residue was applied onto a silica gel column and eluted with dichloromethane/methanol (100:1) to give the title compound as a solid. $^1$H NMR (400 MHz, CDCl$_3$) δ 8.22 (s, 1H), 7.73 (t, J=7.6 Hz, 1H), 7.19 (d, J=8.4 Hz, 1H), 6.87 (t, J=8.4 Hz, 1H), 6.35 (dd, J=2.4, 6.0 Hz, 1H), 6.15 (d, J=2.0 Hz, 1H), 5.36 (s, 2H), 3.74 (s, 3H), 3.66 (s, 3H). MS m/z (M+H): 462.0.

Step 2: 5-chloro-N-(2,4-dimethoxybenzyl)-2,4-difluoro-N-(1,2,4-thiadiazol-5-yl) benzenesulfonamide To a mixture of C-1 (1.0 g, 4.0 mmol) in THF (20 mL) was added LiHMDS (5 mL, 5 mmol, 1M) at −78° C. under N$_2$. The mixture was warmed to room temperature and stirred for 1 h before cooled to −78° C. Then a solution of 5-chloro-2,4-difluorobenzene-1-sulfonyl chloride (1.2 g, 4.8 mmol) in THF (4 mL) was added dropwise. The mixture was stirred at room temperature for additional 1 h, then quenched with saturated NH$_4$Cl. The mixture was extracted with EtOAc and the combined organic phases were dried with Na$_2$SO$_4$, filtered and concentrated. The residue was purified by column chromatography on silica gel (PE:EtOAc=6:1) to afford the title compound. $^1$H NMR (400 MHz, CDCl$_3$) δ 8.22 (s, 1H), 7.73 (t, J=7.6 Hz, 1H), 7.19 (d, J=8.4 Hz, 1H), 6.87 (t, J=8.4 Hz, 1H), 6.35 (dd, J=2.4, 6.0 Hz, 1H), 6.15 (d, J=2.0 Hz, 1H), 5.36 (s, 2H), 3.74 (s, 3H), 3.66 (s, 3H). MS m/z (M+H): 462.0.

Intermediate 2: 5-bromo-N-(2,4-dimethoxybenzyl)-2,4-difluoro-N-(1,2,4-thiadiazol-5-yl)benzenesulfonamide

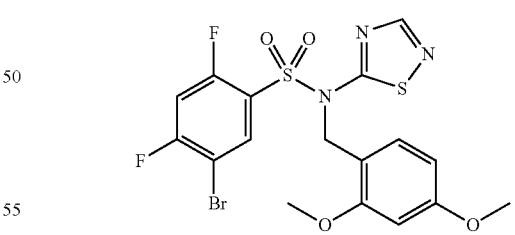

Intermediate 2 was synthesized using an analogous procedure to Intermediate 1-1e, Step 2, using 5-bromo-2,4-difluorobenzene-1-sulfonyl chloride. $^1$H NMR (400 MHz, CDCl$_3$): δ 8.24 (s, 1H), 7.89 (t, J=7.2 Hz, 1H), 7.21 (d, J=8.4 Hz, 1H), 6.85 (t, J=8.4 Hz, 1H), 6.35 (d, J=8.4 Hz, 1H), 6.16 (d, J=1.6 Hz, 1H), 5.37 (s, 2H), 2.99 (s, 3H), 3.03 (s, 3H).

Intermediate 3: N-(2,4-dimethoxybenzyl)-2,4-difluoro-N-(5-fluorothiazol-2-yl)-5-methylbenzenesulfonamide

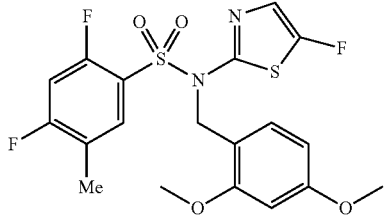 [SMILES: COc1ccc(CN(c2ncc(F)s2)S(=O)(=O)c2cc(C)c(F)cc2F)c(OC)c1]

Intermediate 3 was synthesized by an analogous procedure to Intermediate 1-1e, using 5-fluorothiazol-2-amine and 2,4-difluoro-5-methylbenzenesulfonyl chloride. $^1$H NMR (400 MHz, CDCl$_3$): δ 7.68 (t, J=7.6 Hz, 1H), 7.18 (d, J=8.4 Hz, 1H), 6.99 (d, J=2.4 Hz, 1H), 6.89 (t, J=9.2 Hz, 1H), 6.40-6.33 (m, 2H), 5.06 (s, 2H), 3.78 (s, 3H), 3.73 (s, 3H), 2.26 (s, 3H).

Intermediate 4: tert-butyl (2-bromo-4-(N-(3,4-dimethylbenzyl)-N-(1,2,4-thiadiazol-5-yl)sulfamoyl)-5-fluorophenyl)(4-oxobutyl)carbamate

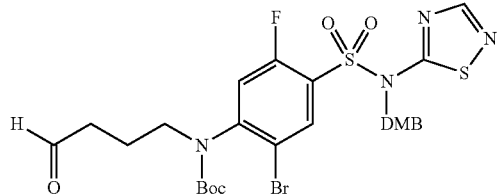

Intermediate 4 was prepared by analogy to Intermediate 2-1e in example 2-1, starting with Intermediate 2 (tert-butyl (2-bromo-4-(N-(3,4-dimethylbenzyl)-N-(1,2,4-thiadiazol-5-yl)sulfamoyl)-5-fluorophenyl)(4-oxobutyl)carbamate). $^1$H NMR (400 MHz, CDCl$_3$): δ 9.80 (s; 1H); 8.22 (s; 1H); 7.84 (d; J=6.8 Hz; 1H); 7.21 (d; J=8.4 Hz; 1H); 6.97 (d; J=9.2 Hz; 1H); 6.36-6.34 (m; 1H); 6.15 (s, 1H); 5.65 (br, s, 1H); 5.11 (br, s, 1H); 3.74 (s, 3H); 3.67 (s, 3H); 3.60 (br, s, 1H); 3.39 (br, s, 1H); 2.62-2.57 (m; 2H); 1.86-1.84 (m; 2H); 1.47-1.23 (br, s; 9H).

Intermediate 5: tert-butyl (2-chloro-4-(N-(3,4-dimethylbenzyl)-N-(thiazol-2-yl)sulfamoyl)-5-fluorophenyl)(4-oxobutyl)carbamate (L-005578859-000F)

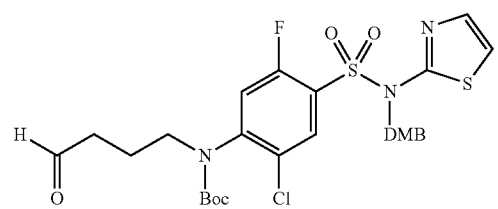

Intermediate 5 was prepared by analogy to Intermediate 2-1e in example 2-1, starting with 5-chloro-N-(2,4-dimethoxybenzyl)-2,4-difluoro-N-(thiazol-2-yl)benzenesulfonamide. LC-MS (ES, m/z): 650 [M+Na]$^+$; $^1$HNMR (400 MHz, DMSO): δ 9.66 (1H, s), 7.79~7.88 (2H, m), 7.47 (2H, m), 7.06 (1H, m), 6.44~6.48 (2H, m), 5.07 (2H, s), 3.70 (6H, d), 3.55 (2H, m), 1.68 (2H, m), 1.31 (9H, s).

Intermediate 6: tert-butyl (2-chloro-4-(N-(3,4-dimethylbenzyl)-N-(5-fluorothiazol-2-yl)sulfamoyl)-5-fluorophenyl)(4-oxobutyl)carbamate (L-005539256-000J)

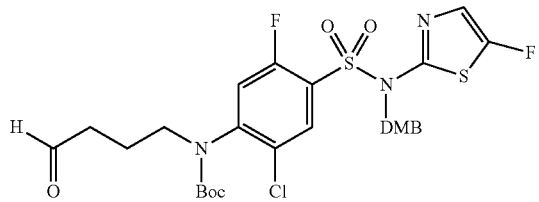

Intermediate 6 was prepared by analogy to Intermediate 2-1e in example 2-1, starting with 5-chloro-N-(2,4-dimethoxybenzyl)-2,4-difluoro-N-(5-fluorothiazol-2-yl)benzenesulfonamide. LC-MS (ES, m/z): 646 [M+H]$^+$; (400 MHz, CDCl$_3$): δ 1.25-1.57 (9H, m), 1.85 (2H, s), 2.54-2.55 (2H, d), 3.59 (2H, s), 3.73-3.86 (6H, m), 5.06 (2H, s), 6.33-6.39 (2H, m), 7.00-7.19 (3H, m), 7.83-7.85 (1H, d), 9.79 (1H, s).

Intermediate 7: tert-butyl (2-bromo-4-(N-(3,4-dimethylbenzyl)-N-(5-fluorothiazol-2-yl)sulfamoyl)-5-fluorophenyl)(4-oxobutyl)carbamate

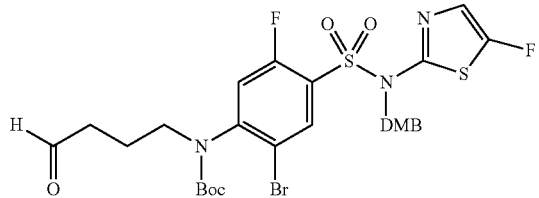

Intermediate 7 was prepared by analogy to Intermediate 2-1e in example 2-1, starting with 5-chloro-N-(2,4-dimethoxybenzyl)-2,4-difluoro-N-(thiazol-2-yl)benzenesulfonamide.
LCMS m/z (M+H) calc'd: 690.1. found (M+H): 690.2.

Intermediate 8: tert-butyl (S)-(3-amino-4-hydroxybutyl)carbamate

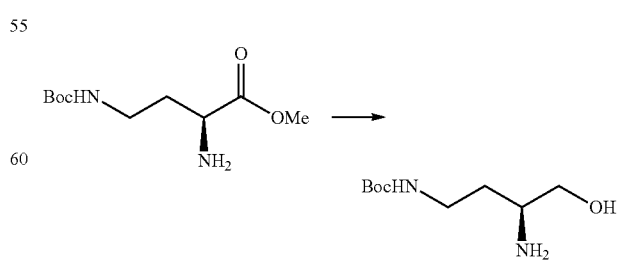

To a stirred solution of (S)-methyl 2-amino-4-((tert-butoxycarbonyl)amino)butanoate, HCl (300 mg, 1.116 mmol)

in THF (10 ml) was added DIBAL-H (5.58 ml, 5.58 mmol). The mixture was stirred at RT overnight. The reaction was quenched slowly with 1N NaOH, diluted with EtOAc. The organic phase was separated, dried and concentrated to give (S)-tert-butyl (3-amino-4-hydroxybutyl)carbamate. LCMS m/z (M+H) calc'd: 205.15. found (M+H): 205.06.

Intermediate 9: tert-butyl (R)-(2-amino-3-hydroxypropyl)carbamate

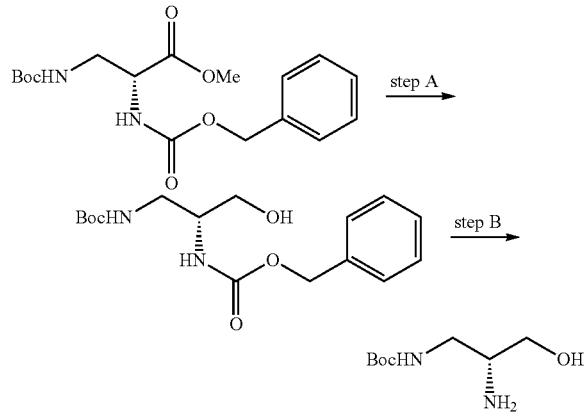

Step A: benzyl tert-butyl (3-hydroxypropane-1,2-diyl)(R)-dicarbamate

To a solution of (R)-methyl 2-(((benzyloxy)carbonyl)amino)-3-((tert-butoxycarbonyl)amino)propanoate, HCl (500 mg, 1.286 mmol) in DCM (10 ml) was added DIBAL-H (6.43 ml, 6.43 mmol). The mixture was stirred at RT overnight. The reaction was quenched slowly with 1N NaOH, diluted with DCM, washed with 1N NaOH. The organic phase was separated, dried and concentrated to give (R)-benzyl tert-butyl (3-hydroxypropane-1,2-diyl)dicarbamate. LCMS m/z (M+H) calc'd: 325.17. found (M+H): 325.28.

Step B: tert-butyl (R)-(2-amino-3-hydroxypropyl)carbamate

Pd—C (52.5 mg, 0.493 mmol) in a solution of (R)-benzyl tert-butyl (3-hydroxypropane-1,2-diyl)dicarbamate (160 mg, 0.493 mmol) and in MeOH (20 ml) was equipped with H2 balloon. The mixture was degassed thoroughly, then stirred at 25° C. under $H_2$ (balloon) for overnight. The mixture was filtered through a pad of celite, then concentrated in vacuo to give (R)-tert-butyl (2-amino-3-hydroxypropyl)carbamate. LCMS m/z (M+H) calc'd: 191.13. found (M+H): 191.19.

Intermediate 10: tert-butyl(S)-(2-amino-3-hydroxypropyl)carbamate

Intermediate 10 was synthesized analogous to Intermediate 9, starting with (S)-methyl 2-(((benzyloxy)carbonyl)amino)-3-((tert-butoxycarbonyl)amino)propanoate, HCl. LCMS m/z (M+H) calc'd: 191.13. found (M+H): 191.19.

IonWorks® Experimental Procedure

Compounds were tested on human Nav1.7 and Nav1.5 channels stably expressed in HEK 293 cells. Sodium current measurements on IonWorks Quattro: An automated patch-clamp assay on the IonWorks Quattro platform (Molecular Devices) was used to measure state-dependent inhibition of human Nav1.7 and 1.5 channels. Cells were sealed on a planar substrate using the Population Patch Plate (PPC) technology. Electrical access was obtained using both nystatin and amphotericin. A double-pulse protocol was used for the determination of $IC_{50}$ values for inactivated state block. Nav1.7 and Nav1.5 expressing cells were voltage clamped at −100 mV and −110 mV, respectively. A depolarizing prepulse to −10 mV (Nav1.7) or −30 mV (Nav1.5) for 1000 ms followed by a 10 ms repolarization to −100 mV (Nav1.7) or −110 mV (Nav1.5) was given to generate fractional channel inactivation of ~50%, followed by a 10 ms test pulse to −10 mV (Nav1.7) or −30 mV (Nav1.5) to measure peak current in control conditions and after compound addition. The following recording solutions were used (mM). External: 150 NaCl, 2 $CaCl_2$, 5 KCl, 1 Mg $Cl_2$, 10 HEPES, 12 Dextrose; internal: 120 CsF, 30 CsCl, 10 EGTA, 5 HEPES, 5 NaF, 2 $MgCl_2$.

For all electrophysiology experiments, offline analysis was used to determine percent inhibition as a function of drug concentration. $IC_{50}$ values were determined by fitting to the Hill equation.

The various compounds in Examples 1 through 4 and Tables 1 through 3 exemplified above were assayed for activity and selectivity using the foregoing IonWorks® technique. The results are reported in the following paragraph in a format expressing the identification of the compound with reference Example and compound (e.g. Ex 1-1 is Example 1, compound 1) followed by the observed potency in nM and the ratio of $Na_v1.7$ potency:$Na_v$ 1.5 potency as described here. Thus, Ex1-1: 1.7=50/ratio≥660 identifies compound Example 1, compound 1 as having 50 nM potency for the Nav 1.7 sodium ion channel (as measured by IonWorks®) and a ratio of 660 $Na_v$ 1.7:$Na_v$ 1.5 potency, determined by IonWorks® measurement. The following results are reported:

IonWorks® Data

EX 1-1: 1.7=50/ratio≥660; EX 1-2: 1.7=20/ratio≥1650; EX 1-4: 1.7=39/ratio≥846; EX 1-5: 1.7=19/ratio≥1737; EX 1-6: 1.7=15/ratio≥2200; EX 1-7: 1.7=7.0/ratio≥4714; EX 1-8: 1.7=17/ratio≥1941; EX 1-9: 1.7=55/ratio≥600; EX 1-11: 1.7=6.6/ratio≥5000; EX 2-1: 1.7=16/ratio≥2063; EX 2-2: 1.7=23/ratio≥1435; EX 2-4: 1.7=35/ratio≥943; EX 2-6: 1.7=14/ratio≥2357; EX 2-9: 1.7=29/ratio≥1138; EX 2-16: 1.7=32/ratio≥1031; EX 2-17: 1.7=15/ratio≥2200; EX 2-18: 1.7=16/ratio≥1000; EX 2-20: 1.7=40/ratio≥825; EX 2-21: 1.7=32/ratio≥344; EX 2-22: 1.7=35/ratio≥942; EX 2-23: 1.7=23/ratio≥1435; EX 2-24: 1.7=30/ratio≥1100; EX 2-25: 1.7=15/ratio≥2200; EX 2-28: 1.7=18/ratio≥1833; EX 2-29: 1.7=18/ratio≥1833; EX 2-30: 1.7=17/ratio≥1941; EX 2-31: 1.7=30/ratio≥1100; EX 2-32: 1.7=19/ratio≥1737; EX 2-33: 1.7=20/ratio≥1650; EX 2-34: 1.7=18/ratio≥1833; EX 2-35: 1.7=15/ratio≥2200; EX 2-36: 1.7=24/ratio≥1375; EX 2-37: 1.7=27/ratio≥1222; EX 2-38: 1.7=40/ratio≥825; EX 2-39: 1.7=60/ratio≥550; EX 2-40: 1.7=50/ratio≥660; EX 2-41:

1.7=29/ratio≥655; EX 2-42: 1.7=160/ratio≥200; EX 2-43: 1.7=15/ratio≥2200; EX 2-44: 1.7=25/ratio≥1300; EX 3-1: 1.7=100/ratio≥330.

What is claimed is:

1. A compound, or a pharmaceutically acceptable salt thereof, having the structure of Formula A:

Formula A wherein:
- $R^1$ is: —Cl, —Br, or linear, branched or cyclic alkyl of up to 3 carbon atoms;
- $R^2$ is:
  - (a) a moiety of the formula:

wherein, one of $R^{3a}$ and $R^{3b}$ is H and the other is —H, —F, $CH_3$; or
  - (b) a moiety of the formula:

and
- E is:
  - (I) a moiety of Formula $E^1$:

Formula $E^1$ wherein:
  - $R^6$ is —H or a linear, branched or cyclic alkyl of up to 6 carbon atoms; and
  - B is:
    - (a) a moiety of the formula:

which moiety is bonded to nitrogen at one of $R^{7A}$, $R^{7B}$, or $R^{7C}$ via —$CH_2$—, or is bonded to nitrogen directly at one of $R^{7C}$, and wherein:
- m is 0, 1 or 2;
- $R^{7A}$ and $R^{7B}$ are independently for each occurrence —H, or a linear, branched or cyclic alkyl of up to 3 carbon atoms when not selected to be bonded to the nitrogen via methylene;
- $R^{7C}$ when not selected to be bonded to the nitrogen directly or via methylene is independently for each occurrence: (i) —H; (ii) linear, branched, or cyclic alkyl of up to three carbon atoms; and
- $R^{7D}$ is: (ai) —H; or (aii) a linear, branched or cyclic alkyl of up to 5 carbon atoms; or (b) a moiety of the formula:

wherein:
- $R^{7h}$ is —H or a linear, branched or cyclic alkyl of up to 3 carbon atoms; and
- $R^{7g}$ and $R^{7f}$ are selected as follows:
  - (i) $R^{7g}$ is a linear alkyl of 2 to 4 carbon atoms, a branched alkyl of 3 to 6 carbon atoms or cyclic alkyl of up to 6 carbon atoms and $R^{7f}$ is a linear alkyl of 2 to 4 carbon atoms, or a branched or cyclic alkyl of up to 6 carbon atoms which is substituted with —OH on one carbon atom thereof that is bonded beta to, or further from, the nitrogen to which it is attached; or
  - (ii) $R^{7f}$ is —H or a linear, branched or cyclic alkyl of up 6 carbon atoms and $R^{7g}$ is —$(CH_2)_{1-2}$—(HC(OH))—$(CH_2)_{1-2}$;

(II) a moiety of Formula $E^2$:

Formula $E^2$ wherein each $R^8$ is independently —H or linear, branched, or cyclic alkyl of up to 6 carbon atoms; or (III) a moiety of Formula $E^3$:

Formula $E^3$ wherein:
R$^{9A}$ is independently for each occurrence: (i) —H; (ii) —OH; or (iii) a linear, branched or cyclic alkyl of up to 6 carbon atoms which is optionally substituted on one carbon atom there of with an —OH;
R$^{10A}$ is independently for each occurrence: (i) —H; or (ii) linear, branched or cyclic alkyl of up to 6 carbon atoms which is optionally substituted on one carbon atom thereof with an —OH;
R$^{11A}$ is —H or an alkyl of 2 or 3 carbons which is optionally substituted on a beta or gamma carbon with an —OH,
with the proviso that only one —OH substituent is present among all of R$^{9A}$, R$^{10A}$, and R$^{11A}$.

2. A compound of claim 1, or a pharmaceutically acceptable salt thereof, wherein E has the structure of Formula E$^1$:

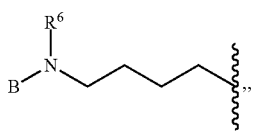

Formula E$^1$ wherein:
R$^6$ is —H or a linear, branched or cyclic alkyl of up to 6 carbon atoms; and
B is:

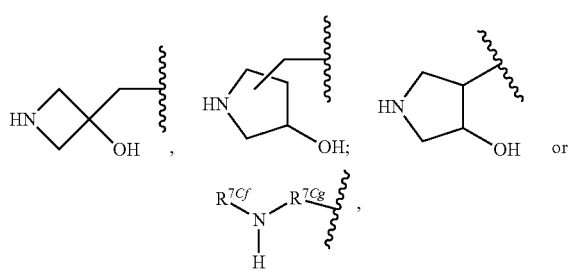

wherein:
(a) R$^{7Cg}$ is —CH$_2$—CH(OH)—CH$_2$— and R$^{7Cf}$ is —H or a linear alkyl of 2 to 4 carbon atoms or a branched or cyclic alkyl of up to 6 carbon atoms; or
(b) R$^{7Cg}$ is linear alkyl of 2 to 4 carbon atoms, branched alkyl of 3 to 6 carbon atoms or cyclic alkyl of up to 6 carbon atoms and R$^{7Cf}$ is linear, branched, or cyclic alkyl of up to 6 carbon atoms that is substituted on one carbon thereof which is beta or further from the nitrogen with —OH.

3. A compound of claim 1, or a pharmaceutically acceptable salt thereof, having the structure of Formula AI:

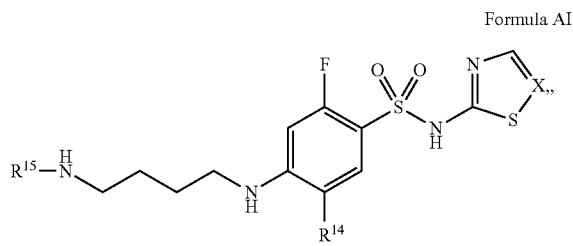

Formula AI wherein:
X is —N= or —C(R$^{C14c}$)=, wherein R$^{C14c}$ is —H, —F, or —CH$_3$;
R$^{14}$ is —Cl or —Br; and
R$^{15}$ is a moiety of Formula AIb bonded to nitrogen via methylene through one of R$^{15b}$, R$^{15c}$, or R$^{15d}$, or bonded directly to nitrogen through R$^{15c}$ if present:

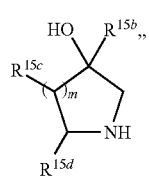

Formula AIb wherein:
m is 0 or 1;
R$^{15c}$, when present and not selected to be bonded to nitrogen is, independently: (i) —H; or (ii) linear, branched or cyclic alkyl of up to 3 carbon atoms; and
R$^{15b}$ and R$^{15d}$, when not selected to be bonded to nitrogen are, independently: (i) —H; or (ii) linear, branched or cyclic alkyl of up to 3 carbon atoms.

4. A compound of claim 1, or a pharmaceutically acceptable salt thereof, having the structure of Formula AI:

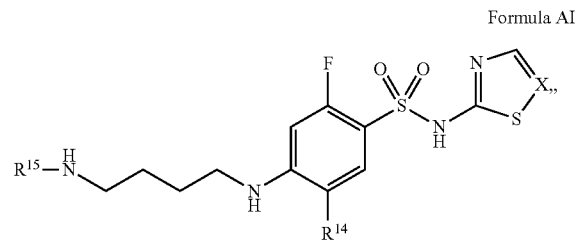

Formula AI wherein:
X is —N= or —C(R$^{C14c}$)=, wherein R$^{C14c}$ is —H, —F, or —CH$_3$;
R$^{14}$ is —Cl or —Br; and
R$^{15}$ is a moiety of the formula:

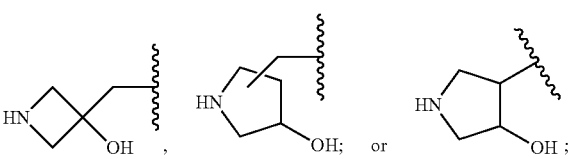

or

H$_2$N—CH$_2$—CH(OH)—CH$_2$—.

5. A compound of claim 1, or a pharmaceutically acceptable salt thereof, having the structure:

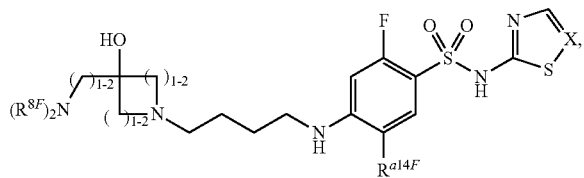

wherein:
X is —N= or —C(R^{C14e})=, wherein R^{C14e} is —H, —F, or —CH$_3$;
R^{a14F} is —Cl, —Br or —CH$_3$; and
R^{8F} is independently —H or linear, branched, or cyclic alkyl of up to 6 carbon atoms.

6. A composition comprising at least one compound of claim 1, or a pharmaceutically acceptable salt thereof, and at least one pharmaceutically acceptable excipient.

7. A pharmaceutical composition of claim 6 comprising additionally an effective amount of at least one other pharmaceutically active ingredient which is: (i) an opioid agonist or antagonist; (ii) a calcium channel antagonist; (iii) an NMDA receptor agonist or antagonist; (iv) a COX-2 selective inhibitor; (v) an NSAID (non-steroidal anti-inflammatory drug); or (vi) paracetamol (APAP, acetaminophen), and a pharmaceutically acceptable carrier.

8. The composition of claim 6 that provides an amount of said compound of claim 1, or a pharmaceutically acceptable salt thereof, which is sufficient to provide a therapeutic response in a subject in need of therapy for a pain disorder, cough, or acute itch or chronic itch disorder.

9. A method of treating a pain disorder, or cough, or acute itch or chronic itch disorder comprising administering to a patient in need thereof a therapeutically effective amount of the composition of claim 6.

10. The method of claim 9 wherein said disorder is an acute pain, inflammatory pain or neuropathic pain disorder.

11. A compound, or a pharmaceutically acceptable salt thereof, which is:

4-[(4-{[(2S)-3-amino-2-hydroxypropyl]amino}butyl) amino]-5-chloro-2-fluoro-N-1,2,4-thiadiazol-5-ylbenzenesulfonamide;
4-[(4-{[3-amino-2-hydroxypropyl]amino}butyl)amino]-5-chloro-2-fluoro-N-1,2,4-thiadiazol-5-ylbenzenesulfonamide;
4-({4-[3-(aminomethyl)-3-hydroxyazetidin-1-yl]butyl}amino)-5-chloro-2-fluoro-N-(5-fluoro-1,3-thiazol-2-yl)benzenesulfonamide;
4-({4-[3-(aminomethyl)-3-hydroxyazetidin-1-yl]butyl}amino)-5-chloro-2-fluoro-N-1,2,4-thiadiazol-5-ylbenzenesulfonamide;
2-fluoro-N-(5-fluoro-1,3-thiazol-2-yl)-4-[(4-{[(3-hydroxyazetidin-3-yl)methyl]amino}butyl)amino]-5-methylbenzenesulfonamide;
5-bromo-2-fluoro-4-[(4-{[(3-hydroxyazetidin-3-yl)methyl]amino}butyl)amino]-N-1,2,4-thiadiazol-5-yl-benzenesulfonamide;
4-[(4-{[(2R)-3-amino-2-hydroxypropyl]-amino}butyl) amino]-5-chloro-2-fluoro-N-1,2,4-thiadiazol-5-yl-benzenesulfonamide;
4-[(4-{[(2S)-3-amino-2-hydroxypropyl]-amino}butyl) amino]-5-bromo-2-fluoro-N-1,2,4-thiadiazol-5-yl-benzenesulfonamide;
4-[(4-{[(2R)-3-amino-2-hydroxypropyl]-amino}-butyl) amino]-5-bromo-2-fluoro-N-1,2,4-thiadiazol-5-yl-benzenesulfonamide;
4-[(4-{[3-amino-2-hydroxypropyl]-amino}-butyl) amino]-5-bromo-2-fluoro-N-1,2,4-thiadiazol-5-yl-benzenesulfonamide;
5-chloro-2-fluoro-4-[(4-{[(3-hydroxyazetidin-3-yl) methyl]amino}butyl)amino]-N-(4-methyl-1,3-thiazol-2-yl)-benzenesulfonamide;
5-chloro-2-fluoro-4-[(4-{[(3-hydroxyazetidin-3-yl) methyl]amino}butyl)amino]-N-1,2,4-thiadiazol-5-yl-benzenesulfonamide;
5-chloro-2-fluoro-4-[(4-{[(3R,4R)-4-hydroxypyrrolidin-3-yl]amino}butyl)amino]-N-1,2,4-thiadiazol-5-ylbenzenesulfonamide;
5-chloro-2-fluoro-4-{[4-({3-[(2-hydroxyethyl)amino] propyl}amino)butyl]amino}-N-1,2,4-thiadiazol-5-yl-benzenesulfonamide;
5-chloro-2-fluoro-4-{[4-({2-[(2-hydroxyethyl)amino] ethyl}amino)butyl]amino}-N-1,2,4-thiadiazol-5-yl-benzenesulfonamide;
4-({4-[(3-amino-2-hydroxypropyl)amino]butyl}amino)-5-chloro-2-fluoro-N-1,2,4-thiadiazol-5-ylbenzenesulfonamide;
5-chloro-2-fluoro-N-(5-fluoro-1,3-thiazol-2-yl)-4-[(4-{[(3-hydroxyazetidin-3-yl)-methyl]amino}butyl) amino]benzenesulfonamide;
5-chloro-2-fluoro-4-[(4-{[(3S,4 S)-4-hydroxypyrrolidin-3-yl]amino}butyl)amino]-N-1,2,4-thiadiazol-5-ylbenzenesulfonamide;
5-chloro-2-fluoro-N-(5-fluoro-1,3-thiazol-2-yl)-4-{[4-({2-[(2-hydroxy-1,1-dimethylethyl)-amino]-1,1-dimethylethyl}amino)butyl]amino)}benzenesulfonamide;
5-chloro-2-fluoro-N-(5-fluoro-1,3-thiazol-2-yl)-4-{[4-({2-[(2-hydroxyethyl)amino]-ethyl}amino)butyl] amino}benzenesulfonamide;
4-({4-[(3-amino-2-hydroxypropyl)amino]butyl}amino)-5-chloro-2-fluoro-N-(5-fluoro-1,3-thiazol-2-yl)benzenesulfonamide;
5-chloro-2-fluoro-4-({4-[7-(hydroxymethyl)-1,4-diazepan-1-yl]butyl}amino)-N-1,3-thiazol-2-ylbenzenesulfonamide;
5-chloro-2-fluoro-4-({4-[2-(2-hydroxyethyl)-1,4-diazepan-1-yl]butyl}amino)-N-1,3-thiazol-2-ylbenzenesulfonamide;
5-chloro-2-fluoro-4-({4-[2-(hydroxymethyl)-1,4-diazepan-1-yl]butyl}amino)-N-1,3-thiazol-2-ylbenzenesulfonamide;
5-chloro-2-fluoro-4-{[4-(6-hydroxy-6-methyl-1,4-diazepan-1-yl]butyl]amino}-N-1,3-thiazol-2-ylbenzenesulfonamide;
5-chloro-2-fluoro-4-({4-[4-(2-hydroxyethyl)-1,4-diazepan-1-yl]butyl}amino)-N-1,3-thiazol-2-ylbenzenesulfonamide;
5-chloro-2-fluoro-N-(5-fluoro-1,3-thiazol-2-yl)-4-[(4-{[(3S,4S)-4-hydroxypyrrolidin-3-yl]amino}butyl) amino]benzenesulfonamide;
4-[(4-{[(2R)-3-amino-2-hydroxypropyl]amino}butyl) amino]-5-chloro-2-fluoro-N-(5-fluoro-1,3-thiazol-2-yl)benzenesulfonamide;
4-[(4-{[(2S)-3-amino-2-hydroxypropyl]amino}butyl) amino]-5-chloro-2-fluoro-N-(5-fluoro-1,3-thiazol-2-yl)benzenesulfonamide;
4-[(4-{[3-amino-2-hydroxypropyl]amino}butyl)amino]-5-chloro-2-fluoro-N-(5-fluoro-1,3-thiazol-2-yl)benzenesulfonamide;
5-chloro-2-fluoro-4-[(4-{[(3R,4 S)-4-hydroxypyrrolidin-3-yl]amino}butyl)amino]-N-1,2,4-thiadiazol-5-ylbenzenesulfonamide;

5-chloro-2-fluoro-N-(5-fluoro-1,3-thiazol-2-yl)-4-[(4-{[(3R,4R)-4-hydroxypyrrolidin-3-yl]amino}butyl)amino]benzenesulfonamide;
5-chloro-2-fluoro-N-(5-fluoro-1,3-thiazol-2-yl)-4-{[4-({[(2 S,4 S)-4-hydroxypyrrolidin-2-yl]methyl}amino)butyl]amino}benzenesulfonamide;
5-chloro-2-fluoro-N-(5-fluoro-1,3-thiazol-2-yl)-4-{[4-({[(2 S,4R)-4-hydroxypyrrolidin-2-yl]methyl}amino)butyl]amino}benzenesulfonamide;
5-chloro-2-fluoro-N-(5-fluoro-1,3-thiazol-2-yl)-4-{[4-({[(2R,4R)-4-hydroxypyrrolidin-2-yl]methyl}amino)butyl]amino}benzenesulfonamide;
5-chloro-2-fluoro-N-(5-fluoro-1,3-thiazol-2-yl)-4-{[4-({[(2R,4 S)-4-hydroxypyrrolidin-2-yl]methyl}amino)butyl]amino}benzenesulfonamide;
5-bromo-2-fluoro-N-(5-fluoro-1,3-thiazol-2-yl)-4-[(4-{[(3-hydroxyazetidin-3-yl)methyl]amino}butyl)amino]benzenesulfonamide;
5-chloro-2-fluoro-4-[(4-{[(3R,4R)-4-hydroxypyrrolidin-3-yl]amino}butyl)amino]-N-1,2,4-thiadiazol-5-ylbenzenesulfonamide;
4-({4-[(3-amino-2-hydroxypropyl)amino]butyl}amino)-5-chloro-2-fluoro-N-1,3-thiazol-2-ylbenzenesulfonamide;
5-chloro-2-fluoro-4-[(4-{[(3-hydroxyazetidin-3-yl)methyl]amino}butyl)amino]-N-1,3-thiazol-2-ylbenzenesulfonamide;
4-[(4-{[(2R)-3-amino-2-hydroxypropyl]amino}butyl)amino]-5-chloro-2-fluoro-N-1,3-thiazol-2-ylbenzenesulfonamide;
4-[(4-{[(2S)-3-amino-2-hydroxypropyl]amino}butyl)amino]-5-chloro-2-fluoro-N-1,3-thiazol-2-ylbenzenesulfonamide;
4-[(4-{[3-amino-2-hydroxypropyl]amino}butyl)amino]-5-chloro-2-fluoro-N-1,3-thiazol-2-ylbenzenesulfonamide;
5-chloro-2-fluoro-4-[(4-{[(3R,4R)-4-hydroxypyrrolidin-3-yl]amino}butyl)amino]-N-1,3-thiazol-2-ylbenzenesulfonamide;
4-[(4-{[(1S)-3-amino-1-(hydroxymethyl)propyl]amino}butyl)amino]-5-chloro-2-fluoro-N-1,3-thiazol-2-ylbenzenesulfonamide;
4-[(4-{[(1S)-3-amino-1-(hydroxymethyl)propyl]amino}butyl)amino]-5-chloro-2-fluoro-N-(5-fluoro-1,3-thiazol-2-yl)benzenesulfonamide;
4-[(4-{[(1S)-3-amino-1-(hydroxymethyl)propyl]amino}butyl)amino]-5-chloro-2-fluoro-N-1,2,4-thiadiazol-5-ylbenzenesulfonamide;
4-[(4-{[(1S)-2-amino-1-(hydroxymethyl)ethyl]amino}butyl)amino]-5-chloro-2-fluoro-N-1,3-thiazol-2-ylbenzenesulfonamide;
4-[(4-{[(1S)-2-amino-1-(hydroxymethyl)ethyl]amino}butyl)amino]-5-chloro-2-fluoro-N-(5-fluoro-1,3-thiazol-2-yl)benzenesulfonamide;
4-[(4-{[(1S)-2-amino-1-(hydroxymethyl)ethyl]amino}butyl)amino]-5-chloro-2-fluoro-N-1,2,4-thiadiazol-5-ylbenzenesulfonamide;
5-chloro-2-fluoro-4-[(4-{[(3S,4S)-4-hydroxypyrrolidin-3-yl]amino}butyl)amino]-N-1,3-thiazol-2-ylbenzenesulfonamide;
4-[(4-{[(1R)-2-amino-1-(hydroxymethyl)ethyl]amino}butyl)amino]-5-chloro-2-fluoro-N-1,3-thiazol-2-ylbenzenesulfonamide;
4-[(4-{[(1R)-2-amino-1-(hydroxymethyl)ethyl]amino}butyl)amino]-5-chloro-2-fluoro-N-(5-fluoro-1,3-thiazol-2-yl)benzenesulfonamide;
5-bromo-2-fluoro-4-((4-(6-hydroxy-1,4-diazepan-1-yl)butyl)amino)-N-(1,2,4-thiadiazol-5-yl)benzenesulfonamide;
5-bromo-2-fluoro-4-((4-(((3S,4S)-4-hydroxypyrrolidin-3-yl)amino)butyl)amino)-N-(1,2,4-thiadiazol-5-yl)benzenesulfonamide;
5-bromo-2-fluoro-4-((4-(((3R,4R)-4-hydroxypyrrolidin-3-yl)amino)butyl)amino)-N-(1,2,4-thiadiazol-5-yl)benzenesulfonamide;
4-((4-(3-(aminomethyl)-3-hydroxyazetidin-1-yl)butyl)amino)-5-bromo-2-fluoro-N-(1,2,4-thiadiazol-5-yl)benzenesulfonamide;
4-[(4-{[(1R)-2-amino-1-(hydroxymethyl)ethyl]amino}butyl)amino]-5-chloro-2-fluoro-N-1,2,4-thiadiazol-5-ylbenzenesulfonamide; or
5-chloro-2-fluoro-4-[(4-{[(4-hydroxy-4-methylpyrrolidin-2-yl)methyl]amino}butyl)-amino]-N-1,3-thiazol-2-ylbenzenesulfonamide.

12. A compound selected from the group consisting of:

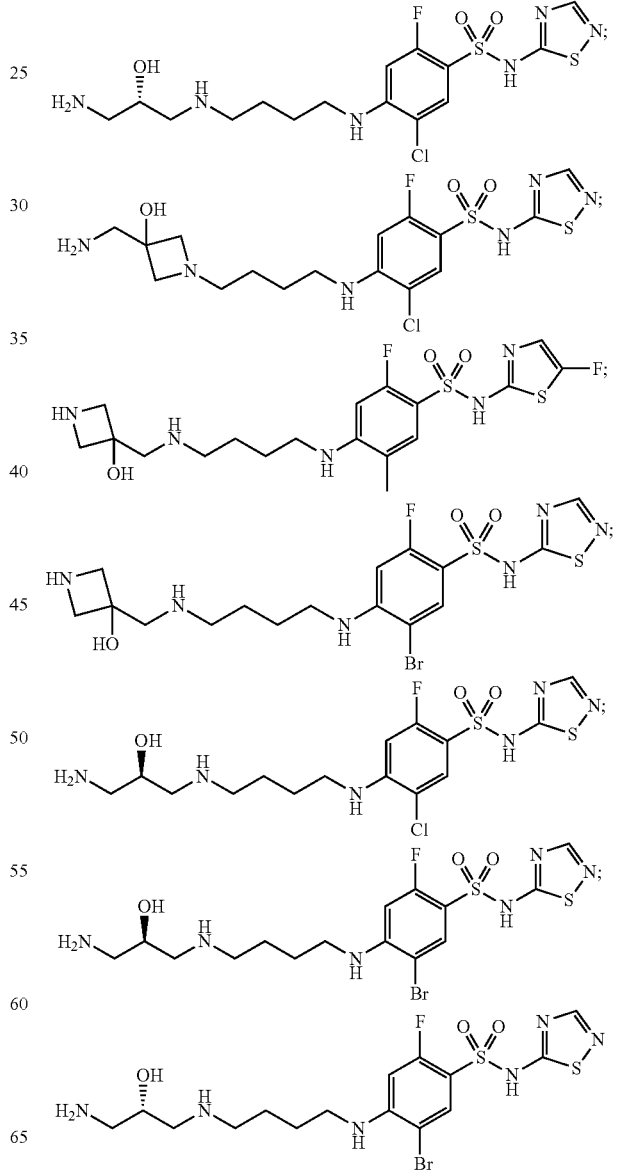

-continued

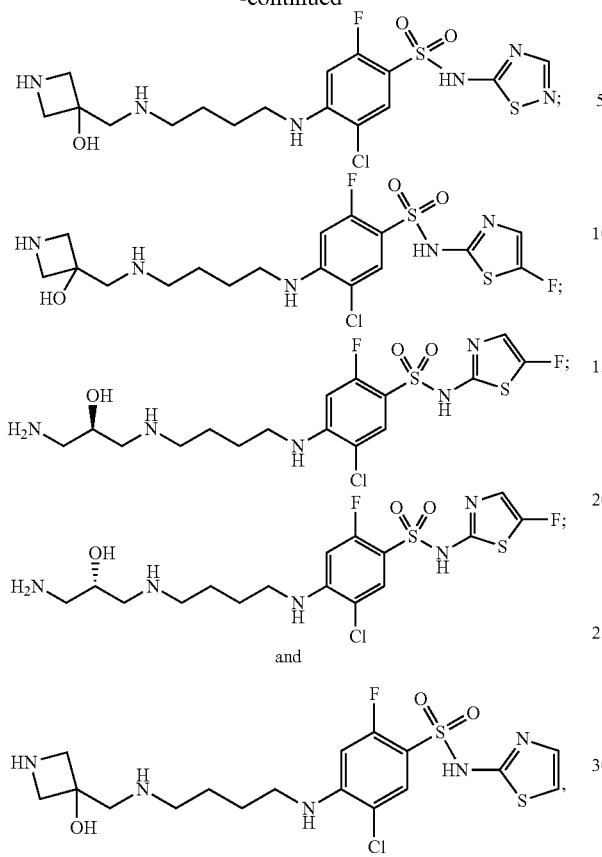

or a pharmaceutically acceptable salt of any thereof.

13. A composition comprising at least one compound of claim 12, or a pharmaceutically acceptable salt thereof, and at least one pharmaceutically acceptable excipient.

14. A compound of the Formula:

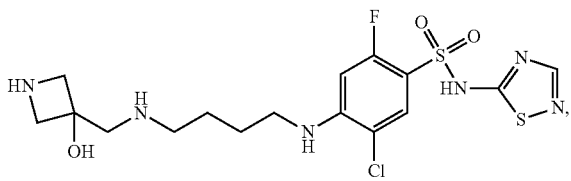

or a pharmaceutically acceptable salt thereof.

15. The compound of claim 14 which is in the form of a pharmaceutically acceptable salt.

16. A pharmaceutical composition comprising an inert carrier and the compound of claim 14 or a pharmaceutically acceptable salt thereof.

17. A compound of the Formula:

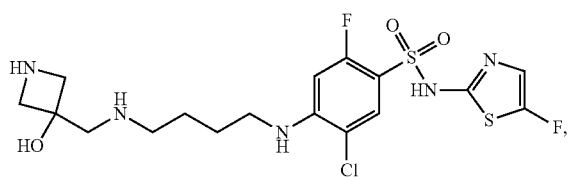 [SMILES: O=S(=O)(Nc1ncc(F)s1)c1cc(Cl)c(NCCCCNCC2(O)CNC2)cc1F]

or a pharmaceutically acceptable salt thereof.

18. The compound of claim 17 which is in the form of a free base.

19. The compound of claim 17 which is in the form of a pharmaceutically acceptable salt.

20. A pharmaceutical composition comprising an inert carrier and the compound of claim 17 or a pharmaceutically acceptable salt thereof.

21. A compound of the Formula:

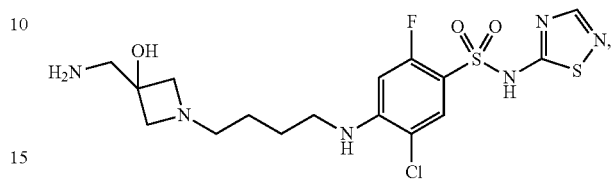

or a pharmaceutically acceptable salt thereof.

22. The compound of claim 21 which is in the form of a free base.

23. The compound of claim 21 which is in the form of a pharmaceutically acceptable salt.

24. A pharmaceutical composition comprising an inert carrier and the compound of claim 21 or a pharmaceutically acceptable salt thereof.

25. A compound of the Formula:

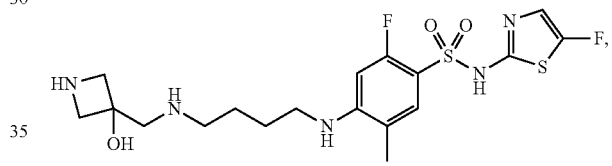

or a pharmaceutically acceptable salt thereof.

26. The compound of claim 25 which is in the form of a free base.

27. The compound of claim 25 which is in the form of a pharmaceutically acceptable salt.

28. A pharmaceutical composition comprising an inert carrier and the compound of claim 25 or a pharmaceutically acceptable salt thereof.

29. A compound of the Formula:

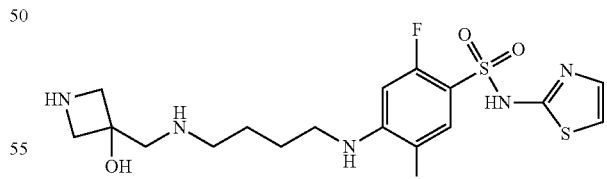

or a pharmaceutically acceptable salt thereof.

30. The compound of claim 29 which is in the form of a free base.

31. The compound of claim 29 which is in the form of a pharmaceutically acceptable salt.

32. A pharmaceutical composition comprising an inert carrier and the compound of claim 29 or a pharmaceutically acceptable salt thereof.

33. A compound of the Formula:

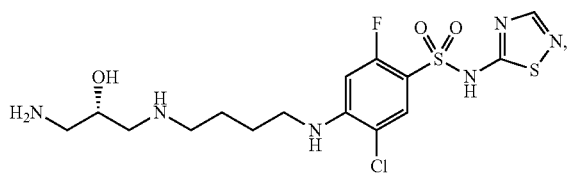 [SMILES: NC[C@H](O)CNCCCCNc1cc(F)c(S(=O)(=O)Nc2ncns2)cc1Cl]

or a pharmaceutically acceptable salt thereof.

34. The compound of claim 33 which is in the form of a free base.

35. The compound of claim 33 which is in the form of a pharmaceutically acceptable salt.

36. A pharmaceutical composition comprising an inert carrier and the compound of claim 33 or a pharmaceutically acceptable salt thereof.

37. A compound of the Formula:

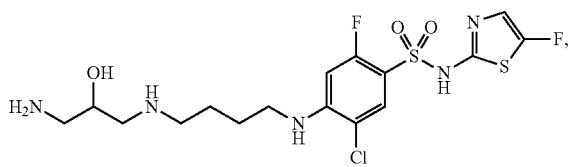 [SMILES: NCC(O)CNCCCCNc1cc(F)c(S(=O)(=O)Nc2ncc(F)s2)cc1Cl]

or a pharmaceutically acceptable salt thereof.

38. The compound of claim 37 which is in the form of a free base.

39. The compound of claim 37 which is in the form of a pharmaceutically acceptable salt.

40. A pharmaceutical composition comprising an inert carrier and the compound of claim 37 or a pharmaceutically acceptable salt thereof.

41. A compound of the Formula:

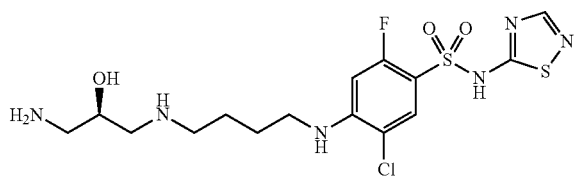 [SMILES: NC[C@@H](O)CNCCCCNc1cc(F)c(S(=O)(=O)Nc2ncns2)cc1Cl]

or a pharmaceutically acceptable salt thereof.

42. The compound of claim 41 which is in the form of a free base.

43. The compound of claim 41 which is in the form of a pharmaceutically acceptable salt.

44. A pharmaceutical composition comprising an inert carrier and the compound of claim 41 or a pharmaceutically acceptable salt thereof.

45. A compound of the Formula:

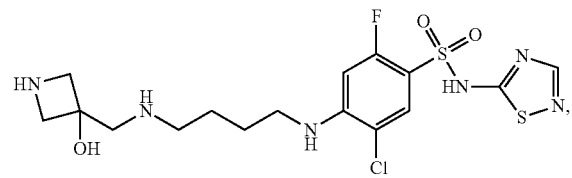 [SMILES: O=S(=O)(Nc1ncns1)c1cc(Cl)c(NCCCCNCC2(O)CNC2)cc1F]

in the form of a dihydrochloride salt.

46. A compound of the Formula:

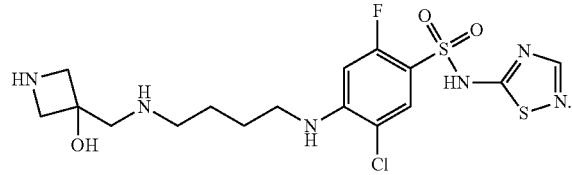

* * * * *